(12) United States Patent
Orr et al.

(10) Patent No.: US 11,007,191 B2
(45) Date of Patent: May 18, 2021

(54) PHARMACEUTICAL COMPOSITIONS AND DOSAGE FORMS

(71) Applicant: IGNYTA, INC., San Diego, CA (US)

(72) Inventors: Robert Orr, San Clemente, CA (US); Kathryn Emily Colombo Pugh, Bend, OR (US); Matthew Jarud Shaffer, Bend, OR (US); Brent Antone Uhrig, Bend, OR (US); Edward Dennis Lachapelle, Bend, OR (US); Charlie Michael McLaughlin, Bend, OR (US)

(73) Assignee: IGNYTA, INC., South San Francisco, CA (US)

( * ) Notice: Subject to any disclaimer, the term of this patent is extended or adjusted under 35 U.S.C. 154(b) by 0 days.

(21) Appl. No.: 16/848,676

(22) Filed: Apr. 14, 2020

(65) Prior Publication Data

US 2020/0237756 A1 Jul. 30, 2020

Related U.S. Application Data

(63) Continuation of application No. PCT/IB2018/058031, filed on Oct. 16, 2018.

(60) Provisional application No. 62/573,275, filed on Oct. 17, 2017.

(51) Int. Cl.
*A61K 31/33* (2006.01)
*A61P 35/00* (2006.01)
*A61K 9/16* (2006.01)
*A61K 31/496* (2006.01)
*A61K 9/20* (2006.01)
*A61K 9/48* (2006.01)

(52) U.S. Cl.
CPC .......... *A61K 31/496* (2013.01); *A61K 9/1635* (2013.01); *A61K 9/1652* (2013.01); *A61K 9/20* (2013.01); *A61K 9/48* (2013.01)

(58) Field of Classification Search
CPC . A61P 35/00; A61K 2039/505; A61K 39/395; A61K 31/496; A61K 9/1635; A61K 9/1652; A61K 9/167; A61K 9/20; A61K 9/48; C07K 16/28; C07K 16/32; C07K 2317/51; C07K 2317/515; C07K 2317/565; C07K 2317/732; C07K 2317/92; C12N 15/02; C12N 1/20; C12N 5/10; C12N 5/12

See application file for complete search history.

(56) References Cited

U.S. PATENT DOCUMENTS

| | | | |
|---|---|---|---|
| 4,555,402 A | 11/1985 | Matsuda et al. | |
| 7,015,231 B2 | 3/2006 | Lackey et al. | |
| 7,230,098 B2 | 6/2007 | Cui et al. | |
| 7,534,792 B2 | 5/2009 | Wittman et al. | |
| 7,790,756 B2 | 9/2010 | Flynn et al. | |
| 7,799,782 B2 | 9/2010 | Munson et al. | |
| 7,964,592 B2 | 6/2011 | Garcia-Echeverria et al. | |
| 8,114,865 B2 | 2/2012 | Bandiera et al. | |
| 8,114,989 B2 | 2/2012 | Wang et al. | |
| 8,299,057 B2 | 10/2012 | Lombardi Borgia et al. | |
| 8,372,858 B2 | 2/2013 | Michellys et al. | |
| 8,404,846 B2 | 3/2013 | Claridge et al. | |
| 8,497,284 B2 | 7/2013 | Bannen et al. | |
| 8,513,263 B2 | 8/2013 | Haas et al. | |
| 8,673,893 B2 | 3/2014 | Lombardi Borgia et al. | |
| 8,680,111 B2 | 3/2014 | Bailey et al. | |
| 9,102,662 B2 | 8/2015 | Lombardi Borgia et al. | |
| 10,085,979 B2 | 10/2018 | Hornby et al. | |
| 10,231,965 B2 | 3/2019 | Lim et al. | |
| 10,357,490 B2 | 7/2019 | Hornby et al. | |
| 10,398,693 B2 | 9/2019 | Codallos et al. | |
| 10,561,651 B2 | 2/2020 | Lim et al. | |
| 2004/0014802 A1 | 1/2004 | Dutruc-Rosset et al. | |
| 2005/0014829 A1 | 1/2005 | Remenar et al. | |
| 2009/0263397 A1 | 10/2009 | Buck et al. | |
| 2010/0197665 A1 | 8/2010 | Bandiera et al. | |
| 2011/0008347 A1 | 1/2011 | Ullrich et al. | |
| 2013/0018036 A1 | 1/2013 | Lombardi Borgia et al. | |
| 2014/0107107 A1 | 4/2014 | Gautschi et al. | |
| 2015/0051222 A1 | 2/2015 | Barbugian et al. | |
| 2015/0283132 A1 | 10/2015 | Lim et al. | |
| 2017/0007599 A1 | 1/2017 | Lim et al. | |
| 2017/0065582 A1 | 3/2017 | Hornby et al. | |
| 2017/0260589 A1 | 9/2017 | Nanda et al. | |
| 2018/0140604 A1 | 5/2018 | Tuch et al. | |
| 2018/0177792 A1 | 6/2018 | Wei | |
| 2018/0333412 A1 | 11/2018 | Lim et al. | |
| 2019/0000840 A1 | 1/2019 | Li et al. | |
| 2019/0022089 A1 | 1/2019 | Codallos et al. | |

(Continued)

FOREIGN PATENT DOCUMENTS

CN 101594862 12/2009
CN 101754956 6/2010

(Continued)

OTHER PUBLICATIONS

Vasanthavada et al. in Water-Insoluble Drug Formulation, 2nd Edition CRC Press 2008: Solid Dispersion versus Physical Mixture p. 6 of 8.) 8 pages (Year: 2008).*

(Continued)

*Primary Examiner* — Ernst V Arnold
(74) *Attorney, Agent, or Firm* — Foley & Lardner LLP

(57) ABSTRACT

The present disclosure relates to pharmaceutical compositions comprising N-[5-(3,5-difluorobenzyl)-1H-indazol-3-yl]-4-(4-methyl-piperazin-1-yl)-2-(tetrahydro-2H-pyran-4-ylamino)-benzamide and a polymer, dosage forms comprising the formulation and methods of treating subjects having cancer.

20 Claims, 8 Drawing Sheets

(56) References Cited

U.S. PATENT DOCUMENTS

| | | | |
|---|---|---|---|
| 2019/0070173 | A1 | 3/2019 | Hornby et al. |
| 2019/0282564 | A1 | 9/2019 | Lim et al. |

FOREIGN PATENT DOCUMENTS

| | | | |
|---|---|---|---|
| CN | 102924479 A | | 2/2013 |
| JP | 2002-275068 A | | 9/2002 |
| JP | 2010-530840 A | | 9/2010 |
| WO | WO-99/43302 A1 | | 9/1999 |
| WO | WO-03/051847 A1 | | 6/2003 |
| WO | WO-03/078403 A2 | | 9/2003 |
| WO | WO-2004/007676 | | 1/2004 |
| WO | WO-2004/022544 A1 | | 3/2004 |
| WO | WO-2004/062662 A1 | | 7/2004 |
| WO | WO-2004/075898 A1 | | 9/2004 |
| WO | WO-2005/040413 A1 | | 5/2005 |
| WO | WO-2006/003276 A1 | | 1/2006 |
| WO | WO-2006/080450 A1 | | 8/2006 |
| WO | WO-2006/111035 A1 | | 10/2006 |
| WO | WO-2007/017497 A2 | | 2/2007 |
| WO | WO-2007/075847 A2 | | 7/2007 |
| WO | WO-2008/003396 A1 | | 1/2008 |
| WO | WO-2008/073480 A1 | | 6/2008 |
| WO | WO-2008/074749 A1 | | 6/2008 |
| WO | WO-2009/013126 A1 | | 1/2009 |
| WO | WO-2013/119950 A2 | | 8/2013 |
| WO | WO-2013/174876 A1 | | 11/2013 |
| WO | WO-2014/093750 A1 | | 6/2014 |
| WO | WO-2015/124697 A1 | | 8/2015 |
| WO | WO-2015/175788 A1 | | 11/2015 |
| WO | WO-2015/189814 A1 | | 12/2015 |
| WO | WO-2016/089760 A1 | | 6/2016 |
| WO | WO-2016/089853 A1 | | 6/2016 |
| WO | WO-2016/196141 A1 | | 12/2016 |
| WO | WO-2016/196671 A1 | | 12/2016 |
| WO | WO-2017/106492 A1 | | 6/2017 |
| WO | WO-2019/018570 A1 | | 1/2019 |
| WO | WO-2019/077506 A2 | | 4/2019 |

OTHER PUBLICATIONS

Aria Vaishnavi, et al., "TRKing down an old oncogene in a new era of targeted therapy", Cancer Discovery, vol. 5(1), pp. 1-19, dated Dec. 19, 2014.

A. Greco et al, "Rearrangements of NTRK1 gene in papillary thyroid carcinoma," Molecular and Cellular Endocrinology, (May 2010), vol. 321, No. 1, ISSN 0303-7207, pp. 44-49.

Adriaenssens, E. et al., Nerve growth factor is a potential therapeutic target in breast cancer, Cancer Res, Jan. 15, 2008, 68(2):346-351.

Albaugh, P. et al., Discovery of GNF-5837, a selective TRK inhibitor with efficacy in rodent cancer tumor models, Med. Chem. Lett, 2012, 3:140-145.

Alecensa® (alectinib) capsules, for oral use, Prescribing Information, Dec. 2015, 16 pp.

Asaumi, K. et al., Expression of neurotrophins and their receptors (TRK) during facture healing, Bone, Jun. 2000, 26(6);625-633.

Aveic et al., "Study of pan-Trk, ROS1, ALK inhibitor, RXDX-101, activity on human neuroblastoma cell lines", Brochure, SIOPEN Annual Meeting 2014, Apr. 23-25, 2014. (1 page).

Awad et al., "ALK inhibitors in non-small cell lung cancer: crizotinib and beyond", Clin Adv Hemotol Oncol, Jul. 2014, 12(7):429-439.

Bardelli, A. et al., Mutational analysis of the tyrosine kinome in colorectal cancers, Science, 2003, 300:949.

Bardelli, A. et al., Mutational analysis of the tyrosine kinome in colorectal cancers, Science, 2003, 300:949; Supplemental Material.

Baserga, R. et al., The IGF-I receptor in cell growth, transformation and apoptosis, Biochip Biophys Acta, 1997, 1332:F105-F126.

Bavetsias, V. et al., Hit generation and exploration: imidazo[4,5-b]pyridine derivatives as inhibitors of aurora kinases, Bioorganic & Medicinal Chemistry Letters, 2007, 17:6567-6571.

Bergethon, K. et al., ROS1 rearrangements define a unique molecular class of lung cancers, Journal of Clinical Oncology, Mar. 10, 2012, 30(8):863-870.

Bhatia et al., Nature Biotechnology, 2012, Nature America, Inc., vol. 30p(7), pp. 604-610 (Year: 2012).

Bouhana, K. et al., LOXO-101, a pan TRK inhibitor, for the treatment of TRK-driven cancers, 26th EORTC-NCI-AACR Symposium on Molecular Targets and Cancer Therapeutics, Barcelona, Spain, Poster, Nov. 2014, Abstract #291, 1 p.

Brodeur et al., "TrK Receptor Expression and Inhibition in Neuroblastomas," Clinical Cancer Research, 15(10), pp. 3244-3250, 2009.

Brodeur, et al., Trk Receptor Expression and Inhibition in Neuroblastomas, Clin Cancer Res 2009: 15(10) May 15, 2009, p. 3244-3250.

Brodeur, G. M., Neuroblastoma: biological insights into a clinical enigma, Nat. Rev. Cancer, Mar. 2003, 3:203-216.

Broekman, F. et al., Tyrosine kinase inhibitors: multi-targeted or single-targeted?, World J. Clin Oncol, Feb. 10, 2011, 2(2):80-93.

Brose, M. et al., LOXO-101, a selective pan-TRK inhibitor for patients with TRK-alterations 15th International Thyroid Congress, Oct. 2015, Lake Buena Vista, Florida, Poster, 1 p.

Brzezianska, E. et al., Rearrangements of NTRK1 oncogene in papillary thyroid carcinoma, Neuroendocrinology Letters, 2007, 28(3):221-229.

Burris, H. A., III. et al., a first-in-human study of LOXO-101, a highly selective inhibitor of the tropomyosin receptor kinase (TRK) family, American Society of Clinical Oncology (ASCO) 2015 Annual Meeting, May-Jun. 2015, Chicago, IL, Poster, 1 p.

Calvo, E., Posters Discussion: Developmental Therapeutics, 2014 ESMO Congress, Sep. 26-30, 2014, 21 pp.

Cao et. al., "Cancer research: past, present and future", Nature Reviews Cancer, 2011, Nature Publishing Group, vol. 11, pp. 749-754.

Chan, LiveScience, "The 10 Deadliest Cancers and Why there's No Cure", 2010, webpage https://www.livescience.com.

Cho, H. et al., Expression of mRNA for brain-derived neurotrophic factor in the dorsal root ganglion following peripheral inflammation, Brain Research, 1997, 749:358-362.

ClinicalTrials.gov, Aug. 20, 2014, A phase 1/2a study of oral RXDX-101 in adult patients with locally advanced or metastatic cancer; study targeting ALK, ROS1 or TRKA/8/C (STARTRK:1), 4 pp.

ClinicalTrials.gov, Aug. 2014, A phase 1/2a study of oral RXDX-101 in adult patients with locally advanced or metastatic cancer; study targeting ALK, ROS1 or TRKA/8/C, 36 pp.

ClinicalTrials.gov, Sep. 11, 2014, A phase 1/2a study oforal RXDX-101 in adult patients with locally advanced or metastatic cancer; study targeting ALK, ROS1 or TRKA/8/C (STARTRK-1), 7 pp.

Cohen, P., Protein kinases—the major drug targets of the twenty-first century?, Nature Reviews, Apr. 2002, Drug Discovery 1:309-315.

Cohen, P., The development and therapeutic potential of protein kinase inhibitors, Current Opinion in Chemical Biology, 1999, 3:459-465.

Collymore, D. C. et al., Genomic testing in oncology to improve clinical outcomes while optimizing utilization: the evolution of diagnostic testing, American Journal of Managed Care, Feb. 2016, 22(2):S20-S28.

Croucher et al., "TrkB inhibition by GNF-4256 slows growth and enhances chemotherapeutic efficacy in neuroblastoma xenografts", Cancer Chemother Pharmacol, 2015, 75:131-141.

Dang, C. et al., Expression of nerve growth factor receptors is correlated with progression and prognosis of human pancreatic cancer, Journal of Gastroenterology and Hepatology, 2006, 21(5):850-858.

Davidson, B. et al., Expression and activation of the nerve growth factor receptor TrkA in serous ovarian carcinoma, Clin. Cancer Res., Jun. 2003, 9:2248-2259.

Davies, K. D. et al., Resistance of ROS1 inhibition mediated by EGFR pathway activation in non-small cell lung cancer, PLoS One, Dec. 2013, 8(12):e82236.

(56) References Cited

OTHER PUBLICATIONS

Davies, K. et al., Identifying and targeting ROS1 gene fusions in non-small cell lung cancer, Clin Cancer Res, Sep. 1, 2012, 18(17):4570-4579.
De Braud, F. et al., 2014, Phase 1 open label, dose escalation study of RXDX-101, an oral pan-trk, ROS1, and ALK inhibitor, in patients with advanced solid tumors with relevant molecular alterations, Poster, 1P.
De Braud, F. et al., 2014, RXDX-101, an oral pan-TRK, POS1, and ALK inhibitor, in patients with advanced solid tumors with relevant molecular alterations, Annals of Oncology 25(Supplement 4): iv146-iv164 (abstract).
De Braud, F., 2014, Phase 1 open label, dose escalation study of RXDX-101, an oral pan-trk, ROS1, and ALK inhibitor, in patients with advanced solid tumors with relevant molecular alterations, PowerPoint presentation, ASCO 50th Annual Meeting, 18 pp.
De Melo-Jorge, M. et al., The chagas' disease parasite trypanosoma cruzi exploits nerve growth factor receptor TrkA to infect mammalian hosts, Cell Host & Microbe, Jun. 2007, 1(4):251-261.
Delafoy, L. et al., Role of nerve growth factor in the trinitrobenzene sulfonic acid-induced colonic hypersensitivity, Pain, 2003, 105:489-497.
Di Mola, F. F. et al., Nerve growth factor and Trk high affinity receptor (TrkA)gene expression in inflammatory bowel disease, Gut, 2000, 46(5):670-678.
Dionne, C. A. et al., Cell cycle-independent death of prostate adenocarcinoma is induced by the trk tyrosine kinase inhibitor CEP-751 (KT6587), Clin. Cancer Res., Aug. 1998, 4(8):1887-1898.
Doebele, R. C. et al., An oncogenic NTRK fusion in a patient with soft-tissue sarcoma with response to the tropomyosin-related kinase inhibitor LOXO-101, Cancer Discovery, Oct. 2015, 1049-1057.
Dou, Y. et. al., 2006, Increased nerve growth factor and its receptors in atopic dermatitis: an immunohistochemical study, Archives of Dermatological Research, 2008, 298(1):31-37.
Drilon et al., "Safety and Antitumor Activity of the Multitargeted Pan-TRK, ROS1, and ALK Inhibitor Entrectinib: Combined Results from Two Phase I Trials (ALKA-372-001 and STARTRK-1)", Published OnlineFirst Feb. 9, 2017, Downloaded from cancerdiscovery.aacrjournals.org on Apr. 7, 2017, pp. 401-409.
Drug Class Detail: Trk Receptor Inhibitor (Pan); https://ckb.jax.org/drugClass/show?drugClassId=Trk Receptor Inhibitor %28Pan%29: (Jul. 16, 2014).
Duffy, M. J. et al., Companion biomarkers: paving the pathway to personalized treatment for cancer, Clinical Chemistry, 2013, 59(1):1447-1456.
Estrada-Bernal et al., "TRK kinase domain mutations that induce resistance to a pan-TRK inhibitor", [abstract]. In: Proceedings of the AACR-NCI-EORTC International Conference: Molecular Targets and Cancer Therapeutics; Nov. 5-9, 2015; Boston, MA. Philadelphia (PA): AACR; Mol Cancer Ther 2015;14(12 Suppl 2):Abstract nr C65.
Evans et al., "Antitumor Activity of CEP-751 (KT-6587) on Human Neuroblastoma and Medulloblastoma Xenografts", American Association for Cancer Research, 1999, 5:3594-3602.
Freund-Michel, V. et al., The nerve growth factor and its receptors in airway inflammatory diseases, Pharmacology & Therapeutics, 2008, 117(1):52-76.
Gad et al., "Neurotrophic activities of trk receptors conserved over 600 million years of evolution", J. Neurobiol., 2004;60(1):12-20.
Gainor, Justin, MD,RXDX-101 & RXDX-102, PowerPoint Presentation, Feb. 20, 2014, 13 pp.
Greco, A. et al., Rearrangement of NKRK1 gene in papillary thyroid carcinoma, Molecular and Cellular Endocrinology, May 1, 2010, 321(1):44-49.
Hansen, K. et al., Autophagic cell death induced by TrkA receptor activation in human glioblastoma cells, Journal of Neurochemistry, 2007, 103:259-275.
Hatcher, John M. et al: "Discovery of Inhibitors That Overcome the G1202R Anaplastic Lymphoma Kinase Resistance Mutation", Journal of Medicinal Chemistry, vol. 58, No. 23, Nov. 25, 2015 (Nov. 25, 2015), pp. 9296-9308, XP055603442, US ISSN: 0022-2623, DOI:10.1021/acs.jmedchem.5b01136.
Ho A et al: "Overcoming drug resistance to Trk inhibition by rational combination of entrectinib and trametinib: from bench to bedside", European Journal of Cancer, vol. 69,Dec. 2, 2016, XP029843502, ISSN:0959-8049, DOI: 10.1016/S0959-8049(16)32615-6.
Hofmann, F. et al., Blocking insulin-like growth factor-I receptor as a strategy for targeting cancer, Drug Discov Today, Aug. 2005, 10(15):1041-1047.
Holt et al., British Journal of Cancer, 2012, Nature Publishing Group, vol. 106, pp. 858-866 (Year 2012).
Hu, V. Y. et al., Decrease in bladder overactivity with ren1820 in rats with cyclophosphamide induced cystitis, The Journal of Urology, 2005, 173(3):1016-1021.
Hu, Y. et al., Identification of brain-derived neurotrophic factor as a novel angiogenic protein in multiple myeloma, Cancer Genetics and Cytogenetics, 2007, 178:1-10.
Iannone et al., "Increased expression of nerve growth factor (NGF) and high affinity NGF receptor (p140 TrkA) in human osteoarthritic chondrocytes", Rheumatology, 2002;41:1413-1418.
Ignyta Inc., Aug. 12, 2014, Ignyta announces second quarter 2014 company highlights and financial results, Press Release, 4 pp.
Ignyta Inc., Dec. 3, 2013, Ignyta announces completion of $54 million in private placements to catalyze precision medicine for cancer patients, Press Release, 2 pp.
Ignyta Inc., Feb. 20, 2014, Ignyta announces preliminary data from RXDX-101 phase I clinical trial, Press Release, 2 pp.
Ignyta Inc., Feb. 27, 2014, Ignyta announces of IND for RXDX-101, Press Release, 2 pp.
Ignyta Inc., Feb. 28, 2014, Ignyta announces 2013 company highlights and full year financial results, Press Release, 5 pp.
Ignyta Inc., Jul. 21, 2014, Ignyta announces initiation of STARTKR-1 global phase I/II clinical trial of RXDX-101, Press Release, 2 pp.
Ignyta Inc., May 31, 2014, Ignyta announces interim data from RXDX-101 phase I clinical trial, Press Release, 2 pp.
Ignyta Inc., May 7, 2014, Ignyta announces RXDX-101 phase I data abstract accepted for oral presentation at the 2014 ASCO annual meeting, Press Release, 2 pp.
Ignyta Inc., Nov. 1, 2013, Ignyta completes merger and announces license agreement for the development of two leading tyrosine kinase inhibitors, Press Release, 1 p.
Ignyta Inc., Nov. 18, 2014, Ignyta announces RXDX-101 phase 1 presentations at the 2014 EORTC-NCI-AACR 'molecular targets and cancer therapeutics' conference, Press Release, 2 pp.
Ignyta Inc., Nov. 7, 2014, Ignyta announces third quarter 2014 company highlights and financial results, Press Release, 5 pp.
Ignyta Inc., Sep. 15, 2014, Ignyta announces RXDX-101 phase 1 data presentation at the 2014 ESMO Congress, Press Release, 2 pp.
Ignyta Inc., Sep. 28, 2014, Ignyta announces interim data from RXDX-101 phase I clinical trial at 2014 ESMO Congress, Press Release, 2 pp.
Ignyta, "Overcoming drug resistance to TRK inhibition by rational combination of entrectinib and trametinib: from bench to bedside", 28th EORTC-NCI-AACR symposium, Nov. 1, 2016, XP055603929, Retrieved from the Internet: URL:https://pdfs.semanticscholar.org/9270/3fe8a73b37ee47aa4b0af036f1 ea762348de.pdf [retrieved on Jul. 9, 2019].
Ignyta, Feb. 2014, Catalyzing precision medicine with integrated Rx/Ox in oncology, presentation, 23 pp.
Ignyta, Inc., Feb. 20, 2014, Form 8-K (Current Report Filing), 20 pp.
Ignyta, Inc., Jan. 13, 2014, Form 8-K (Current Report Filing), 28 pp.
Ignyta, Inc., Jun. 2, 2014, Form 8-K (Current Report Filing), 26 pp.
Ignyta, Inc., May 12, 2014, Form 8-K (Current Report Filing), 11 pp.
Ignyta, Inc., May 2, 2014, Form 8-K (Current Report Filing), 4 pp.
Ignyta, Inc., Nov. 7, 2014, Form 8-K (Current Report Filing), 13 pp.
Ignyta, Inc., Oct. 14, 2014, Form 8-K (Current Report Filing), 61 pp.
Infante et. al., Lancet Oncology, 2012, vol. 13, pp. 773-781 (Year: 2012).

(56) References Cited

OTHER PUBLICATIONS

International Search Report and Written Opinion issued in PCT/IB2018/058031 dated Feb. 12, 2019.
Isaacson, Jerry, Ph.D. et al., "Ignyta, Inc.: Initiation of Coverage," LifeSci Advisors Research, Feb. 14, 2014, pp. 1-37.
Iyer et al., "AZ64 inhibits TrkB and enhances the efficacy of chemotherapy and local radiation in neuroblastoma xenografts", Cancer Chemother Pharmacol, 2012, 70:477-486.
Iyer et al., "Lestaurtinib Enhances the Antitumor Efficacy of Chemotherapy in Murine Xenograft Models of Neuroblastoma", Clin Cancer Res; 2010; 16(5):1478-1485.
Iyer et al., "The TRK Inhibitor Entrectinib Enhances the Efficacy of Temozolomide and Irinotecan in a Xenograft Model of Neuroblastoma", Abstract #5390, Brochure, AACR Annual Meeting 2015 (1 page).
Iyer et al., "Abstract 5390: The TRK Inhibitor RXDX-101 enhances the efficacy of temozolomide and irinotecan in a xenograft model of neuroblastoma," Cancer Research, Aug. 1, 2015, vol. 75, Iss. 15, Supplement, p. 5390.
Iyer, et al. "Lestaurtinib Enhances the Antitumor Efficacy of Chemotherapy in Murine Xenograft Models of Neuroblastoma", Clinical Cancer Research, Pub. Online Feb. 23, 2010 as 10.158/1078-0432.CCR-09-1531.
Iyer, R., et al., Entrectinib Is a Potent Inhibitor of TRK-Driven Neuroblastomas in a Xenograft Mouse Model, Cancer Letters 372 (2016) pp. 179-186, http://dx.doi.org/10.1016/j.canlet.2016.01.018.
Jaggar, S. I. et al., Inflammation of the rat urinary bladder is associated with a referred thermal hyperalgesia which is nerve growth factor dependent, Br. J. Anaesth., 1999, 83:442-448.
Jantzen, G. M. et al., "Sustained- and controlled-release drug delivery systems", in Banker et al. eds., Modern Pharmaceutics, 1996, 3rd Ed. pp. 575-609, Marcel Dekker, Inc., New York, NY.
Johnson, T. W. et al., Discovery of (10R)-7-Amino-12-fluoro-2,10,16-trimethyl-15-oxo-10,15,16,17-tetrahydro-2H-8,4-(metheno)pyrazolo[4,3-h][2,5,11]-benzoxadiazacyclotetradecine-3-carbonitrile (PF-06463922), a macrocyclic inhibitor of anaplastic lymphoma kinase (ALK) and c-ros oncogene 1(ROS1) with preclinical brain exposure and broad-spectrum potency against ALK-resistant mutations, Journal of Medicinal Chemistry, 2014, 57(11);4720-4744.
Karaman, M. W. et al., A quantitative analysis of kinase inhibitor selectivity, Nature Biotechnology, Jan. 2008, 26(1):127-132.
Khandwala, H. M. et al., The effects of insulin-like growth factors on tumorigenesis and neoplastic growth, Endocr Rev, 2000, 21(3):215-244.
Kruettgen, A. et al., The dark side of the NGF family: neurotrophins in neoplasias, Brain Pathology, 2006, 16:304-310.
Kushner, BH, et al. Irinotecan plus temozolomide for relapsed or refractory neuroblastoma. J Clin Oncol. Nov. 20, 2006;24(33):5271-6.
Lamant et al., 2000, Expression of the ALK tyrosine kinase gene in neuroblastoma, American Journal of Pathology, 156:1711-1721.
Lamb, K. et al., Nerve growth factor and gastric hyperalgesia in the rat, Neurogastroenterol. Motil, 2003, 15:355-361.
Laron, Z., Laron syndrome (primary growth hormone resistance or insensitivity): the personal experience 1958-2003, J Clin Endocrinol Metab, 2004, 89(3):1031-1044.
Le Roith, D. et al., The somatomedin hypothesis: 2001, Endocr Rev, 2001, 22(1):53-74.
Lee et al., "Mechanisms of Constitutive Activation of Janus Kinase 2-V617F Revealed at the Atomic Level Through Molecular Dynamics Simulations 1," Cancer, vol. 115, No. 8, pp. 1692-1700 (2009).
Lee, J. et al., Identification of ROS1 rearrangement in gastric adenocarcinoma, Cancer, May 1, 2013, 119:1627-1635.
Lewis et al., "The Discovery and Optimization of a Novel Class of Potent, Selective, and Orally Bioavailable Anaplastic Lymphoma Kinase (ALK) Inhibitors with Potential Utility for the Treatment of Cancer", Journal of Medicinal Chemistry, 2012; 55(14): 6523-6540.

Li et al., "Abstract A173: Potent anti-tumor activity of entrectinib in patient-derived models harboring oncogenic gene rearrangements of NTRKs," Molecular Cancer Therapeutics, (2015), 14(12):Supplement 2, p. A173.
Li, Q. et al., Brain derived neurotrophic factor (BDNF) contributes to the pain hypersensitivity following surgical incision in the rats, Molecular Pain, 2008, 4:27, 11 pp.
Li, T. et al., Genotyping and genomic profiling of Non-Small-Cell lung cancer: implications for current and future therapies, Journal of Clinical Oncology, Mar. 10, 2013, vol. 31, No. 8, pp. 1039-1049.
Lindeman, N. I., MD et al., Molecular testing guideline for selection of lung cancer patients for EGFR and ALK tyrosine kinase inhibitors, Journal of Thoracic Oncology, Jul. 2013, 8(7):823-859.
Lipska, B. S. et al., c.1810C>T polymorphism of NTRK1 gene is associated with reduced survival in neuroblastoma patients, BMC Cancer, Biomed Central, Dec. 13, 2009, London, GB, 9(1):436.
Ma, Q. et al., The progressive tactile hyperalgesia induced by peripheral inflammation is nerve growth factor dependent, Neuroreport, 1997, 8(4):807-810.
Marchetti, A. et al., Frequent mutations in the neurotrophic tyrosine receptor kinase gene family in large cell neuroendocrine carcinoma of the lung, Human Mutation, 2008, 29(5):609-616.
Marshall et.al., Investigational New Drugs, 2005, vol. 23, pp. 31-37 (Year 2005).
Marsilje, T. H. et al., Synthesis, structure-activity relationsnips and in vivo efficacy of the novel potent and selective anaplastic lymphoma kinase (ALK) inhibitor LDK378 currently in phase 1 and 2 clinical trials, J. Med. Chem., 2013, 56:5675-5690 and Supporting Information.
Matayoshi, S. et al., Actions of brain-derived neurotrophic factor on spinal nociceptive transmission during inflammation in the rat, J. Physiol., 2005, 569(2):685-695,.
McMahon, S. B. et al., The biological effects of endogenous nerve growth factor on adult sensory neurons revealed by a trkA-IgG fusion molecule, Nat. Med., Aug. 1995, 1(8):774-780.
Meyer, J. et al., Remarkable leukemogenic potency and quality of a constitutively active neurotrophin receptor, ΔTrkA, Leukemia, 2007, 21:2171-2180.
Milkeiwicz, K. L. et al., Inhibitors of anaplastic lymphoma kinase: a patent review, Expert Opin. Ther. Patents, 2010, 20(12):1653-1681.
Ming Chi et al: "Targeted drug development in melanoma and nonsmall cell lung cancer: BRAF, MEK, and ALK inhibitors", MEMO—Magazine of European Medical Oncology, Springer Vienna, Vienna, vol. 5, No. 4, Nov. 20, 2012, pp. 302-308, XP035152606, ISSN:1865-5076, DOI: 10.1007/S12254-012-0058-4.
Minturn et al, "Phase I trial of lestaurtinib for children with refractory neuroblastoma: a new approaches to neuroblastoma therapy consortium study," Cancer Chemother Pharmacol, Feb. 22, 2011, 9 pages.
Molina-Vila, M. A. et al., Impact of the new EGF receptor and ALK testing guideline on personalized lung cancer medicine, Personalized Medicine, 2013, 19(5):415-417.
Murphy et al., "Monitoring activity of RXDX-101 in Phase 1/2 patients using a pharmacodynamics assay for TrkA activation", European Journal of Cancer, Poster Session—Molecular Targeted Agents II, 2014, 50(6):143-144.
Nakagawara et al.; "Association between high levels of expression of the Trk gene and favorable outcome in human neuroblastoma"; N Engl J Med; 1993; 328:847-54.
Nakagawara, "Trk receptor tyrosine kinases: A bridge between cancer and neural development", Cancer Letters, vol. 169, Apr. 6, 2001, pp. 107-114.
Nakagawara,A., et al., Expression and Function of TRK-B and BDNF in Human Neuroblastomas, Molecular and Cellular Biology,Jan. 1994, p. 759-767.
National Comprehensive Cancer Network, NCCN Clinical Practice Guidelines in Oncology: Non-small cell lung cancer, Apr. 2016, Version 4.2016. 169 pp.
Okimoto, R. A. et al., Recent advances in personalized lung cancer medicine, Personalized Medicine, 2014, 11(3):309-321.

(56) References Cited

OTHER PUBLICATIONS

Omura et al., "A New Alkaloid AM-2282 of *Streptomyces* Origin Taxonomy, Fermentation, Isolation and Preliminary Characterization", Journal of Antibiotics, 1977, 30(4):275-282.
Pardue et al., "Nucleic Acid Hybridization. A practical approach", IRL Press, Oxford Washington/DC. 1985:170-203.
Patapoutian A. et al., Trk receptors: mediators of neurotropnin action, Current Opinion in Neurobiology, 2001, 11:272-280.
Perez-Pinera,P. et al., The Trk tyrosine kinase inhibitor K252a regulates growth on lung adenocarcinomas, Molecular and Cellular Biochemistry, 2007, 295:19-26.
Pierotti, A. et al., Oncogenic rearrangements of the NRTK1/NGF receptor, Cancer Letters, 2006, 232:90-98.
Pinski, J. et al., Trk receptor inhibition induced apoptosis of proliferating but not quiescent human osteoblasts, Cancer Research, Feb. 15, 2002, 62:986-989.
Puig De La Bellacasa, R. et al., ALK and ROS1 as a joint target for the treatment of lung cancer: a review, Translational Lung Cancer Research, 2013, vol. 2, No. 2, pp. 72-86.
Raychaudhuri, S. P. et al., K252a, a high-affinity nerve growth factor receptor blocker, improves psoriasis: an in vivo study using the severe combined immunodeficient mouse-human skin model, Journal of Investigative Dermatology, Mar. 3, 2004, 122(3);812-819.
Russo et al., "Acquired Resistance to the TRK Inhibitor Entrectinib in Colorectal Cancer," Cancer Discovery, (2016), 6:36-44.
Russo et al.: "Acquired Resistance to the TRK Inhibitor Entrectinib in Colorectal Cancer", Cancer Discov, vol. 6, Nov. 6, 2015, pp. 36-44, XP055294187.
Sakamoto, H. et al., CH5424802, a selective ALK inhibitor capable of blocking the resistant gatekeeper mutant, Cancer Cell, 2011, 19:679-690.
Shaw, A. T. et al., Crizotinib versus chemotherapy in advanced ALK-positive lung cancer, The New England Journal of Medicine, Jun. 30, 2013, 268(25):2385-2394.
Shaw, A. T. et al., Targeting anaplastic lymphoma kinase in lung cancer, Clin. Cancer Res., 2011, 17:2081-2086.
Shelton, D. et al., Nerve growth factor mediates hyperalgesia and cachexia in auto-immune arthritis, Pain, 2005, 116:8-16.
Sikora, Personalized Medicine, 2005, Future Med.Ltd, vol. 2(1), pp. 5-9 (Year 2005).
Sohrabji, F. et al., Estrogen-BDNF interactions: implications for neurodegenerative diseases, Neuroendocrinology, 2006, 27(4):404-414.
Stumpfova, M. et al., Zeroing in on ROS1 rearrangements in non-small cell lung cancer, Clin Cancer Res, Aug. 2, 2012, 18(16):4222-4224.
Tanizaki, J. et al: "Combined effect of ALK and MEK inhibitors in EML4-ALK-positive non-small-cell lung cancer cells", British Journal of Cancer, vol. 106, No. 4, Jan. 12, 2012, pp. 763-767, XP055603437, GB ISSN: 0007-0920, DOI: 10.1038/bjc.2011.586.
Tatematsu, T. et al., Investigation of neurotrophic tyrosine kinase receptor 1 fusions and neurotrophic tyrosine kinase receptor family expression in non-small-cell lung cancer and sensitivity to AZD7451 in vitro, Molecular and Clinical Oncology, 2014, 2:725-730.
Teofilo Vasconcelos et al., "Solid dispersions a strategy to improve oral bioavailability of poor water soluble drug", Drug Discover Today, vol. 12, Jan. 1, 2012 (Jan. 1, 2012), pp. 1068-1075, XP055376574, DOI: 10.1016/j.drudis.2007.09.005.
Thompson S. W. N. et al., Brain-derived neurotrophic factor is an endogenous modulator of nociceptive responses in the spinal cord, Proc. Natl. Acad. Sci. USA, Jul. 1999, 96:7714-7718.
Tremodar PI-2, Highlights or Prescribing Information, 2014. (17 pages).
Truzzi, F. et al., Neurotrophins and their receptors stimulate melanoma cell proliferation and migration, Journal of Investigative Dermatology, 2008, 128(8):2031-2040.

Tzelepi, V., Editorial: Personalized cancer treatment, Current Molecular Pharmacology, 2014, 7(1), 2 pp.
Uehling Davide et al: "Recent progress on MAP kinase pathway inhibitors", Bioorganic & Medicinal Chemistry Letters, Pergamon, Amsterdam, NL, vol. 25, No. 19, Aug. 1, 2015, pp. 4047-4056, XP029264241, ISSN: 0960-894X, DOI: 10.1016/J.BMCL. 2015.07.093.
Uniprot Accession P04629. "NTRK1_human", (Jun. 24, 2015), available on the internet: http://www.uniprot.org/uniprot/P04629.txt?version=204 (12 pages).
Vaishnavi, A. et al., Oncogenic and drug sensitive NTRK1 rearrangements in lung cancer, Nat Med., Nov. 2013, 19(11):1469-1472.
Valent, A. et al. Mapping of the tyrosine kinase receptors trkA (NTRK1), trkB (NTRK2) and trkC(NTRK3) to human chromosomes 1q22, 9q22 and 15q25 by fluorescence in situ hybridization. Eur.J. Hum. Genet (1997), vol. 5(2), pp. 102-104.
Valentinis, B. et al., IGF-I receptor signaling in transformation and differentiation, 2001, Mol Pathol, 54:133-137.
Vasconcelos et al., "Solid dispersions a strategy to improve oral bioavailability of poor water soluble drug," Drug Discovery Today, vol. 12, Jan. 2012, pp. 1068-1075.
Voskoglou-Nomikos, T. et al., Clinical predictive value of the in vitro cell line, human xenograft, and mouse allograft preclinical cancer models, Clinical Cancer Research, Sep. 15, 2003, 9:4227-4239.
Wang, Y. et al., Insulin-like growth factor receptor-1 as an anticancer target: blocking transformation and inducing apoptosis, Curr Cancer Drug Targets, 2002, 2:191-207.
Warner, S. et al., Targeting aurora-2 kinase in cancer, Molecular Cancer Therapeutics, Jun. 3, 2003, 2:589-595.
Wei et al., "Abstract 2136: Entrectinib is effective against the gatekeeper and other emerging resistance mutations in NTRK-, ROS1- and ALK-rearranged cancers", [abstract], Proceedings: AACR 107th Annual Meeting 2016; Apr. 16-20, 2016: New Orleans, LA; 2016;76(14 Suppl):Abstract nr 2136.
Weroha, S. J. et al., IFG-1 receptor inhibitors in clinical trials-early lessons, J. Mammary Gland Biol. Neoplasia, 2008, vol. 13, pp. 471-483.
Wolff, M.E., Burger's Medicinal Chemistry and Drug Discovery, 5th Ed. vol. 1, 1995, pp. 975-977, John Wiley & Sons, Inc., New York, NY.
Wood et al., "Somatic Mutations of GUCY2F, EPHA3, and NTRK3 in Human Cancers", Human Mutation in Brief #923, 2006. (9 pages).
Woolf, C. J. et al., Letter to Neuroscience: Nerve growth factor contributes to the generation of inflammatory sensory hypersensitivity, Neuroscience, 1994, vol. 62, No. 2, pp. 327-331.
Xalkori® (crizotinib) capsules, for oral use, Prescribing Information, Mar. 2016, 27 pp.
Zahn, P. et al., Effect of blockade of nerve growth factor and tumor necrosis factor on pain behaviors after plantar incision, J. Pain, vol. 5 No. 3, Apr. 2004, pp. 157-163.
Zhu et al., "Nerve Growth Factor Expression Correlates With Perineural Invasion and Pain in Human Pancreatic Cancer", Journal of Clinical Oncology, 1999;17:2419-2428.
Zhu, L., et al. Implications of tropomyosin-related kinase B (TrkB) in head and neck cancer. Anticancer Res. Sep.-Oct. 2007;27(5A):3121-6.
Zykadia™ (ceritinib) capsules, for oral use, Prescribing Information, Apr. 2014, 16 pp.
Lee et al, "Mechanisms of Constitutive Activation of Janus Kinase 2-V617F Revealed at the Atomic Level Through Molecular Dynamics Simulations", Cancer, vol. 115, No. 8, Apr. 2009 (Apr. 2009), pp. 1692-1700.

* cited by examiner

Figure 1

| Average Relative Abundance >LOQ | | | | | | | |
|---|---|---|---|---|---|---|---|
| Retention Time (min) | Timepoint | Stability Temperature | 6.98 | 8.34 active | 9.18 | 11.24 | 23.21 | Total Impurities >LOQ |
| Relative Ret. Time | 0 | 0 | 0.84 | 1.00 | 1.10 | 1.35 | 2.78 | |
| CAT4-0259 | 0 | N/A | 0.10 | 99.84 | 0.08 | ND | <LOQ | 0.18 |
| 0 Day 80/20 acetone/water, 12.5wt% solids | 0 | 25 | 0.10 | 99.76 | 0.08 | <LOQ | 0.07 | 0.24 |
| 1 Day 80/20 acetone/water, 12.5wt% solids | 1 | 25 | 0.10 | 99.76 | 0.08 | <LOQ | 0.07 | 0.24 |
| 2 Day 80/20 acetone/water, 12.5wt% solids | 2 | 25 | 0.10 | 99.74 | 0.09 | <LOQ | 0.07 | 0.26 |
| 3 Day 80/20 acetone/water, 12.5wt% solids | 3 | 25 | 0.10 | 99.75 | 0.09 | <LOQ | 0.07 | 0.25 |
| 7 Day 80/20 acetone/water, 12.5wt% solids | 7 | 25 | 0.10 | 99.72 | 0.13 | 0.06 | <LOQ | 0.28 |
| 0 Day 90/10 acetone/water, 12.5wt% solids | 0 | 25 | 0.10 | 99.74 | 0.09 | <LOQ | 0.07 | 0.26 |
| 1 Day 90/10 acetone/water, 12.5wt% solids | 1 | 25 | 0.09 | 99.75 | 0.08 | <LOQ | 0.07 | 0.25 |
| 2 Day 90/10 acetone/water, 12.5wt% solids | 2 | 25 | 0.10 | 99.73 | 0.11 | <LOQ | 0.06 | 0.27 |
| 3 Day 90/10 acetone/water, 12.5wt% solids | 3 | 25 | 0.10 | 99.74 | 0.10 | <LOQ | 0.07 | 0.26 |
| 7 Day 90/10 acetone/water, 12.5wt% solids | 7 | 25 | 0.09 | 99.70 | 0.14 | 0.06 | <LOQ | 0.30 |
| 0 Day 95/5 acetone/water, 12.5wt% solids | 0 | 25 | 0.10 | 99.75 | 0.09 | <LOQ | 0.07 | 0.26 |
| 1 Day 95/5 acetone/water, 12.5wt% solids | 1 | 25 | 0.10 | 99.74 | 0.09 | <LOQ | 0.07 | 0.28 |
| 2 Day 95/5 acetone/water, 12.5wt% solids | 2 | 25 | 0.10 | 99.76 | 0.11 | <LOQ | <LOQ | 0.27 |
| 3 Day 95/5 acetone/water, 12.5wt% solids | 3 | 25 | 0.10 | 99.73 | 0.11 | <LOQ | 0.07 | 0.27 |
| 7 Day 95/5 acetone/water, 12.5wt% solids | 7 | 25 | 0.10 | 99.66 | 0.15 | 0.07 | <LOQ | 0.31 |

Figure 2

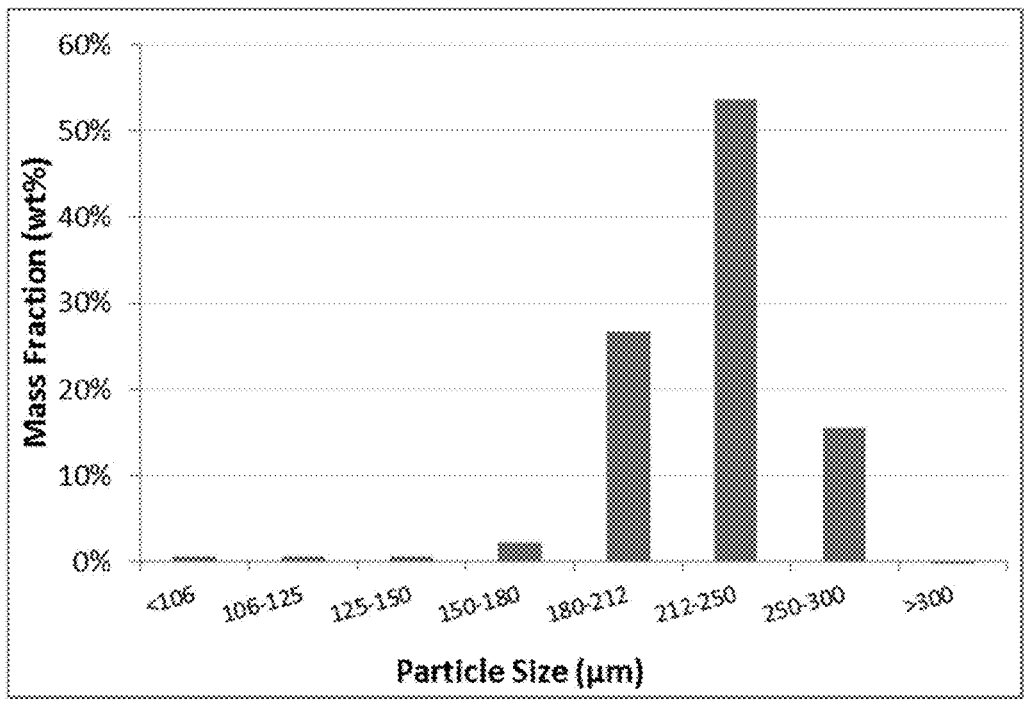

| Sample: | | $T_g$ (°C) | | $T_m$ (°C) | |
|---|---|---|---|---|---|
| Formulation | Lot Number | Average | Std Dev | Average | Std Dev |
| ~30%cwt SLD 80/20 Entrectinib/PVP-VA | BREC1456-130A | 102 | 0.1 | 197 | 0.1 |
| ~40%cwt SLD 80/20 Entrectinib/PVP-VA | BREC1456-130B | 101 | 1.1 | 197 | 0.2 |
| ~50%cwt SLD 80/20 Entrectinib/PVP-VA | BREC1456-130C | 100 | 0.1 | 196 | 0.1 |
| ~55%cwt SLD 80/20 Entrectinib/PVP-VA | BREC1456-130D | 101 | 0.1 | 197 | 0.1 |
| 75/25 Entrectinib/PVP-VA SDD | BREC1461-003C | 111 | 0.4 | N/A | N/A |
| 90/10 Entrectinib/PVP-VA SDD | BREC1461-005B | 109 | 0.1 | N/A | N/A |
| 100% Entrectinib | BREC1461-005C | 108 | 0.1 | N/A | N/A |

|  | %Dose Dissolved (based on Label Claim) | | | | | |
|---|---|---|---|---|---|---|
|  | vessel 1 | vessel 2 | vessel 3 | vessel 4 | vessel 5 | vessel 6 |
| 10 minute | 100.9 | 115.8 | 88.4 | 101.3 | 101.3 | 63.7 |
| 20 minute | 100.5 | 102.3 | 99.6 | 100.7 | 100.4 | 96.0 |
| 30 minute | 100.6 | 100.8 | 101.4 | 101.0 | 100.4 | 100.8 |
| 45 minute | 100.8 | 100.7 | 101.3 | 101.1 | 100.6 | 100.9 |
| 60 minute | 100.7 | 100.9 | 101.4 | 101.0 | 100.6 | 100.9 |

PHARMACEUTICAL COMPOSITIONS AND DOSAGE FORMS

CROSS-REFERENCE TO RELATED APPLICATIONS

This application is a Continuation of International Patent Application No. PCT/IB2018/058031, filed Oct. 16, 2018, which claims the benefit of the priority date of U.S. Provisional Application No. 62/573,275, filed on Oct. 17, 2017, each of which is hereby incorporated by reference herein in its entirety.

FIELD

The present disclosure relates to pharmaceutical compositions and dosage forms that are useful in the treatment of subjects having cancer. The present disclosure also provides methods for preparing these pharmaceutical compositions and dosage forms, and methods of treating subjects having cancer utilizing the pharmaceutical compositions and dosage forms provided herein.

BACKGROUND

The compound N-[5-(3,5-difluorobenzyl)-1H-indazol-3-yl]-4-(4-methyl-piperazin-1-yl)-2-(tetrahydro-2H-pyran-4-ylamino)-benzamide and its preparation have been disclosed in U.S. Pat. No. 8,299,057, the contents of which are hereby incorporated by reference in their entirety. N-[5-(3,5-difluorobenzyl)-1H-indazol-3-yl]-4-(4-methyl-piperazin-1-yl)-2-(tetrahydro-2H-pyran-4-ylamino)-benzamide is a potent inhibitor of tyrosine kinases, NTRK1/2/3-transforming tyrosine kinase proteins (TrkA, TrkB, TrkC), proto-oncogene tyrosine-protein kinase 1 (ROS1), and anaplastic lymphoma kinase (ALK). In various in vitro studies, N-[5-(3,5-difluorobenzyl)-1H-indazol-3-yl]-4-(4-methyl-piperazin-1-yl)-2-(tetrahydro-2H-pyran-4-ylamino)-benzamide inhibited proliferation of the CRC cell line KM12, which depends upon TrkA kinase activity for proliferation and survival. It was also potent in inhibiting cell proliferation of ALK-dependent Anaplastic Large Cell Lymphoma cell lines.

In a single-dose food effect study in dogs of N-[5-(3,5-difluorobenzyl)-1H-indazol-3-yl]-4-(4-methyl-piperazin-1-yl)-2-(tetrahydro-2H-pyran-4-ylamino)-benzamide, in a formulation that did not comprise at least one polymer, exposure levels of N-[5-(3,5-difluorobenzyl)-1H-indazol-3-yl]-4-(4-methyl-piperazin-1-yl)-2-(tetrahydro-2H-pyran-4-ylamino)-benzamide in the dogs were approximately 2-fold higher under fed conditions compared to those observed under fasting conditions. Such food effects can cause difficulty during human testing of drugs as the fed or fasted condition of the patient can cause exposure or bioavailability of drugs to vary widely.

In early clinical studies in humans, N-[5-(3,5-difluorobenzyl)-1H-indazol-3-yl]-4-(4-methyl-piperazin-1-yl)-2-(tetrahydro-2H-pyran-4-ylamino)-benzamide has been shown to have antitumor effects in patients having various forms of cancer having at least one molecular alteration in one or more of ALK, ROS1, TrkA, TrkB and TrkC. Alternative formulations of the N-[5-(3,5-difluorobenzyl)-1H-indazol-3-yl]-4-(4-methyl-piperazin-1-yl)-2-(tetrahydro-2H-pyran-4-ylamino)-benzamide are necessary in order to allow flexibility of the dosage form of the compound that can be administered to cancer patients, such as pediatric cancer patients, and exhibit the pharmacokinetics necessary to treat cancer in such cancer patients. It is an object of the present disclosure to provide pharmaceutical compositions and dosage forms comprising N-[5-(3,5-difluorobenzyl)-1H-indazol-3-yl]-4-(4-methyl-piperazin-1-yl)-2-(tetrahydro-2H-pyran-4-ylamino)-benzamide that permit flexibility of the dosage forms that are administered to cancer patients and exhibit the pharmacokinetic properties necessary to treat cancer in cancer patients.

SUMMARY

In some embodiments are provided a pharmaceutical composition, comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer.

In some embodiments are provided a pharmaceutical composition, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is substantially amorphous.

In some embodiments are provided a method of inhibiting at least one of ALK, ROS1, TrkA, TrkB, or TrkC kinase activity in a subject in need thereof, comprising administering to said subject a therapeutically effective amount of a pharmaceutical composition comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer.

In some embodiments are provided a method of treating cancer in a subject, the method comprising: (1) testing one or more cells comprising the cancer in said subject for the presence of at least one of ALK, ROS1, TrkA, TrkB, or TrkC kinase; and (2) administering to the subject a therapeutically effective amount of a pharmaceutical composition comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, if said one or more cells tests positive for at least one of ALK, ROS1, TrkA, TrkB, or TrkC kinase.

In some embodiments are provided a method of treating cancer in a subject, comprising (a) acquiring knowledge of the presence of at least one genetic alteration in at least one target gene in said subject, wherein the at least one target gene is selected from ALK1, BDNF, NGF, NGFR, NTF3, NTF4, ROS1, SORT1, NTRK1, NTRK2, and NTRK3; and (b) selecting a pharmaceutical composition comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, as a treatment for said subject, based on the recognition that said pharmaceutical composition is effective in treating the subject having said at least one genetic alteration in said at least one target gene; and (c) administering a therapeutically effective amount of said pharmaceutical composition to said subject.

In some embodiments are provided pharmaceutical compositions comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer in the form of a granules, a powder, liquid suspension, tablet or capsule. In some embodiments are provided pharmaceutical compositions in the form of a granule, a powder, liquid suspension, or capsule.

In some embodiments are provided pharmaceutical compositions comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition comprises from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide.

BRIEF DESCRIPTION OF THE DRAWINGS

FIG. 1 shows the stability data of various solutions comprising N-[5-(3,5-difluorobenzyl)-1H-indazol-3-yl]-4-(4-methyl-piperazin-1-yl)-2-(tetrahydro-pyran-4-ylamino)-benzamide from Example 2.

FIG. 2 shows the particle size analysis results from Example 4.

DETAILED DESCRIPTION

Figure 3:
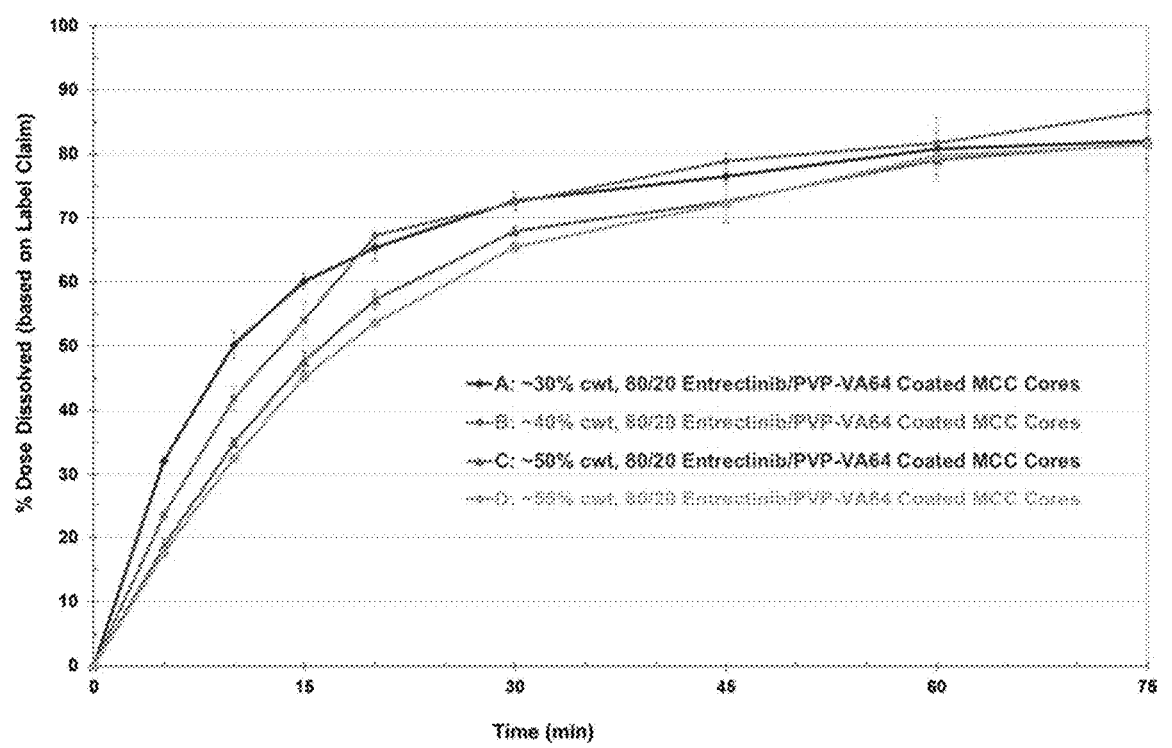
FIG. 3 shows the dissolution performance of formulations from Example 4.

The singular form "a," "an," and "the" include plural references unless the context clearly dictates otherwise. For example, the term "a cell" includes one or more cells, including mixtures thereof. "A and/or B" is used herein to include all of the following alternatives: "A," "B," "A or B," and "A and B."

As used herein, the term "N-[5-(3,5-difluorobenzyl)-1H-indazol-3-yl]-4-(4-methyl-piperazin-1-yl)-2-(tetrahydro-pyran-4-ylamino)-benzamide" means a compound having Chemical Abstracts Service Registry No. 1108743-60-7 and having the chemical structure:

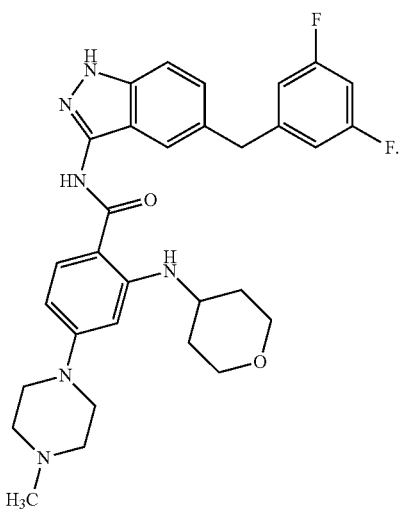 [SMILES: CN1CCN(c2ccc(C(=O)Nc3n[nH]c4ccc(Cc5cc(F)cc(F)c5)cc34)c(NC3CCOCC3)c2)CC1]

Hereinafter all references to N-[5-(3,5-difluorobenzyl)-1H-indazol-3-yl]-4-(4-methyl-piperazin-1-yl)-2-(tetrahydro-pyran-4-ylamino)-benzamide herein include references to solvates, complexes, polymorphic forms, stereoisomers, and isotopically labeled versions thereof. Also included within the scope provided herein are pharmaceutical compositions comprising solvates, complexes, polymorphic forms, stereoisomers, and isotopically labeled versions of N-[5-(3,5-difluorobenzyl)-1H-indazol-3-yl]-4-(4-methyl-piperazin-1-yl)-2-(tetrahydro-pyran-4-ylamino)-benzamide.

As used herein, the term "about" means either within plus or minus 10% of the provided value, or rounded to the nearest significant figure, in all cases inclusive of the provided value. Where ranges are provided, they are inclusive of the boundary values.

As used herein, the terms "administration" and "administering" mean the delivery of a bioactive composition or formulation to a subject by an administration route including, but not limited to, oral, intravenous, intra-arterial, intramuscular, intraperitoneal, subcutaneous, intramuscular, topically, or combinations thereof. In some embodiments, the administration to a subject is oral.

As used herein, the term "admixture" means a mixture of one or more chemical compounds in a composition. It is understood by one having ordinary skill in the art that the pharmaceutical compositions disclosed herein may comprise an admixture of N-[5-(3,5-difluorobenzyl)-1H-indazol-3-yl]-4-(4-methyl-piperazin-1-yl)-2-(tetrahydro-pyran-4-ylamino)-benzamide and the at least one polymer.

As used herein, the term "ALK" means anaplastic lymphoma kinase receptor or CD246 (cluster of differentiation 246), which is an enzyme that in humans is encoded by the ALK gene and also has the UniProt identified ALK_HUMAN.

As used herein, the term "amorphous" means a solid material that does not have long-range three-dimensional translational order. One of ordinary skill in the art may refer to amorphous material as being non-crystalline. The term is intended to include material which may have some small degree of order, but the order is in less than three dimensions and/or is only over short distances. Partially crystalline materials, liquid crystals, and disordered crystals are included as well. Amorphous material may be characterized by techniques known to those having ordinary skill in the art, including, but not limited to, powder x-ray diffraction (PXRD) crystallography, solid state nuclear magnetic resonance (NMR), or thermal techniques such as differential scanning calorimetry (DSC). For example, when evaluated by PXRD, amorphous or non-crystalline materials may exhibit a deviation from a flat baseline, referred to by those of ordinary skill in the art as an amorphous halo. In another example, when evaluated by DSC, amorphous or non-crystalline material will exhibit a glass-transition temperature ($T_g$).

As used herein, the term "crystalline" refers to solid material in which atoms or molecules are arranged in a definite pattern that is repeated regularly in three dimensions.

As used herein, the term "antibody" means an immunoglobulin that specifically binds to, and is thereby defined as complementary with, a particular spatial and polar organization of another molecule. The antibody can be monoclonal or polyclonal and can be prepared by techniques that are well known in the art, such as immunization of a host and collection of sera (polyclonal), or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular target is maintained.

As used herein, the term "AUC" means the area under the curve of a plot of the concentration of a compound in the plasma of a subject versus time.

As used herein, the term "biological sample," means a sample obtained from an organism that may be used in a diagnostic or monitoring assay. The sample may be of a healthy tissue, diseased tissue or tissue suspected of being diseased tissue. The sample may be a biopsy taken, for example, during a surgical procedure. The sample may be collected via means of fine needle aspiration, scraping or washing a cavity to collects cells or tissue therefrom. The sample may be of a tumor such as, for example, solid and hematopoietic tumors as well as of neighboring healthy tissue. The sample may be a smear of subject cells or a tissue section. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses clinical samples, and also includes cells in cell culture, cell supernatants, cell lysates, cell extracts, cell homogenates, and subcellular components including synthesized proteins, serum, plasma, bodily and other biological fluids, and tissue samples. The biological sample can contain compounds that are not naturally intermixed with the cell or tissue in nature such as preservatives, anticoagulants, buffers, fixatives, nutrients, antibiotics or the like. In some embodiments, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

As used herein, the term "biomarker" means one or more compounds whose level of nucleic acid or protein product has a quantitatively differential concentration or level with respect to an aspect of a biological state of a subject. The term "biomarker" may be used herein interchangeably with the term "marker." The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present disclosure include those associated with ALK, ROS1, TrkA, TrkB, and TrkC.

As used herein, the term "$C_{max}$" means the peak concentration that a compound achieves in the plasma of a subject after the compound, or a pharmaceutical composition comprising the compound, has been administrated to the subject. In some embodiments, the compound, or a pharmaceutical composition comprising the compound, is administered orally to a subject to achieve a particular $C_{max}$.

As used herein, the terms "cancer" or "tumor" may be used interchangeably. These terms mean the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion. The terms also refer to solid tumors named for the type of cells that form them, cancer of blood, bone marrow, or the lymphatic system. Examples of solid tumors include, but are not limited to, sarcomas and carcinomas. Examples of cancers of the blood include, but are not limited to, leukemias, lymphomas and myeloma. The terms include, but are not limited to, a primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of different type from latter one. As used herein "cancer" refers to any malignant and/or invasive growth or tumor caused by abnormal cell growth.

As used herein, the term "chemotherapeutic agent", means a chemical substance, such as a cytotoxic or cytostatic agent, that is used to treat a condition, particularly cancer.

As used herein, the terms "combination" and "in combination with" mean the administration of N-[5-(3,5-difluorobenzyl)-1H-indazol-3-yl]-4-(4-methyl-piperazin-1-yl)-2-(tetrahydro-pyran-4-ylamino)-benzamide together with at least one additional pharmaceutical or medicinal agent (e.g., an anti-cancer agent), either sequentially or simultaneously. It includes dosing simultaneously, or within minutes or hours of each other, or on the same day, or on alternating days, or dosing the pharmaceutical compositions provided herein on a daily basis, or multiple days per week, or weekly basis, for example, while administering another compound such as a chemotherapeutic agent on the same day or alternating days or weeks or on a periodic basis during a time simultaneous therewith or concurrent therewith, or at least a part of the time during which the pharmaceutical compositions disclosed herein is dosed. For example, a pharmaceutical composition as provided herein that comprises N-[5-(3,5-difluorobenzyl)-1H-indazol-3-yl]-4-(4-methyl-piperazin-1-yl)-2-(tetrahydro-pyran-4-ylamino)-benzamide could be dosed every day or several days a week while the chemotherapeutic agent is dosed on alternating days or alternating weeks or other periods of time, such as every 1, 2, 3, 4, 5, 6, 7, 8, 9, 10, 11, 12, 13, 14 or more days.

As used herein, the term "contact" when used in reference to specificity or specific binding means two molecules are close enough so that short range non-covalent chemical interactions, such as Van der Waal forces, hydrogen bonding, hydrophobic interactions, and the like, dominate the interaction of the molecule.

As used herein, the term "cell line" means to one or more generations of cells which are derived from a clonal cell. The term "clone," or "clonal cell," means a single cell which is expanded to produce an isolated population of phenotypically similar cells (i.e. a "clonal cell population").

As used herein, the parameters Dv10, Dv50, Dv90 and Dv99 represent the particle size at the 10%, 50%, 90% and 99% points of the cumulative number or volume undersize particle size distribution. Thus, a "Dv10" for a material represents a particle size wherein 10% of the number or volume of the material consists of particles having a particle size equal to the Dv100 value or smaller. A "Dv50" for a material represents a particle size wherein 50% of the number of volume of the material consists of particles having a particle size equal to the Dv50 value or smaller. A "Dv90" for a material represents a particle size wherein 90% of the number or volume of the material consists of particles having a particle size equal to the Dv90 value or smaller. A "Dv99" for a material represents a particle size wherein 99% of the number or volume of the material consists of particles having a particle size equal to the Dv99 value or smaller.

As used herein, the term "food effect" means a change in the rate and/or extent of absorption of a compound in a subject when the compound is administered to the subject shortly after a meal (fed conditions) as compared to the rate and/or extent of absorption of the compound when the compound is administered to the subject under fasting conditions. As used herein, the term "no food effect" means that there is no significant difference in the rate and/or extent of absorption of a compound in a subject when the compound is administered to the subject in fed conditions compared to fasting conditions.

As used herein, the term "immunohistochemistry," means the process of localizing antigens (e.g. proteins) in biological samples, cells and/or cells of a tissue section exploiting the principle of antibodies binding specifically to antigens. Immunohistochemical staining is widely used in the diagnosis of abnormal cells such as those found in cancerous tumors. Specific molecular markers are characteristic of particular cellular events, such as cell proliferation or cell death. Visualizing an antibody-antigen interaction can be accomplished in a number of ways. In the most common instance, an antibody is conjugated to an enzyme, such as peroxidase, that can catalyze a color-producing reaction. Alternatively, the antibody can also be tagged to a fluorophore thus employing the principles of immunofluorescence. Immunohistochemistry can also be used to evaluate tumor content in the sample on which qPCR is carried out in order to account for the fact that qPCR result will be influenced by the amount of tumor tissue present.

As used herein, the terms "monoclonal antibody," "mAb" and "MAB" mean an antibody that is an immunoglobulin produced by a single clone of lymphocytes which recognizes only a single epitope on an antigen. For example, a monoclonal antibody useful for the methods provided herein displays a single binding specificity and affinity for a particular epitope of one or more tyrosine kinases.

As used herein, the term "multiplexed assay" means an assay in which multiple assay reactions, e.g. simultaneous assays of multiple target biomarkers, are carried out in a single reaction chamber and/or and analyzed in a single separation and detection format.

As used herein, the term "multiplex identification" means the simultaneous identification of one or more target biomarkers in a single mixture. For example, a two-plex assay means the simultaneous identification, in a single reaction mixture, of two different target biomarkers.

As used herein, the term "one or more molecular alterations" means any variation in the genetic or protein sequence in one or more cells of a subject as compared to the corresponding wild-type genes or proteins. One or more molecular alterations include, but are not limited to, genetic mutations, gene amplifications, splice variants, deletions, insertions/deletions, gene rearrangements, single-nucleotide variations (SNVs), insertions, and aberrant RNA/protein expression.

As used herein, the term "particle size distribution" means the relative proportions of particles of a compound having a given particle size. While the particle size of a spherical object can be unambiguously and quantitatively defined by its diameter, particles comprising an active pharmaceutical ingredient or an excipient may be non-spherical and irregular in shape. There are several methods by which those of ordinary skill in the art measure and express the size of non-spherical and irregular particles, such as measuring the size of such particles using laser diffractometry and expressing the size of such particles based on replacing a given particle with an imaginary sphere that has one of a number of properties of the particle. Such properties can be selected from, for example, but are not limited to, the diameter of an imaginary sphere having the same volume of the particle being measured (volume-based particle size), the diameter of an imaginary sphere having the same weight as the particle being measured (weight-based particle size), and the diameter of an imaginary sphere having the same surface area as the particle being measured (area-based particle size). Those having ordinary skill in the art are familiar with such methods, and the manner in which the results of such methods are expressed, and such methods can be applied to the embodiments disclosed herein without undue experimentation. The particle size distribution may be represented, for example, graphically as a plot. A common type of plot is a cumulative undersize plot which represents the fraction (e.g. by number, surface area, volume or mass) of particles that are smaller than the stated particle size.

As used herein, the term "polymer" means a polymeric compound that is capable of preventing, slowing, or reducing the amount of crystalline N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, that is present or is formed in the compositions disclosed herein. The compositions disclosed herein may comprise amorphous N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, or may comprise substantially amorphous N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In the compositions disclosed herein, the polymer and N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may be in an admixture.

As used herein, the term "polyclonal antibody" means a composition of different antibody molecules which is capable of binding to or reacting with several different specific antigenic determinants on the same or on different antigens. The variability in antigen specificity of a polyclonal antibody is located in the variable regions of the subject antibodies constituting the polyclonal antibody, in particular in the complementarity determining regions (CDRs). Preferably, the polyclonal antibody is prepared by immunization of an animal with the target tyrosine kinases or portions thereof. Alternatively, the polyclonal antibody may be prepared by mixing multiple monoclonal antibodies having desired specificity to a target tyrosine kinase.

As used herein, "ROS1" means the ROS1 receptor tyrosine-protein kinase having the UniProt designation ROS1_HUMAN.

As used herein, the term "selectively binds" means the situation in which one member of a specific intra- or inter-species binding pair will not show any significant binding to molecules other than its specific intra- or inter-species binding partner (e.g., an affinity of about 100-fold less), which means that only minimal cross-reactivity occurs.

As used herein in reference to the binding of two molecules or one or more compounds and a complex of molecules, the term "specific" means the specific recognition of one for the other and the formation of a stable complex, as compared to substantially less recognition of other molecules and the lack of formation of stable complexes with such other molecules. Preferably, "specific," in reference to binding, means that to the extent that one or more compounds forms complexes with other molecules or complexes, it forms at least fifty percent of the complexes with the molecule or complex for which it has specificity. Generally, the molecules or complexes have areas on their surfaces or in cavities giving rise to specific recognition between the two binding moieties. Exemplary of specific binding are antibody-antigen interactions, enzyme-substrate interactions, polynucleotide hybridizations and/or formation of duplexes, cellular receptor-ligand interactions, and so forth.

As used herein, the term "solid dispersion" means a system in a solid state comprising at least two components, wherein one component is dispersed in the other component or components. A solid dispersion includes those systems in which one component is evenly or unevenly dispersed in the other component or components.

As used herein, the term "subject" means a mammal, including, but not limited to, a human, a dog or a cat. In some embodiments, the subject is a human. In some embodiments, the subject is a dog. In some embodiments, the subject is a cat.

As used herein, the term "substantially amorphous" means that more than 50% of the amount of the N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, that comprise the compositions disclosed herein, is not in a crystalline form. In some embodiments, less than about 45%, or less than about 40%, or less than about 35%, or less than about 30%, or less than about 25%, or less than about 20%, or less than about 15%, or less than about 10%, or less than about 5%, or less than about 4%, or less than about 3%, or less than about 2%, or less than about 1% of the N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprising the compositions disclosed herein is in crystalline form. The amount of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, that is present in crystalline form in the compositions disclosed herein can be determined according to methods or techniques known to those having ordinary skill in the art, including, but not limited to, powder x-ray diffraction (PXRD) and Raman spectroscopy.

As used herein, the term "$T_{max}$" means the time when the peak concentration of a compound in the plasma of a subject is reached after administration of the compound, or a pharmaceutical composition comprising the compound, to the subject.

As used herein, the term "therapeutically effective amount" means that amount of the compound or compounds, or pharmaceutically acceptable salts thereof, being administered to a subject which will relieve to some extent one or more of the symptoms of the disorder being treated. In reference to the treatment of a cancer, a therapeutically effective amount means that amount which has the effect of (1) reducing the size of a cancer tumor, (2) inhibiting (that is, slowing to some extent, preferably stopping) cancer tumor metastasis, (3) inhibiting to some extent (that is, slowing to some extent, preferably stopping) cancer tumor growth, and/or, (4) relieving to some extent (or, preferably, eliminating) one or more symptoms associated with the cancer.

As used herein, the terms "tropomyosin receptor kinase," "Trks" and "Trk" mean the family of tropomyosin receptor kinases (Trks) that are activated by peptide hormones of the neurotrophin family and include, but are not limited to, TrkA, TrkB, and TrkC. As used herein, the term "TrkA" means wild-type tropomyosin receptor kinase A having the UniProt identifier NTRK1_HUMAN. As used herein, the term "TrkB" means wild-type tropomyosin receptor kinase B having the UniProt identifier NTRK2_HUMAN. As used herein, the term "TrkC" means wild-type tropomyosin receptor kinase C having the UniProt identifier NTRK3_HUMAN. TrkA, TrkB and TrkC are also referred to by those having ordinary skill in the art as Trk1, Trk2 and Trk3, respectively. A reference to TrkA is a reference to Trk1. A reference to TrkB is a reference to Trk2. A reference to TrkC is a reference to Trk3

As used herein, the term "USP Apparatus Type I" means the Apparatus 1 (Basket Apparatus or Basket Method) and the procedures for using the apparatus that are described in United States Pharmacopeia (USP) General Chapter <711>.

As used herein, the term "USP Apparatus Type II" means the Apparatus 2 (Paddle Apparatus or Paddle Method) and the procedures for using the apparatus described in United States Pharmacopeia (USP) General Chapter <711>.

In one aspect are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one polymer.

In one aspect are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, at least one polymer and at least one pharmaceutically acceptable excipient.

In some embodiments are provided a pharmaceutical composition, comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer.

In some embodiments are provided a pharmaceutical composition, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is substantially amorphous.

In some embodiments are provided a pharmaceutical composition, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, wherein at least about 51%, or at least about 60%, or at least about 65%, or at least about 70%, or at least about 80%, or at least about 85%, or at least about 90%, or at least about 95%, or at least about 96%, or at least about 97%, or at least about 97.5%, or at least about 98%, or at least about 98.5%, or at least about 99%, or at least about 99.5% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is amorphous or non-crystalline.

In some embodiments are provided a pharmaceutical compositions described herein comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, wherein at least about 51%, or at least about 60%, or at least about 65%, or at least about 70%, or at least about 80%, or at least about 85%, or at least about 90%, or at least about 95%, or at least about 96%, or at least about 97%, or at least about 97.5%, or at least about 98%, or at least about 98.5%, or at least about 99%, or at least about 99.5% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is amorphous or non-crystalline following storage of said pharmaceutical composition at 50° C. and 75% relative humidity for at least 7 days.

In some embodiments are provided a pharmaceutical compositions described herein comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, wherein at least about 51%, or at least about 60%, or at least about 65%, or at least about 70%, or at least about 80%, or at least about 85%, or at least about 90%, or at least about 95%, or at least about 96%, or at least about 97%, or at least about 97.5%, or at least about 98%, or at least about 98.5%, or at least about 99%, or at least about 99.5% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is amorphous or non-crystalline following storage of said pharmaceutical composition at 40° C. and 75% relative humidity, or 50° C. and 75% relative humidity, for at least 8 days, or at least 9 days, or at least 10 days, or at least 11 days, or at least 12 days, or at least 13 days, or at least 14 days, or at least one month, or at least two months, or at least three months, or at least four months, or at least five months, or at least 6 months, or at least 7 months, or at least 8 months, or at least 9 months, or at least 10 months, or at least 11 months, or at least one year.

In some embodiments are provided any of the pharmaceutical compositions described herein, wherein said at least one polymer is selected from the group consisting of polyvinyl pyrrolidone, polyethyleneoxide, a copolymer of 1-vinyl-2-pyrrolidone and vinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose, hydroxypropyl cellulose, carboxymethyl ethylcellulose, hydroxypropyl methylcellulose acetate succinate, cellulose acetate phthalate, cellulose acetate trimellitate, ethyl cellulose, cellulose acetate, cellulose butyrate, cellulose acetate butyrate, and dextran polymer derivative. In some embodiments are provided any of the pharmaceutical compositions described herein, wherein the at least one polymer is selected at least one copolymer of 1-vinyl-2-pyrrolidone and vinyl acetate. In some embodiments are provided any of the pharmaceutical compositions described herein, wherein the weight to weight ratio of 1-vinyl-2-pyrrolindone to vinyl acetate comprising said copolymer of 1-vinyl-2-pyrrolidone and vinyl acetate is from about 1 to 10 to about 10 to 1. In some embodiments are provided any of the pharmaceutical compositions described herein, wherein the weight to weight ratio of 1-vinyl-2-pyrrolindone to vinyl acetate comprising said copolymer of 1-vinyl-2-pyrrolidone and vinyl acetate is about 1 to 10, or about 1 to 9, or about 1 to 8, or about 1 to 7, or about 1 to 6, or about 1 to 5, or about 1 to 4, or about 1 to 3 or about 1 to 2 or about 1 to 1. In some embodiments are provided any of the pharmaceutical compositions described herein, wherein the weight to weight ratio of 1-vinyl-2-pyrrolindone to vinyl acetate comprising said copolymer of 1-vinyl-2-pyrrolidone and vinyl acetate is about 10 to 1, or about 9 to 1, or about 8 to 1, or about 7 to 1 or about 6 to 1, or about 3 to 2, or about 5 to 1, or about 4 to 1, or about 3 to 1, or about 2 to 1. In some embodiments are provided any of the pharmaceutical compositions described herein wherein the weight to weight ratio of 1-vinyl-2-pyrrolindone to vinyl acetate comprising said copolymer of 1-vinyl-2-pyrrolidone and vinyl acetate is about 3:2, or about 6 to 4.

In some embodiments are provided any of the pharmaceutical compositions described herein, wherein said pharmaceutical composition is in the form of particles. In some embodiments are provided any of the pharmaceutical compositions described herein, wherein the average diameter of said particles is between about 100 micrometers and about 300 micrometers, or between about 100 micrometers and about 275 micrometers, or between about 100 micrometers and about 250 micrometers, or between about 100 micrometers and about 225 micrometers, or between about 100 micrometers and about 200 micrometers, or between about 100 micrometers and about 175 micrometers, or between about 100 micrometers and about 150 micrometers, or between about 100 micrometers and about 125 micrometers, or between about 125 micrometers and about 300 micrometers, or between about 150 micrometers and about 300 micrometers, or between about 175 micrometers and about 300 micrometers, or between about 200 micrometers and about 300 micrometers, or between about 225 micrometers and about 300 micrometers, or between about 250 micrometers and about 300 micrometers, or between about 275 micrometers and about 300 micrometers.

In some embodiments are provided any of the pharmaceutical compositions described herein, wherein said pharmaceutical composition is in the form of particles, and wherein not less than about 50% of said particles have a diameter between about 150 micrometers and about 300 micrometers, or not less than about 60% of said particles have a diameter between about 150 micrometers and about 300 micrometers, or not less than about 70% of said particles have a diameter between about 150 micrometers and about 300 micrometers, not less than about 80% of said particles have a diameter between about 150 micrometers and about 300 micrometers, not less than about 90% of said particles have a diameter between about 150 micrometers and about 300 micrometers, or not less than about 95% of said particles have a diameter between about 150 micrometers and about 300 micrometers.

In some embodiments are provided any of the pharmaceutical compositions described herein, wherein said pharmaceutical composition is in the form of particles, e.g. granules, and wherein not less than about 50% of said particles have a diameter between about 150 micrometers and about 300 micrometers, or between about 100 micrometers and about 275 micrometers, or between about 100 micrometers and about 250 micrometers, or between about 100 micrometers and about 225 micrometers, or between about 100 micrometers and about 200 micrometers, or between about 100 micrometers and about 175 micrometers, or between about 100 micrometers and about 150 micrometers, or between about 100 micrometers and about 125 micrometers, or between about 125 micrometers and 300 micrometers, or between about 150 micrometers and 300 micrometers, or between about 175 micrometers and about 300 micrometers, or between about 200 micrometers and about 300 micrometers, or between about 225 micrometers and about 300 micrometers, or between about 250 micrometers and about 300 micrometers, or between about 275 micrometers and about 300 micrometers In some embodiments are provided any of the pharmaceutical compositions described herein, wherein said pharmaceutical composition is in the form of particles, and wherein not more than about 20% of said particles have a diameter larger than about 2 mm, or about 1.75 mm, or about 1.5 mm, or about 1.25 mm, or about 1 mm, or about 750 micrometers, or about 500 micrometers, or about 300 micrometers, or about 275 micrometers, or about 250 micrometers, or about 225 micrometers, or about 200 micrometers, or about 175 micrometers, or about 150 micrometers, or about 125 micrometers, or about 100 micrometers.

In some embodiments are provided any of the pharmaceutical compositions described herein, wherein said pharmaceutical composition is in the form of particles, and wherein said particles comprise a cellulose core. In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer comprise at least one layer on said cellulose core.

In some embodiments are provided any of the pharmaceutical compositions described herein, wherein said pharmaceutical composition is in the form of particles, and wherein the bulk density of said particles is between about 0.25 g per cubic centimeter and about 1 gram per cubic centimeter, or between about 0.5 g per cubic centimeter and about 1 gram per cubic centimeter, or between about 0.75 g per cubic centimeter and about 1 gram per cubic centimeter.

In some embodiments are provided any of the pharmaceutical compositions described herein, wherein said pharmaceutical composition is in the form of particles, and wherein the bulk density of said particles is about 0.25 g per cubic centimeter, or about 0.5 g per cubic centimeter, or about 0.6 g per cubic centimeter, or about 0.65 g per cubic centimeter, or about 0.7 g per cubic centimeter, or about 0.75 g per cubic centimeter, or about 0.76 g per cubic centimeter, or about 0.8 g per cubic centimeter, or about 0.85 g per cubic centimeter, or about 0.9 g per cubic centimeter, or about 1 g per cubic centimeter.

In some embodiments are provided any of the pharmaceutical compositions described herein, wherein said pharmaceutical composition is in the form of particles, and wherein the tap density of said particles is about 0.25 g per cubic centimeter, or about 0.5 g per cubic centimeter, or about 0.6 g per cubic centimeter, or about 0.65 g per cubic centimeter, or about 0.7 g per cubic centimeter, or about 0.75 g per cubic centimeter, or about 0.76 g per cubic centimeter, or about 0.8 g per cubic centimeter, or about 0.85 g per cubic centimeter, or about 0.9 g per cubic centimeter, or about 1 g per cubic centimeter.

In some embodiments are provided any of the pharmaceutical compositions described herein, wherein said pharmaceutical composition is in the form of particles, and wherein the Carr index of said particles is between about 1 and about 21, or between about 2 and about 21, or between about 3 and about 21, or between about 4 and about 21, or between about 5 and about 21, or between 3 and about 20, or between about 3 and about 19, or between about 3 and about 18, or between about 3 and about 17, or between about 3 and about 16, or between about 4 and about 18, or between about 4 and about 17, or between about 5 and about 15.

In some embodiments are provided any of the pharmaceutical compositions described herein, wherein said pharmaceutical composition is in the form of particles, and wherein the d50 of said particles is between about 50 micrometers and about 500 micrometers, or between about 50 micrometers and 450 micrometers, or between about 50 micrometers and 400 micrometers, or between about 50 micrometers and about 350 micrometers, or between about 100 micrometers and about 500 micrometers, and between about 100 micrometers and about 450 micrometers, or between about 100 micrometers and about 400 micrometers, or between about 100 micrometers and 350 micrometers, or between about 100 micrometers and 300 micrometers, or between about 125 micrometers and about 350 micrometers, or between about 150 micrometers and 350 micrometers, or between about 125 micrometers and about 300 micrometers, or between about 150 micrometers and about 250 micrometers, or between about 150 micrometers and about 225 micrometers, or between about 150 micrometers and about 200 micrometers.

In some embodiments are provided any of the pharmaceutical compositions described herein, wherein said pharmaceutical composition is in the form of particles, and wherein said particles comprise a cellulose core. In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer comprise at least one layer on said cellulose core. In some embodiments are provided any of the pharmaceutical compositions described herein, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, plus said at least one polymer to said cellulose core is from about 1 to 10 to about 10 to 1. In some embodiments are provided any of the pharmaceutical compositions described herein, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, plus said at least one polymer to said cellulose core is about 1 to 9, or about 1 to 8, or about 1 to 7, or about 1 to 6, or about 1 to 5, or about 1 to 4, or about 1 to 3, or about 1 to 2, or about 1 to 1. In some embodiments are provided any of the pharmaceutical compositions described herein, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, plus said at least one polymer to said cellulose core is about 10 to 1, or about 9 to 1, or about 8 to 1, or about 7 to 1, or about 6 to 1, or about 5 to 1, or about 4 to 1, or about 3 to 1, or about 2 to 1. In some embodiments, the weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to polymer, to core is about 4:1:5.

In some embodiments are provided any of the pharmaceutical compositions described herein, and wherein said pharmaceutical composition is in the form of particles, wherein said particles comprise a cellulose core. In some embodiments are provided any of the pharmaceutical compositions described herein, wherein said -[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer comprise at least one layer on said cellulose core, wherein said at least one layer on said cellulose core has a thickness of from about 5 micrometers to about 40 micrometers. In some embodiments are provided any of the pharmaceutical compositions described herein, wherein said at least one layer on said cellulose core has a thickness of from about 5 micrometers to about 35 micrometers, or from about 5 micrometers to about 30 micrometers, or from about 5 micrometers to about 25 micrometers, or from about 5 micrometers to about 20 micrometers, or from about 5 micrometers to about 19 micrometers, or from about 5 micrometers to about 18 micrometers, or from about 5 micrometers to about 17 micrometers, or from about 5 micrometers to about 16 micrometers, or from about 5 micrometers to about 15 micrometers, or from about 5 micrometers to about 14 micrometers, or from about 5 micrometers to about 13 micrometers, or from about 5 micrometers to about 12 micrometers, or from about 5 micrometers to about 11 micrometers, or from about 5 micrometers to about 10 micrometers, or from about 5 micrometers to about 9 micrometers, or from about 5 micrometers to about 8 micrometers, or from about 5 micrometers to about 7 micrometers, or from about 5 micrometers to about 6 micrometers, or from about 6 micrometers to about 25 micrometers, or from about 7 micrometers to about 25 micrometers, or from about 7 micrometers to about 25 micrometers, or from about 8 micrometers to about 25 micrometers, or from about 8 micrometers to about 25 micrometers, or from about 9 micrometers to about 25 micrometers, or from about 8 micrometers to about 25 micrometers, or from about 9 micrometers to about 25 micrometers, or from about 7 micrometers to about 25 micrometers, or from about 8 micrometers to about 25 micrometers, or from about 9 micrometers to about 25 micrometers, or from about 10 micrometers to about 25 micrometers, or from about 11 micrometers to about 25 micrometers, or from about 12 micrometers to about 25 micrometers, or from about 13 micrometers to about 25 micrometers, or from about 14 micrometers to about 25 micrometers, or from about 15 micrometers to about 25 micrometers, or from about 16 micrometers to about 25 micrometers, or from about 17 micrometers to about 25 micrometers, or from about 18 micrometers to about 25 micrometers, or from about 19 micrometers to about 25 micrometers, or from about 20 micrometers to about 25 micrometers.

In some embodiments are provided any of the pharmaceutical compositions described herein, wherein said pharmaceutical composition is in the form of particles, and wherein said particles comprise a cellulose core. In some embodiments are provided any of the pharmaceutical compositions described herein, wherein said -[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer comprise at least one layer on said cellulose core, wherein said at least one layer on said cellulose core has a thickness of about 5 micrometers, or about 6 micrometers, or about 7 micrometers, or about 8 micrometers, or about 9 micrometers, or about 10 micrometers, or about 11 micrometers, or about 12 micrometers, or about 13 micrometers, or about 14 micrometers, or about 15 micrometers, about 16 micrometers, or about 17 micrometers, or about 18 micrometers, or about 19 micrometers, or about 20 micrometers, about 21 micrometers, or about 22 micrometers, or about 23 micrometers, or about 24 micrometers, or about 25 micrometers, or about 26 micrometers, or about 27 micrometers, or about 27 micrometers, or about 28 micrometers, or about 29 micrometers, or about 30 micrometers.

In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to said at least one polymer is from about 1 to 10 to about 10 to 1. In some embodiments are provided any of the pharmaceutical compositions described herein, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to said at least one polymer is about 1 to 10, or about 1 to 9, or about 1 to 8, or about 1 to 7, or about 1 to 6, or about 1 to 5, or about 1 to 4, or about 1 to 3, or about 1 to 2. In some embodiments are provided any of the pharmaceutical compositions described herein, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to said at least one polymer is about 10 to 1, or about 9 to 1, or about 8 to 1, or about 7 to 1, or about 6 to 1, or about 5 to 1, or about 4 to 1, or about 3 to 1, or about 2 to 1.

In some embodiments are provided any of the pharmaceutical compositions described herein, wherein said pharmaceutical composition releases at least about 25% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 60 minutes in pH 6.5 phosphate buffered saline. In some embodiments are provided any of the pharmaceutical compositions described herein, wherein said pharmaceutical composition releases at least about 20%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95%, of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 60 minutes in pH 6.5 phosphate buffered saline.

In some embodiments are provided any of the pharmaceutical compositions described herein, wherein said pharmaceutical composition releases not less than about 95% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 60 minutes in pH 6.5 phosphate buffered saline. In some embodiments are provided any of the pharmaceutical compositions described herein, wherein said pharmaceutical composition releases not less than about 90%, or not less than about 85%, or not less than about 80%, or not less than about 75%, or not less than about 70%, or not less than about 65%, or not less than about 60%, or not less than about 55%, or not less than about 50%, or not less than about 45%, or not less than about 40%, or not less than about 35%, or not less than about 30%, or not less than about 25%, or not less than about 20%, or not less than about 15%, or not less than about 10%, or not less than about 5% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 60 minutes in pH 6.5 phosphate buffered saline.

In some embodiments are provided any of the pharmaceutical compositions described herein, wherein said pharmaceutical composition releases at least about 10% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 15 minutes in 75 mL of aqueous solution at pH 2. In some embodiments are provided any of the pharmaceutical compositions described herein, wherein said pharmaceutical composition releases at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% of the total amount of said N-[5—(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 15 minutes in 75 mL of aqueous solution at pH 2.

In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprises at least about 5% of the total weight of said composition. In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprises at least about 10%, or at least about 15%, or at least about 20%, or at least about 25%, or at least about 30%, or at least about 35%, or at least about 40%, or at least about 45%, or at least about 50%, or about least 55%, or at least about 60%, or at least about 65%, or at least about 70%, or at least about 75%, or at least about 80%, or at least about 85%, or at least about 90%, or at least about 95% of the total weight of said composition. In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprises at least about 40% of the total weight of said composition In some embodiments, the pharmaceutical compositions comprise particles comprising a cellulose core and the total weight of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprising said pharmaceutical compositions includes the weight of the cellulosic core.

In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said composition comprises from about 1% to about 25% by weight of water. In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said composition comprises from about 1% to about 20%, or from about 1% to about 19%, or from about 1% or from about 18%, or from about 1% to about 17%, or from about 1% to about 16%, or from about 1% to about 15%, or from about 1% to about 14%, or from about 1% to about 13%, or from about 1% to about 12%, or from about 1% to about 11%, or from about 1% to about 10%, or from about 1% to about 9%, or from about 1% to about 8%, or from about 1% to about 7%, or from about 1% to about 6%, or from about 1% to about 5%, or from about 1% to about 4%, or from about 1% to about 3%, or from about 1% to about 2% by weight of water.

In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said composition comprises about 1% by weight of water. In some embodiments are provided any of the pharmaceutical compositions described herein, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said composition comprises about 2%, or about 3%, or about 4%, or about 5%, or about 6%, or about 7%, or about 8%, or about 9%, or about 10%, or about 11%, or about 12%, or about 13%, or about 14%, or about 15%, or about 16%, or about 17%, or about 18%, or about 19%, or about 20% by weight of water.

In some embodiments are provided any of the pharmaceutical compositions described herein, wherein said composition comprises no more than about 10,000 parts per million (ppm) of residual solvent. In some embodiments are provided any of the pharmaceutical compositions described herein, wherein said composition comprises no more than about 9500 ppm, or 9000 ppm, or 8500 ppm, or 8000 ppm, or 7500 ppm, or 7000 ppm, or 6500 ppm, or 6000 ppm, or 5500 ppm, or 5000 ppm, or 4500 ppm, or 4000 ppm, or 3500 ppm, or 3000 ppm, or 2500 ppm, or 2000 ppm, or 1500 ppm, or 1000, or 750 ppm, or 500 ppm, or 400 ppm, or 350 ppm, or 325 ppm, or 300 ppm, or 275 ppm, or 250 ppm, or 225 ppm, or 200 ppm, or 175 ppm, or 150 ppm, or 125 ppm, or 100 ppm, or 75 ppm, or 50 ppm, or 25 ppm, or 20 ppm, or 18 ppm, or 17 ppm, or 16 ppm, or 15 ppm, or 14 ppm, or 13 ppm, or 12 ppm, or 11 ppm, or 10 ppm, or 9 ppm, or 8 ppm, or 7 ppm, or 6 ppm or 5 ppm, or 4 ppm, or 3 ppm, or 2 ppm, or 1 ppm.

In some embodiments are provided any of the pharmaceutical compositions described herein, wherein said composition comprises from about 1 ppm to about 10,000 ppm of residual solvent. In some embodiments are provided any of the pharmaceutical compositions described herein, wherein said composition comprises from about 1 ppm to about 9,500 ppm, or from about 1 ppm to about 9000 ppm of residual solvent, or from about 1 ppm to about 8500 ppm of residual solvent, or from about 1 ppm to about 8000 ppm of residual solvent, or from about 1 ppm to about 7500 ppm of residual solvent, or from about 1 ppm to about 7000 ppm of residual solvent, or from about 1 ppm to about 6500 ppm of residual solvent, or from about 1 ppm to about 6000 ppm of residual solvent, or from about 1 ppm to about 5500 ppm of residual solvent, or from about 1 ppm to about 5000 ppm of residual solvent, or from about 1 ppm to about 4500 ppm of residual solvent, or from about 1 ppm to about 4000 ppm of residual solvent, or from about 1 ppm to about 3500 ppm of residual solvent, or from about 1 ppm to about 3000 ppm of residual solvent, or from about 200 ppm to about 9000 ppm of residual solvent, or from about 300 ppm to about 9000 ppm of residual solvent, or from about 400 ppm to about 9000 ppm of residual solvent, or from about 500 ppm to about 7500 ppm of residual solvent, or from about 500 ppm to about 6500 ppm of residual solvent, or from about 500 ppm to about 6000 ppm of residual solvent, or from about 500 ppm to about 5500 ppm of residual solvent, or from about 750 ppm to about 7500 ppm of residual solvent, or from about 750 ppm to about 7000 ppm of residual solvent, or from about 750 ppm to about 6500 ppm of residual solvent, or from about 10 ppm to about 5000 ppm, or from about 1 ppm to about 4000 ppm, or from about 1 ppm to about 3000 ppm, or from about 1 ppm to about 2000 ppm, or from about 1 ppm to about 1000 ppm, or from about 1 ppm to about 750 ppm, or from about 1 ppm to about 500 ppm, or from about 1 ppm to about 400 ppm, or from about 1 ppm to about 300 ppm, or from about 1 ppm to about 200 ppm, or from about 1 ppm to about 100 ppm, or from about 1 ppm to about 50 ppm, or less than 1 ppm.

In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is substantially amorphous following storage of said pharmaceutical composition at 50° C. and 75% relative humidity for at least 7 days. In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is substantially amorphous following storage of said pharmaceutical composition at 50° C. and 75% relative humidity for at least 8 days, or at least 9 days, or at least 10 days, or at least 11 days, or at least 12 days, or at least 13 days, or at least 14 days, or at least one month, or at least two months, or at least three months, or at least four months, or at least five months, or at least 6 months, or at least 7 months, or at least 8 months, or at least 9 months, or at least 10 months, or at least 11 months, or at least one year.

In some embodiments are provided any of the pharmaceutical compositions described herein, wherein said composition comprises no more than about 1%, or no more than about 0.8%, or no more than about 0.75%, or no more than about 0.7%, or no more than about 0.65%, or no more than about 0.6%, or no more than about 0.55%, or no more than about 0.5%, or no more than about 0.45%, or no more than about 0.4%, or no more than about 0.35%, or no more than about 0.3%, or no more than about 0.25%, or no more than about 0.2%, or no more than about 0.15%, or no more than about 0.1%, or no more than about 0.05%, or no more than about 0.01% by weight of residual solvent.

In some embodiments are provided any of the pharmaceutical compositions described herein, wherein said pharmaceutical composition releases at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 70%, or at least about 75%, or at least about 80%, or at least about 85%, or at least about 90%, or at least about 95%, or at least about 97.5% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprising said pharmaceutical composition after about 30 minutes in a USP apparatus II (paddles) containing 75 mL of phosphate buffered saline, wherein said phosphate buffered saline has pH 6.5, is at a temperature of 37° C., and is stirred at 250 rpm.

In some embodiments are provided any of the pharmaceutical compositions described herein, wherein said pharmaceutical composition has a dissolution profile wherein at least about 20%, or at least about 30%, or at least about 35%, or at least about 40%, or at least about 45%, or at least about 50%, or at least about 55%, or at least about 60%, or at least about 65%, or at least about 70%, or at least about 70%, or at least about 75%, or at least about 80%, or at least about 85%, or at least about 90%, or at least about 95%, or at least about 97.5% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 30 minutes when tested in USP Apparatus Type II (paddles) at 250 rpm in 75 mL of phosphate buffered saline at a pH of 6.5 and at about 37° C.

In some embodiments are provided any of the pharmaceutical compositions described herein, wherein said pharmaceutical composition is in the form of a granules, a powder, tablet or capsule. In some embodiments are provided any of the pharmaceutical compositions described herein, wherein said pharmaceutical composition is in the form of a granules. In some embodiments are provided any of the pharmaceutical compositions described herein, wherein said pharmaceutical composition is in the form of a powder. In some embodiments are provided any of the pharmaceutical compositions described herein, wherein said pharmaceutical composition is in the form of a tablet. In some embodiments are provided any of the pharmaceutical compositions described herein, wherein said pharmaceutical composition is in the form of a capsule.

In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer are in an admixture.

In some embodiments are provided any of the pharmaceutical compositions described herein, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer are in an admixture and form a solid dispersion.

In some embodiments are provided a method of inhibiting at least one of ALK, ROS1, TrkA, TrkB, or TrkC kinase activity in a subject in need thereof, comprising administering to said subject a therapeutically effective amount of a pharmaceutical composition comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer in the form of a granules, powder, tablet or capsule. In some embodiments are provided pharmaceutical compositions in the form of a granule, a powder or a capsule.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition comprises from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one polymer, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, degrades in said pharmaceutical composition after said pharmaceutical composition is stored for 3 months in an open container at 40° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one polymer, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is present in said pharmaceutical composition after said pharmaceutical composition is stored for 3 months in an open container at 40° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide and at least one polymer, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, degrades in said pharmaceutical composition after said pharmaceutical composition is stored for 3 months in an open container at 60° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said compositions are non-hygroscopic.

In some embodiments are provided pharmaceutical compositions comprising N-[5-(3,5-difluorobenzyl)-1H-indazol-3-yl]-4-(4-methyl-piperazin-1-yl)-2—(tetrahydro-pyran-4-ylamino)-benzamide, or a pharmaceutically acceptable salt thereof, and at least one polymer, wherein said pharmaceutical composition has a dissolution profile wherein at least about 30% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said tablet or capsule at about 60 minutes when tested in USP Apparatus Type I Basket Method at 50 rpm in 500 mL of sodium acetate buffer at a pH of 4.5 and at about 37° C. In some embodiments are provided such pharmaceutical formulations wherein at least about 40%, or about 50%, or about 60%, or about 70%, or about 80%, or about 90%, or about 95% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 60 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition has a dissolution profile wherein at least about 20% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 45 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition has a dissolution profile wherein at least about 15% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 30 minutes when tested in USP Apparatus Type I Basket Method at 50 rpm in 500 mL of sodium acetate buffer at a pH of 4.5 and at about 37° C.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 2 hours and 6 hours following said administration of said pharmaceutical composition to said subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 2080 nM and about 2110 nM following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between 80% to 125% of 2560 nM, based on a 90 percent confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 28,900 nM*hr and about 30,800 nM*hr following said administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 2080 nM and about 2100 nM following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 28,900 nM*hr and about 30,800 nM*hr following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 2 hours and about 6 hours following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to a subject that exhibits no food effect.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering said N-[5-(3,5-difluorobenzyl)-1H-indazol-3-yl]-4-(4-methyl-piperazin-1-yl)-2-(tetrahydropyran-4-ylamino)-benzamide, or a pharmaceutically acceptable salt thereof, to a subject that exhibits no significant food effect.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition exhibits no food effect when administered to a subject.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition exhibits no food effect when administered to a subject and said subject is also administered one or more proton pump inhibitor compounds.

In one aspect are provided pharmaceutical compositions comprising an admixture of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, at least one polymer and at least one pharmaceutically acceptable excipient.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer. In some embodiments, the formulations comprise from about 10 mg to about 1000 mg, or from about 25 mg to about 1000 mg, or from about 50 mg to about 1000 mg, or from about 100 mg to about 1000 mg, or from about 100 mg to about 800 mg, or from about 100 mg to about 750 mg, or from about 100 mg to about 500 mg, or from about 100 mg to about 300 mg, or from about 100 mg to about 250 mg, or from about 100 mg to about 200 mg, or from about 100 mg to 150 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 25 mg, or about 50 mg, or about 75 mg, or about 100 mg, or about 125 mg, or about 150 mg, or about 175 mg, or about 200 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 100 mg, or about 125 mg, or about 150 mg, or about 175 mg, or about 200 mg, or about 225 mg, or about 250 mg, or about 275 mg, or about 300 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 150 mg, or about 175 mg, or about 200 mg, or about 225 mg, or about 250 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 100 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 150 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 200 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 250 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 300 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 350 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 400 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 450 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise about 500 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

The embodiments of the pharmaceutical compositions provided herein are in a form suitable for oral administration, such as a granule, a powder, tablet or capsule, sustained release formulations, solution suspension, suspension or emulsion. In some embodiments, the pharmaceutical compositions are in the form of a tablet or capsule. In some embodiments, the pharmaceutical compositions are in the form of a tablet. In some embodiments, the tablet is a multi-layer tablet. In some embodiments, the tablet is a multi-layer tablet wherein one or more layers comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, are separate from one or more layers comprising the at least one polymer. In some embodiments, the tablet is a bi-layer tablet wherein a layer comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is separate from a layer comprising the at least one polymer. In some embodiments any of the multi-layer tablets described herein further comprise at least one pharmaceutically acceptable excipient.

In some embodiments, the pharmaceutical compositions are in the form of a tablet, wherein said tablet comprises N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer. In some embodiments, the pharmaceutical compositions are in the form of a tablet, wherein said tablet comprises an admixture of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer. In some embodiments any of the tablets described herein further comprise at least one pharmaceutically acceptable excipient.

In some embodiments, the pharmaceutical compositions are in the form of a tablet, wherein said tablet comprises N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, at least one polymer, and at least one filler. In another embodiment, the tablets further comprise at least one disintegrant. In another embodiment, the tablets further comprise at least one glidant. In another embodiment, the tablets further comprise at least one lubricant. In another embodiment, the tablets further comprise at least one pore-forming agent. In another embodiment, the tablets further comprise at least one binder. In another embodiment, the tablets further comprise at least one gel-forming agent.

In some embodiments, the pharmaceutical compositions are in the form of a capsule. In some embodiments, the capsule is a multi-layer capsule. In some embodiments, the capsule is a multi-layer capsule wherein one or more layers comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, are separate from one or more layers comprising the at least one polymer. In some embodiments, the capsule is a bi-layer capsule wherein a layer comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is separate from a layer comprising the at least one polymer. In some embodiments any of the multi-layer capsules described herein further comprise at least one pharmaceutically acceptable excipient.

In some embodiments, the pharmaceutical compositions are in the form of a capsule, wherein said capsule comprises N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer. In some embodiments, the pharmaceutical compositions are in the form of a capsule, wherein said capsule comprises an admixture of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer. In some embodiments any of the capsules described herein further comprise at least one pharmaceutically acceptable excipient.

In some embodiments, the pharmaceutical compositions are in the form of a capsule, wherein said capsule comprises N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, at least one polymer, and at least one filler. In another embodiment, the capsules further comprise at least one disintegrant. In another embodiment, the capsules further comprise at least one glidant. In another embodiment, the capsules further comprise at least one lubricant.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is present in said pharmaceutical compositions in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg. Furthermore, the pharmaceutical compositions provided herein may contain N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in an amount of about 50 mg, about 100 mg, about 150 mg, about 200 mg, about 250 mg, about 300 mg, about 350 mg, about 400 mg, about 450 mg, or about 500 mg.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is present in said pharmaceutical compositions in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, mannitol, pre-gelatinized starch, colloidal silicon dioxide, and magnesium stearate. In some embodiments, the compositions comprise from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 25 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 50 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 750 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 500 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 300 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 250 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In some embodiments, the compositions comprise from about 100 mg to about 200 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof. In certain embodiments, the compositions comprise about 25 mg, or about 50 mg, or about 75 mg, or about 100 mg, or about 125 mg, or about 150 mg, or about 175 mg, or about 200 mg, or about 225 mg, or about 250 mg, or about 275 mg, or about 300 mg, or about 325 mg, or about 350 mg, or about 375 mg, or about 400 mg, or about 475 mg, or about 500 mg, or about 525 mg, or about 550 mg, or about 575 mg, or about 600 mg, or about 625 mg, or about 650 mg, or about 700 mg, or about 750 mg, or about 800 mg, or about 850 mg, or about 900 mg, or about 950 mg, or about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, degrades in said pharmaceutical composition after said pharmaceutical composition is stored for 3 months in an open container at 40° C. and 75% relative humidity.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide and at least one polymer, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is present in said pharmaceutical composition after said pharmaceutical composition is stored for 3 months in an open container at 40° C. and 75% relative humidity.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein less than about 2% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, degrades in said pharmaceutical composition after said pharmaceutical composition is stored for 3 months in an open container at 60° C. and 75% relative humidity.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein more than about 98% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is present in said pharmaceutical composition after said pharmaceutical composition is stored for 3 months in an open container at 60° C. and 75% relative humidity.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one pharmaceutically acceptable excipient, wherein said pharmaceutical composition is in the form of a tablet or capsule, and wherein said tablet or capsule has a dissolution profile wherein at least about 30%, or at least about 40%, or at least about 50%, or at least about 60%, or at least about 70%, or at least about 75%, or at least about 80%, or at least about 85%, or at least about 90% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said tablet or capsule at about 60 minutes when tested in USP Apparatus Type I Basket Method at 50 rpm in 500 mL of sodium acetate buffer at a pH of 4.5 and at about 37° C. In some embodiments, the pharmaceutical composition further comprises at least one polymer.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition has a dissolution profile wherein at least about 20%, or at least about 30%, or at least about 40%, or at least about 50%, or at least about 60%, or at least about 70% or at least about 75% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 45 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2—(tetrahydro-pyran-4-ylamino)-benzamide, or a pharmaceutically acceptable salt thereof, and at least one polymer, wherein said pharmaceutical composition has a dissolution profile wherein at least about 15%, or at least about 20%, or at least about 30%, or at least about 40%, or at least about 50% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 30 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition has a dissolution profile wherein at least about 10%, or at least about 15%, or at least about 20% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 15 minutes when tested in USP Apparatus Type I Basket Method at 50 rpm in 500 mL of sodium acetate buffer at a pH of 4.5 and at about 37° C.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, at least one polymer and at least one pharmaceutically acceptable excipient. In some embodiments are provided pharmaceutical compositions wherein said at least one pharmaceutically acceptable excipient is selected from diluents, lubricants, binding agents, disintegrating agents, effervescing mixtures, dyestuffs, sweeteners, and wetting agents.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 2 hours and 6 hours following said administration of said pharmaceutical composition to said subject. In some embodiments, the Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is about 5 hours following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fed state provides a pharmacokinetic profile in said subject wherein the Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 5 hours and 12 hours following said administration of said pharmaceutical composition to said subject. In some embodiments, the Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is about 8 hours following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 2080 nM and about 2110 nM following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 2080 nM and about 2560 nM following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between 80% to 125% of 2080 nM, based on a 90 percent confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between 80% to 125% of 2560 nM, based on a 90 percent confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is between about 28,900 nM*hr and about 30,800 nM*hr following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is about 40,400 nM*hr following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fasted state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is within about 80% to about 125% of 30,800 nM*hr at a 90% confidence interval following said administration of said pharmaceutical composition to said subject.

In some embodiments are provided pharmaceutical compositions, comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition when administered to a subject in a fed state at a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide or a pharmaceutically acceptable salt thereof, provides a pharmacokinetic profile in said subject wherein the AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of said subject is within about 80% to about 125% of 40,400 nM*hr at a 90% confidence interval following said administration of said pharmaceutical composition to said subject.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 2080 nM and about 2100 nM following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of about 2560 nM following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 28,900 nM*hr and about 30,800 nM*hr following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of about 40,400 nM*hr following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 2 hours and about 6 hours following administration of said pharmaceutical composition to said subject in a fasted state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Tmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject of between about 5 hours and about 12 hours following administration of said pharmaceutical composition to said subject in a fed state.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject that is between 80% to 125% of 2080 nM, based on a 90 percent confidence interval, following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering a Cmax of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject that is between 80% to 125% of 2560 nM, based on a 90 percent confidence interval, following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject that is between 80% to 125% of 30,800 nM*hr, based on a 90 percent confidence interval, following administration of said pharmaceutical composition to said subject in a fasted state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering an AUC(0 to 24) of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in the plasma of a subject that is between 80% to 125% of 40,400 nM*hr, based on a 90 percent confidence interval, following administration of said pharmaceutical composition to said subject in a fed state, and wherein said composition comprises a total dose of about 800 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions, comprising (a) N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer; and (b) means for delivering said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to a subject that exhibits no food effect.

In some embodiments are provided pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer, wherein said pharmaceutical composition exhibits no food effect when administered to a subject.

It is understood by those having ordinary skill in the art that references made to "pharmaceutical compositions provided herein," and the like, mean those pharmaceutical compositions that are described as embodiments herein. By way of example only, a method of treating a subject having cancer comprising administering to said subject a pharmaceutical composition as provided herein, means a method of treating a subject having cancer comprising administering to said subject any of the compositions described herein that comprise N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In some embodiments are provided pharmaceutical compositions provided herein for use as a medicament. In some embodiments, the medicament is for use in the treatment of abnormal cell growth in a mammal. In some embodiments, the abnormal cell growth is cancer. In some embodiments, the medicament is for use in the treatment of abnormal cell growth mediated by one or more of ALK, ROS1, TrkA, TrkB and TrkC in a mammal. In some embodiments, the medicament is for use in the treatment of abnormal cell growth mediated by at least one molecular alteration in one or more of ALK, ROS1, TrkA, TrkB and TrkC in a mammal. In some embodiments, the medicament is for use in the treatment of abnormal cell growth mediated by at least one molecular alteration in ALK in a mammal. In some embodiments, the medicament is for use in the treatment of abnormal cell growth mediated by at least one molecular alteration in ROS1 in a mammal. In some embodiments, the medicament is for use in the treatment of abnormal cell growth mediated by at least one molecular alteration in TrkA in a mammal. In some embodiments, the medicament is for use in the treatment of abnormal cell growth mediated by at least one molecular alteration in TrkB in a mammal. In some embodiments, the medicament is for use in the treatment of abnormal cell growth mediated by at least one molecular alteration in TrkC in a mammal. In some such embodiments, the molecular alteration is the EML4-ALK fusion protein. In some embodiments, the molecular alteration is the EML4-ALK fusion protein having at least one mutation. In some embodiments, the mutation is L1196M. In some embodiments, the mutation is C1156Y.

In some embodiments are provided methods for the treatment of abnormal cell growth in a mammal comprising administering to a mammal a therapeutically effective amount of one or more pharmaceutical compositions provided herein. In some embodiments, the abnormal cell growth is mediated by at least one molecular alteration in one or more of ALK, ROS1, TrkA, TrkB and TrkC in a mammal. In some embodiments, the abnormal cell growth is mediated by at least one molecular alteration in ALK in a mammal. In some embodiments, the abnormal cell growth is mediated by at least one molecular alteration in ROS1 in a mammal. In some embodiments, the abnormal cell growth is mediated by at least one molecular alteration in TrkA in a mammal. In some embodiments, the abnormal cell growth is mediated by at least one molecular alteration in TrkB in a mammal. In some embodiments, the abnormal cell growth is mediated by at least one molecular alteration in TrkC in a mammal. In some such embodiments, the molecular alteration is the EML4-ALK fusion protein. In some embodiments, the molecular alteration is the EML4-ALK fusion protein having at least one mutation. In some embodiments, the mutation is L1196M. In some embodiments, the mutation is C1156Y.

In some embodiments are provided methods for the treatment of abnormal cell growth in a mammal comprising administering to a mammal an amount of one or more pharmaceutical compositions provided herein, in combination with an amount of an anti-tumor agent, which amounts are together effective in treating said abnormal cell growth. In some embodiments, the anti-tumor agent is selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

In some embodiments are provided one or more pharmaceutical compositions provided herein for use in the treatment of abnormal cell growth in a mammal. In a further aspect, are disclosed the uses of one or more pharmaceutical compositions described herein for the treatment of abnormal cell growth in a mammal.

In yet another aspect, are disclosed uses of one or more pharmaceutical compositions described herein for the preparation of a medicament for the treatment of abnormal cell growth.

In frequent embodiments of the methods and uses described herein, the abnormal cell growth is cancer. In some embodiments, the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

In some embodiments, the cancer is selected from the group consisting of non-small cell lung cancer (NSCLC), squamous cell carcinoma, hormone-refractory prostate cancer, papillary renal cell carcinoma, colorectal adenocarcinoma, neuroblastomas, anaplastic large cell lymphoma (ALCL) and gastric cancer.

In some embodiments, the methods described herein further comprise administering to the mammal an amount of an anti-cancer therapeutic agent or a palliative agent, which amounts are together effective in treating said abnormal cell growth. In some such embodiments, one or more anti-cancer therapeutic agent are selected from anti-tumor agents, anti-angiogenesis agents, signal transduction inhibitors and anti-proliferative agents, which amounts are together effective in treating said abnormal cell growth.

In other embodiments, the uses described herein comprise the use of one or more pharmaceutical compositions provided herein in combination with one or more substances selected from anti-tumor agents, anti-angiogenesis agents, signal transduction inhibitors and antiproliferative agents.

In some embodiments, the pharmaceutical compositions described herein are adapted for use in combination with one or more substances selected from anti-tumor agents, anti-angiogenesis agents, signal transduction inhibitors and anti-proliferative agents.

Each of the embodiments of the pharmaceutical compositions provided herein can be combined with one or more other embodiments of the pharmaceutical compositions described herein that is not inconsistent with the embodiment(s) with which it is combined.

In addition, each of the embodiments provided herein envisions within its scope that the pharmaceutical compositions described herein may comprise N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt of N-[5-(3,5-difluorobenzyl)-1H-indazol-3-yl]-4-(4-methyl-piperazin-1-yl)-2-(tetrahydro-2H-pyran-4-ylamino)-benzamide.

In an embodiment is provided a method of inhibiting at least one of ALK, ROS1, TrkA, TrkB, or TrkC kinase activity in a subject in need thereof, comprising administering to said subject a therapeutically effective amount of any of the pharmaceutical compositions disclosed herein.

In an embodiment is provided a method of treating cancer in a subject in need thereof, the method comprising inhibiting ALK, ROS1, TrkA, TrkB, or TrkC activity, or a combination thereof, in said subject, by administering to said subject a therapeutically effective amount of any of the pharmaceutical compositions disclosed herein.

In an embodiment is provided a method of treating cancer in a subject in need thereof, comprising administering to said subject a therapeutically effective amount of any of the pharmaceutical compositions disclosed herein.

In an embodiment is provided a method of treating cancer in a subject in need thereof, wherein one or more cells comprising said cancer in said subject have been determined to comprise at least one gene rearrangement comprising the gene, or a fragment thereof, that expresses at least one of ALK, ROS1, TrkA, TrkB, or TrkC kinase, comprising administering to said subject a therapeutically effective amount of any of the pharmaceutical composition disclosed herein.

In an embodiment is provided a method of treating cancer in a subject, the method comprising: (1) testing one or more cells comprising the cancer in said subject for the presence of at least one of ALK, ROS1, TrkA, TrkB, or TrkC kinase; and (2) administering to the subject a therapeutically effective amount of any of the pharmaceutical compositions disclosed herein if said one or more cells tests positive for at least one of ALK, ROS1, TrkA, TrkB, or TrkC kinase.

In an embodiment is provided a method of treating cancer in a subject, wherein one or more cancerous cells in said subject express at least one of ALK, ROS1, TrkA, TrkB, or TrkC kinase, the method comprising administering to the subject an effective amount of any of the pharmaceutical compositions disclosed herein.

In an embodiment is provided a method of treating a subject having cancer, wherein tumors from said subject are ALK, ROS1, TrkA, TrkB, or TrkC positive, the method comprising administering to the subject a therapeutically effective amount of any of the pharmaceutical compositions disclosed herein.

In an embodiment is provided a method of treating cancer in a subject, comprising (a) acquiring knowledge of the presence of at least one genetic alteration in at least one target gene in said subject, wherein the at least one target gene is selected from ALK1, BDNF, NGF, NGFR, NTF3, NTF4, ROS1, SORT1, NTRK1, NTRK2, and NTRK3; and (b) selecting a pharmaceutical composition disclosed herein as a treatment for said subject, based on the recognition that said pharmaceutical composition is effective in treating the subject having said at least one genetic alteration in said at least one target gene; and (c) administering a therapeutically effective amount of said pharmaceutical composition to said subject.

In an embodiment is provided a method of treating a cancer in a subject, comprising administering to said subject a therapeutically effective amount of any pharmaceutical composition disclosed herein, wherein prior to said administration of said pharmaceutical composition, said subject is known to possess at least one genetic alteration in at least one target gene selected from ALK1, BDNF, NGF, NGFR, NTF3, NTF4, ROS1, SORT1, NTRK1, NTRK2, and NTRK3.

In an embodiment is provided a method of treating cancer in a subject, wherein said subject is known to possess at least one genetic alteration in at least one target gene, comprising administering to said subject a therapeutically effective amount of any pharmaceutical composition disclosed herein, and wherein said target gene is selected from ALK1, BDNF, NGF, NGFR, NTF3, NTF4, ROS1, SORT1, NTRK1, NTRK2, and NTRK3.

In an embodiment is provided any of methods disclosed herein, wherein said cancer is selected from anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, papillary thyroid cancer, or any combination thereof. In an embodiment is provided a method, wherein said cancer is non-small cell lung cancer. In an embodiment is provided a method, wherein said cancer is papillary thyroid cancer. In an embodiment is provided a method, wherein said cancer is neuroblastoma. In an embodiment is provided a method, wherein said cancer is pancreatic cancer. In an embodiment is provided a method, wherein said cancer is colorectal cancer.

In some embodiments are provided any of the pharmaceutical compositions disclosed herein, wherein said composition comprises from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

In an embodiment is provided a method for treating cancer in a subject, comprising:

(a) acquiring knowledge of the presence of one or more molecular alterations in a biological sample from said subject, wherein said one or more molecular alterations comprises one or more mutations in one or more receptor tyrosine kinase polypeptides, wherein the one or more receptor tyrosine kinase polypeptide is selected from TrkA, TrkB, TrkC, ALK and ROS1; and (b) administering a therapeutically effective amount of any of the pharmaceutical compositions disclosed herein. In an embodiment is provided a method, wherein said one or more amino acid substitutions is at a position corresponding to amino acid residue G595 of the TrkA polypeptide. In an embodiment is provided a method, wherein said one or more amino acid substitutions is a Glu-to-Arg substitution (G595R). In an embodiment is provided a method, wherein said one or more amino acid substitutions is at a position corresponding to amino acid residue G667 of the TrkA polypeptide. In an embodiment is provided a method, wherein said one or more amino acid substitutions is a Glu-to-Cys substitution (G667C). In an embodiment is provided a method, wherein said one or more amino acid substitutions is at a position corresponding to amino acid residue G639 of the TrkB polypeptide. In an embodiment is provided a method, wherein said one or more amino acid substitutions is a Glu-to-Arg substitution (G639R). In an embodiment is provided a method, wherein said one or more amino acid substitutions is at a position corresponding to amino acid residue G709 of the TrkB polypeptide. In an embodiment is provided a method, wherein said one or more amino acid substitutions is a Glu-to-Cys substitution (G709C). In an embodiment is provided a method, wherein said one or more amino acid substitutions is at a position corresponding to amino acid residue G623 of the TrkC polypeptide. In an embodiment is provided a method, wherein said one or more amino acid substitutions is a Glu-to-Arg substitution (G623R). In an embodiment is provided a method, wherein said one or more amino acid substitutions is at a position corresponding to amino acid residue G696 of the TrkC polypeptide. In an embodiment is provided a method, wherein said one or more amino acid substitutions is a Glu-to-Cys substitution (G696C).

In an embodiment is provided a method for treating cancer in a subject, comprising (a) identifying a subject having one or more mutations at an amino acid position in a biological sample from said subject, said one or more mutations selected from:

(i) G595 and G667 of the TrkA polypeptide set forth in SEQ ID NO: 1;

(ii) G639 and G709 of the TrkB polypeptide set forth in SEQ ID NO: 3;

(iii) G623 and G696 of the TrkC polypeptide set forth in SEQ ID NO: 5;

(iv) G1202 and 1269 of the ALK polypeptide set forth in SEQ ID NO: 7; and (v) G2032 and 2101 of the ROS1 polypeptide set forth in SEQ ID NO: 9; and (b) administering a therapeutically effective amount of any pharmaceutical composition disclosed herein said subject.

In an embodiment are provided any of the methods disclosed herein, wherein said biological sample comprises sputum, bronchoalveolar lavage, pleural effusion, tissue, whole blood, serum, plasma, buccal scrape, saliva, cerebrospinal fluid, urine, stool, circulating tumor cells, circulating nucleic acids, bone marrow, or any combination thereof.

In an embodiment is provided any of the methods of treatment disclosed herein, wherein said subject receives from about 50 mg to about 1200 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, on a daily basis, or every other day, or every third day, or every fourth day, or every fifth day, or every sixth day, or every week.

In an embodiment is provided any of the methods of treatment disclosed herein, wherein any of the pharmaceutical compositions disclosed herein are administered to a subject in need thereof once per day, or twice per day, or three times per day, or four times per day, or five times per day.

In an embodiment is provided a method of preparing any of the pharmaceutical compositions disclosed herein, comprising:

(a) dissolving a mixture of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer in a solvent to form a solution; and (b) spraying said solution to form particles. In an embodiment is provided a method, wherein said particles are formed into a dosage form. In an embodiment is provided a method, wherein said dosage form is in the form of a granule, a powder, tablet or capsule. In an embodiment is provided a method, wherein said pharmaceutical composition is in the form of a granule. In an embodiment is provided a method, wherein said pharmaceutical composition is in the form of a powder. In an embodiment is provided a method, wherein said pharmaceutical composition is in the form of a tablet. In an embodiment is provided a method, wherein said pharmaceutical composition is in the form of a capsule. In some embodiments are provided the method, wherein said at least one polymer is selected from the group consisting of polyvinyl pyrrolidone, polyethyleneoxide, a copolymer of 1-vinyl-2-pyrrolidone and vinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose, hydroxypropyl cellulose, carboxymethyl ethylcellulose, hydroxypropyl methylcellulose acetate succinate, cellulose acetate phthalate, cellulose acetate trimellitate, ethyl cellulose, cellulose acetate, cellulose butyrate, cellulose acetate butyrate, and dextran polymer derivative. In some embodiments are provided the method, wherein the at least one polymer is selected at least one copolymer of 1-vinyl-2-pyrrolidone and vinyl acetate. In some embodiments are provided the method, wherein the weight to weight ratio of 1-vinyl-2-pyrrolindone to vinyl acetate comprising said copolymer of 1-vinyl-2-pyrrolidone and vinyl acetate is from about 1 to 10 to about 10 to 1. In some embodiments are provided the method, wherein the weight to weight ratio of 1-vinyl-2-pyrrolindone to vinyl acetate comprising said copolymer of 1-vinyl-2-pyrrolidone and vinyl acetate is about 1 to 10, or about 1 to 9, or about 1 to 8, or about 1 to 7, or about 1 to 6, or about 1 to 5, or about 1 to 4, or about 1 to 3 or about 1 to 2 or about 1 to 1. In some embodiments are provided the method, wherein the weight to weight ratio of 1-vinyl-2-pyrrolindone to vinyl acetate comprising said copolymer of 1-vinyl-2-pyrrolidone and vinyl acetate is about 10 to 1, or about 9 to 1, or about 8 to 1, or about 7 to 1 or about 6 to 1, or about 3 to 2, or about 5 to 1, or about 4 to 1, or about 3 to 1, or about 2 to 1. In some embodiments are provided the method, wherein the weight to weight ratio of 1-vinyl-2-pyrrolindone to vinyl acetate comprising said copolymer of 1-vinyl-2-pyrrolidone and vinyl acetate is about 3:2, or about 6 to 4. In some embodiments are provided the method, wherein the solvent comprises one or more ketones. In some embodiments are provided the method, wherein the solvent comprises one or more ketones and water. In some embodiments are provided the method, wherein the solvent comprises one or more ketones and water in a ratio of from about 10 to 1 to about 1 to 10. In some embodiments are provided the method, wherein the solvent comprises one or more ketones and water in a ratio of about 10:1, or about 9.5:1 or about 9:1, or about 8.5:1, or about 8:1, or about 7.5:1, or about 7:1, or about 6.5:1, or about 6:1, or about 5.5:1, or about 5:1, or about 4.5:1, or about 4:1, or about 3.5:1, or about 3:1, or about 2.5:1, or about 2:1, or about 1.5:1, or about 1:1. In some embodiments are provided the method, wherein the solvent comprises one or more ketones and water in a ratio of about 1:10, or about 1:9.5, or about 1:9, or about 1:8.5; or about 1:8, or about 1:7.5; or about 1:7, or about 1:6.5; or about 1:6, or about 1:5.5, or about 1:5, or about 1:4.5, or about 1:4, or about 1:3.5, or about 1:3, or about 1:2, or about 1:1.5. In some embodiments, the one or more ketones comprises acetone or methyl ethyl ketone. In some embodiments, the one or more ketones comprises acetone. In some embodiments, the one or more ketones comprises methyl ethyl ketone.

In an embodiment is provided a method of preparing any of the pharmaceutical compositions disclosed herein, comprising:

(a) dissolving a mixture of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer in a solvent to form a solution; and (b) spraying said solution onto a core to form particles. In an embodiment, the core comprises a cellulosic core. In an embodiment, the particles are further dried to remove residual solvent. In an embodiment is provided a method, wherein said particles are formed into a dosage form. In an embodiment is provided a method, wherein said dosage form is in the form of a granule, a powder, tablet or capsule. In an embodiment is provided a method, wherein said pharmaceutical composition is in the form of a granule. In an embodiment is provided a method, wherein said pharmaceutical composition is in the form of a powder. In an embodiment is provided a method, wherein said pharmaceutical composition is in the form of a tablet. In an embodiment is provided a method, wherein said pharmaceutical composition is in the form of a capsule. In some embodiments are provided the method, wherein said at least one polymer is selected from the group consisting of polyvinyl pyrrolidone, polyethyleneoxide, a copolymer of 1-vinyl-2-pyrrolidone and vinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose, hydroxypropyl cellulose, carboxymethyl ethylcellulose, hydroxypropyl methylcellulose acetate succinate, cellulose acetate phthalate, cellulose acetate trimellitate, ethyl cellulose, cellulose acetate, cellulose butyrate, cellulose acetate butyrate, and dextran polymer derivative. In some embodiments are provided the method, wherein the at least one polymer is selected at least one copolymer of 1-vinyl-2-pyrrolidone and vinyl acetate. In some embodiments are provided the method, wherein the weight to weight ratio of 1-vinyl-2-pyrrolindone to vinyl acetate comprising said copolymer of 1-vinyl-2-pyrrolidone and vinyl acetate is from about 1 to 10 to about 10 to 1. In some embodiments are provided the method, wherein the weight to weight ratio of 1-vinyl-2-pyrrolindone to vinyl acetate comprising said copolymer of 1-vinyl-2-pyrrolidone and vinyl acetate is about 1 to 10, or about 1 to 9, or about 1 to 8, or about 1 to 7, or about 1 to 6, or about 1 to 5, or about 1 to 4, or about 1 to 3 or about 1 to 2 or about 1 to 1. In some embodiments are provided the method, wherein the weight to weight ratio of 1-vinyl-2-pyrrolindone to vinyl acetate comprising said copolymer of 1-vinyl-2-pyrrolidone and vinyl acetate is about 10 to 1, or about 9 to 1, or about 8 to 1, or about 7 to 1 or about 6 to 1, or about 3 to 2, or about 5 to 1, or about 4 to 1, or about 3 to 1, or about 2 to 1. In some embodiments are provided the method, wherein the weight to weight ratio of 1-vinyl-2-pyrrolindone to vinyl acetate comprising said copolymer of 1-vinyl-2-pyrrolidone and vinyl acetate is about 3:2, or about 6 to 4. In some embodiments are provided the method, wherein the solvent comprises one or more ketones. In some embodiments are provided the method, wherein the solvent comprises one or more ketones and water. In some embodiments are provided the method, wherein the solvent comprises one or more ketones and water in a ratio of from about 10 to 1 to about 1 to 10. In some embodiments are provided the method, wherein the solvent comprises one or more ketones and water in a ratio of about 10:1, or about 9.5:1 or about 9:1, or about 8.5:1, or about 8:1, or about 7.5:1, or about 7:1, or about 6.5:1, or about 6:1, or about 5.5:1, or about 5:1, or about 4.5:1, or about 4:1, or about 3.5:1, or about 3:1, or about 2.5:1, or about 2:1, or about 1.5:1, or about 1:1. In some embodiments are provided the method, wherein the solvent comprises one or more ketones and water in a ratio of about 1:10, or about 1:9.5, or about 1:9, or about 1:8.5; or about 1:8, or about 1:7.5; or about 1:7, or about 1:6.5; or about 1:6, or about 1:5.5, or about 1:5, or about 1:4.5, or about 1:4, or about 1:3.5, or about 1:3, or about 1:2, or about 1:1.5. In some embodiments, the one or more ketones comprises acetone or methyl ethyl ketone. In some embodiments, the one or more ketones comprises acetone. In some embodiments, the one or more ketones comprises methyl ethyl ketone.

In some embodiments are provided methods for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, weel kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of one or more pharmaceutical compositions provided herein.

In some embodiments are provided methods to treat a disease caused by and/or associated with dysregulated protein kinase activity selected from the group consisting of cancer and cell proliferative disorders.

In some embodiments are provided methods to treat specific types of cancer comprising carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epitheloid hemangioendothelioma, astrocytoma, meningioma, angiosarcoma, epitheloid hemangiothelioma, keratocanthomas, thyroid follicular cancer, Kaposi's sarcoma, and pancreatic cancer.

In some embodiments are provided methods to treat specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, pancreatic cancer, neuroblastoma, and medulloblastoma.

In some embodiments are provided methods to treat ALK+ anaplastic large cell lymphomas (ALCL) and possibly other indications in which the ALK activity might play a role, like neuroblastoma, rhabdomyosarcoma, glioblastoma, inflammatory myofibroblastic tumor, and some kind of melanomas, breast carcinomas, Ewings sarcomas, retinoblastomas and non-small cell lung carcinomas (NSCLC).

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering one or more pharmaceutical compositions provided herein.

In some embodiments, methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject one or more pharmaceutical compositions provided herein.

In some embodiments are provided methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject one or more pharmaceutical compositions provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 activity in a cell extract from a pancreatic cancerous or precancerous cell population.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering one or more pharmaceutical compositions provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering one or more pharmaceutical compositions provided herein.

In some embodiments are provided methods to treat, reduce the symptoms of, ameliorate the symptoms of, delay the onset of, or otherwise pharmaceutically address pancreatic cancer in a subject, and possibly other indications in such subject in which a defect in the modulation of ROS1, TrkA, TrkB, or TrkC activity, or a combination thereof, activity, or upregulation, misregulation or deletion thereof might play a role by administering to the subject one or more of the pharmaceutical compositions provided herein.

In some embodiments are provided methods to treat, reduce the symptoms of, ameliorate the symptoms of, delay the onset of, or otherwise pharmaceutically address pancreatic cancer in a subject, which cancer is associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject one or more pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or upregulation, misregulation or deletion thereof might play a role by administering to the subject one or more of the pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering to the subject one or more of the pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject one or more pharmaceutical compositions provided herein.

In some embodiments are provided methods to treat, reduce the symptoms of, ameliorate the symptoms of, delay the onset of, or otherwise pharmaceutically address a condition in a subject selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in an subject, and administering to the subject one or more of the pharmaceutical compositions provided herein.

In some embodiments are provided methods to treat cell proliferative disorders such as, but not restricted to, benign prostate hyperplasia, familial adenomatosis polyposis, neuro-fibromatosis, psoriasis, atherosclerosis and conditions involving vascular smooth muscle proliferation or neointimal formation such as restenosis following angioplasty or surgery, pulmonary fibrosis, arthritis, glomerulonephritis, retinopathies comprising diabetic and neonatal retinopathies and age related macular degeneration, graft vessel disease, such as can occur following vessel or organ transplantation, acromegaly and disorders secondary to acromegaly as well as other hypertrophic conditions in which IGF/IGF-1R signaling is implicated, such as fibrotic lung disease, pathologies related to chronic or acute oxidative stress or hyperoxia induced tissue damage, and metabolic disorders in which elevated IGF levels or IGF-1R activity are implicated, such as obesity.

In some embodiments are provided methods of affecting tumor angiogenesis and metastasis inhibition.

In some embodiments, the methods provided herein further comprise subjecting the mammal in need thereof to a radiation therapy or chemotherapy regimen in combination with at least one cytostatic or cytotoxic agent. In some embodiments, the methods provided herein further comprise inhibiting the activity ALK protein which comprises contacting the said protein with an effective amount of one or more pharmaceutical compositions provided herein.

In some embodiments, the methods provided herein for inhibiting at least one of ALK, ROS1, TrkA, TrkB, or TrkC kinase activity, or a combination thereof, in a cell, comprising contacting said cell with an effective amount of one or more pharmaceutical compositions provided herein.

In some embodiments are provided pharmaceutical compositions comprising one or more pharmaceutical compositions provided herein and a pharmaceutically acceptable excipient, carrier or diluent.

Some embodiments provide methods of inhibiting ALK, ROS1, TrkA, TrkB, or TrkC activity, or a combination thereof, in a subject, comprising administering to said subject an effective amount of one or more pharmaceutical compositions provided herein.

Some embodiments provide methods of treating cancer in a subject in need thereof, the method comprising inhibiting ALK, ROS1, TrkA, TrkB, or TrkC activity, or a combination thereof, in said subject, by administering to said subject an effective amount of one or more pharmaceutical compositions provided herein.

Some embodiments provide methods of treating non-small cell lung cancer, papillary thyroid cancer, neuroblastoma, pancreatic cancer or colorectal cancer in a subject, comprising administering to said subject an effective amount of one or more pharmaceutical compositions provided herein.

Some embodiments provide methods of treating tumors in a subject, said methods comprising administering to the subject an effective amount of one or more pharmaceutical compositions provided herein.

Some embodiments provide methods wherein the tumors are caused by the presence of non-small cell lung cancer, papillary thyroid cancer, neuroblastoma, pancreatic cancer or colorectal cancer in the subject. Some embodiments provide methods wherein one or more of the cells comprising the tumors in the subject test positive for the presence of a gene that expresses at least one of ALK, ROS1, TrkA, TrkB, or TrkC kinase or one or more of the cells comprising the tumors in said subject demonstrates at least one of ALK, ROS1, TrkA, TrkB, or TrkC kinase activity.

Some embodiments provide methods wherein one or more of the cells comprising the tumors in the subject test positive for at least one gene rearrangement comprising the gene, or a fragment thereof, that expresses at least one of ALK, ROS1, TrkA, TrkB, or TrkC kinase. Some embodiments provide such methods wherein the cells test positive for at least one of ROS1, TrkA, TrkB, or TrkC kinases. Some embodiments provide methods wherein the cells test positive for ROS1 kinase. Some embodiments provide methods wherein the cells test positive for at least one of TrkA, TrkB and TrkC kinase. Some embodiments provide methods wherein the cells test positive for TrkA kinase. Some embodiments provide methods wherein the cells test positive for TrkB kinase. Some embodiments provide such methods wherein the cells test positive for TrkC kinase.

Some embodiments provide methods of treating cancer in a subject, the method comprising: (1) testing one or more cells comprising the tumors in the subject for the presence of at least one of ALK, ROS1, TrkA, TrkB, or TrkC kinase; and (2) administering to the subject an effective amount of one or more pharmaceutical compositions provided herein.

Some embodiments provide methods of treating cancer in a subject, the method comprising: (1) testing one or more cells comprising the tumors in the subject for the presence of at least one molecular alteration in ALK, ROS1, TrkA, TrkB, or TrkC kinase; and (2) administering to the subject an effective amount of one or more pharmaceutical compositions provided herein.

Some embodiments provide methods of treating cancer in a subject, wherein one or more cancerous cells in said subject express at least one of ROS1, TrkA, TrkB, or TrkC kinase, the method comprising administering to the subject an effective amount of one or more pharmaceutical compositions provided herein.

Some embodiments provide a method for treating a subject having cancer, wherein tumors from said subject are ROS1, TrkA, TrkB, or TrkC positive, a combination thereof, the method comprising administering to the subject an effective amount of one or more pharmaceutical compositions provided herein.

Some embodiments provide a method of treating a cancer subject, comprising (a) acquiring knowledge of the presence of at least one genetic alteration in at least one target gene in the cancer subject, wherein the at least one target gene is selected from ALK1, BDNF, NGF, NGFR, NTF3, NTF4, ROS1, SORT1, NTRK1, NTRK2, and NTRK3; (b) selecting one or more pharmaceutical compositions provided herein as a treatment for the cancer subject, based on the recognition that said pharmaceutical composition is effective in treating cancer subjects having said at least one genetic alteration in said at least one target gene; and (c) administering a therapeutically effective amount of one or more of said pharmaceutical compositions to said cancer subject.

Some embodiments provide a method of treating a cancer subject, comprising administering to said cancer subject a therapeutically effective amount of one or more pharmaceutical compositions provided herein, wherein prior to said administration of said one or more pharmaceutical compositions said cancer subject is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method of treating a cancer subject, wherein prior to said treatment said subject is known to possess at least one genetic alteration in at least one target gene, comprising administering to said cancer subject a therapeutically effective amount of one or more pharmaceutical compositions provided herein and wherein said at least one target gene is selected from ALK1, BDNF, NGF, NGFR, NTF3, NTF4, ROS1, SORT1, NTRK1, NTRK2, and NTRK3.

Some embodiments provide any of the methods described herein wherein the subject or subject is suffering from cancer and the cancer is selected from at least one of non-small cell lung cancer, papillary thyroid cancer, neuroblastoma, pancreatic cancer and colorectal cancer.

In one aspect, provided herein are methods for treating cancer in a subject, comprising (a) acquiring knowledge of the presence of one or more molecular alterations in a biological sample from the cancer subject, wherein the one or more molecular alterations is detected by an assay comprising one or more antibodies that bind to one or more of ALK, ROS1, TrkA, TrkB, and TrkC biomarkers; (b) selecting a chemotherapeutic agent as a treatment for the cancer subject wherein the assay detects the presence of one or more of molecular alterations, and wherein the selected chemotherapeutic agent is one or more of the pharmaceutical compositions provided herein, or a pharmaceutically acceptable salt thereof; and (c) administering a therapeutically effective amount of the one or more selected chemotherapeutic agents to the cancer subject.

In another aspect, provided herein are methods for selecting a cancer subject who is predicted to respond to the administration of a therapeutic regimen, comprising (a) acquiring knowledge of the presence of one or more molecular alterations in a biological sample from the cancer subject, wherein the one or more molecular alterations is detected by an assay comprising one or more antibodies that bind to one or more of ALK, ROS1, TrkA, TrkB, and TrkC biomarkers; and (b) selecting the subject as predicted to respond to the administration of a therapeutic regimen if the one or more molecular alterations is detected in one or more of the biomarkers, or selecting the subject as predicted to not respond to the administration of a therapeutic regimen if the one or more molecular alterations is not detected in the biomarkers. In the methods according to this aspect of the disclosure, the therapeutic regiment includes administering to the selected subject a therapeutically effective amount of one or more of the pharmaceutical compositions provided herein.

It will be appreciated that the actual dosages N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, will vary according the particular composition formulated, the mode of administration, and the particular site, subject or subject, and disease being treated. Those skilled in the art using conventional dosage-determination tests in view of the experimental data for N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may ascertain optimal dosages for a given set of conditions. For oral administration, an exemplary daily dose generally employed will be from about 0.001 to about 1000 mg/kg, from about 0.1 mg to about 1000 mg of body weight, with courses of treatment repeated at appropriate intervals.

This amount will vary depending upon a variety of factors, comprising but not limited to the characteristics of the pharmaceutical compositions and formulations provided herein (comprising activity, pharmacokinetics, pharmacodynamics, and bioavailability thereof), the physiological condition of the subject treated (comprising age, sex, disease type and stage, general physical condition, responsiveness to a given dosage, and type of medication) or cells, the nature of the pharmaceutically acceptable carrier mg/kg or carriers in the formulation, and the route of administration. Further, an effective or therapeutically effective amount may vary depending on whether the one or more pharmaceutical compositions provided herein is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or subject's response to administration of the one or more pharmaceutical compositions and formulations provided herein and adjusting the dosage accordingly.

In some embodiments, a dose of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may range from about 0.1 mg/kg to about 100 mg/kg or more, depending on the factors mentioned above. In other alternatives, the dosage may range from about 0.1 mg/kg to about 100 mg/kg; or about 1 mg/kg to about 100 mg/kg; or about 5 mg/kg up to about 100 mg/kg. For topical applications such as, for example, treatment of various hair conditions, according to some alternatives provided herein, suitable dosage may range from about 1 mg/kg to about 10 g/kg; or about 10 mg/kg to about 1 g/kg; or about 50 mg/kg up to about 10 g/kg. Additional guidance with regard to this aspect can be found in, for example, Remington: The Science and Practice of Pharmacy, 21st Edition, Univ. of Sciences in Philadelphia (USIP), Lippincott Williams & Wilkins, Philadelphia, Pa., 2005.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, are administered to a subject in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives ranges from about 200 mg/m$^2$ to about 1600 mg/m$^2$, or from about 200 mg/m$^2$ to about 1200 mg/m$^2$, or from about 200 mg/m$^2$ to about 1000 mg/m$^2$, or from about 400 mg/m$^2$ to about 1200 mg/m$^2$, or from about 400 mg/m$^2$ to about 1000 mg/m$^2$, or from about 800 mg/m$^2$ to about 1000 mg/m$^2$, or from about 800 mg/m$^2$ to about 1200 mg/m$^2$, or from about 800 mg/m$^2$ to about 1200 mg/m$^2$, or from about 800 mg/m$^2$ to about 1600 mg/m$^2$.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, are administered to a subject in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 200 mg/m$^2$, about 300 mg/m$^2$, about 400 mg/m$^2$, about 500 mg/m$^2$, about 600 mg/m$^2$, about 700 mg/m$^2$, about 800 mg/m$^2$, about 900 mg/m$^2$, about 1000 mg/m$^2$, about 1100 mg/m$^2$, about 1200 mg/m$^2$, about 1300 mg/m$^2$, about 1400 mg/m$^2$, about 1500 mg/m$^2$, about 1600 mg/m$^2$, about 1700 mg/m$^2$, about 1800 mg/m$^2$, about 1900 mg/m$^2$, or about 2000 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 200 mg/m$^2$, about 300 mg/m$^2$, about 400 mg/m$^2$, about 500 mg/m$^2$, about 600 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 200 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 300 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 400 mg/m$^2$. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 500 mg/m$^2$. In some embodiments, the amount of N-[5-(3,5-difluorobenzyl)-1H-indazol-3-yl]-4-(4-methyl-piperazin-1- yl)-2-(tetrahydro-2H-pyran-4-ylamino)-benzamide, or a pharmaceutically acceptable salt thereof, the subject receives is about 600 mg/m$^2$.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, are administered to a subject in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 200 mg, about 300 mg, about 400 mg, about 500 mg, about 600 mg, about 700 mg, about 800 mg, about 900 mg, or about 1000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 200 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 300 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 400 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 500 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 600 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 700 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 800 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 900 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives is about 1000 mg.

Some embodiments include any of the methods described herein, wherein any of the pharmaceutical compositions provided herein that comprise N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, are administered to a subject once per day in an amount such that the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives per day is about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 200 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 300 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 400 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 500 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 600 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 700 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 800 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 900 mg. In some embodiments, the amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, the subject receives once per day is about 1000 mg.

Those of ordinary skill in the art will understand that with respect to pharmaceutical compositions comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, provided herein the particular pharmaceutical composition, the dosage, and the number of doses given per day to a mammal requiring such treatment, are all choices within the knowledge of one of ordinary skill in the art and can be determined without undue experimentation.

Accordingly, while certain dose and administration regimens are exemplified herein, these examples in no way limit the dose and administration regimen that may be provided to a subject in practicing the presently disclosed methods.

It is to be noted that dosage values may vary with the type and severity of the condition to be alleviated, and may include single or multiple doses. It is to be further understood that for any particular subject, specific dosage regimens should be adjusted over time according to the subject need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. The embodiments provided herein are intended to encompass intra-subject dose-escalation as determined by the skilled artisan. Determining appropriate dosages and regimens for administration of the chemotherapeutic agent are well-known in the relevant art and would be understood to be encompassed by the skilled artisan once provided the teachings provided herein.

Implementations of the methods of the present disclosure can include one or more of the following features. In some embodiments, the selected chemotherapeutic agent one or more of the pharmaceutical compositions provided herein. In some embodiments, the assay includes one or more antibodies that bind to at least two of ALK, ROS1, TrkA, TrkB and TrkC biomarkers. In some embodiments, the one or more molecular alterations detected in the biological sample involve at least two, at least three, or at least four of the biomarkers. In some embodiments, the knowledge of the presence of the one or more molecular alterations in the biological sample is acquired from an assay that includes contacting the biological sample with one or more antibodies or fragments thereof specific for the biomarkers. In some embodiments, the specific antibodies are monoclonal antibodies. In some embodiments, the specific antibodies include at least one of D5F3®, D4D5®, C17F1®, and combinations thereof. In some embodiments, the biological sample is contacted with one or more of the specific antibodies simultaneously. In some embodiments, the biological sample is sequentially contacted with the specific antibodies. In some embodiments, the one or more molecular alterations results in elevated expression of one or more of the ALK, ROS1, TrkA, TrkB, and TrkC biomarkers. In some embodiments, the knowledge of the one or more molecular alterations is acquired from an assay wherein determining whether the expression of one or more biomarker is elevated includes: (a) determining the expression level of the one or more biomarkers in the biological sample; and (b) comparing the determined expression level to a reference expression level. In some embodiments, the knowledge of the one or more molecular alterations is acquired from an antibody-based assay. In some embodiments, the antibody-based assay is selected from the group consisting of ELISA, immunohistochemistry, western blotting, mass spectrometry, flow cytometry, protein-microarray, immunofluorescence, and a multiplex detection assay. In some embodiments, the antibody-based assay includes an immunohistochemistry analysis.

In some embodiments, implementations of the methods provided herein further include acquiring knowledge of a genetic alteration in the cancer of the subject from a second analytical assay prior to the administering step, wherein the second analytical assay is selected from the group consisting of capillary electrophoresis, nucleic acid sequencing, polypeptide sequencing, restriction digestion, nucleic acid amplification-based assays, nucleic acid hybridization assay, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), and a kinase activity assay. In some embodiments, the cancer is cancer is selected from the group consisting of anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, and papillary thyroid cancer. In some embodiments, the knowledge of the one or more molecular alterations is obtained from an assay performed simultaneously on a plurality of biological samples. In some embodiments, the plurality of biological samples includes at least 6, 12, 24, 48, 96, 200, 384, 400, 500, 1000, 1500, or 3000 samples. In some embodiments, the one or more molecular alterations is selected from a genetic mutation, a gene amplification, a gene rearrangement, a single-nucleotide variation (SNV), a deletion, an insertion, an InDel mutation, a single nucleotide point mutation (SNP), an epigenetic alteration, a splicing variant, an RNA/protein overexpression, an aberrant RNA/protein expression, and any combination thereof. In some embodiments, the one or more molecular alterations include an insertion of a heterologous nucleic acid sequence within a coding sequence of a biomarker gene. In some embodiments, the insertion forms a chimeric nucleic acid sequence that encodes a fusion peptide. In some embodiments, the acquiring knowledge of the one or more molecular alterations further includes determining a nucleic acid sequence and/or an amino acid sequence comprising the one or more molecular alterations.

Some embodiments provide a pharmaceutical composition comprising one or more pharmaceutical compositions provided herein in combination with one or more chemotherapeutic agents or radiotherapy, such as radiotherapy as commonly administered to treat, ameliorate the symptoms of, or prevent or delay the onset of cancer. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Some embodiments provide a product or kit comprising one or more pharmaceutical compositions provided herein and one or more chemotherapeutic agents, as a combined preparation for simultaneous, separate or sequential use in anticancer therapy.

Some embodiments provide one or more pharmaceutical compositions as provided herein for use as a medicament.

Some embodiments provide the use of one or more pharmaceutical compositions as provided herein in the manufacture of a medicament with antitumor activity.

Some embodiments include any of the methods described herein, wherein said cancer is selected from non-small cell lung cancer, papillary thyroid cancer, neuroblastoma, pancreatic cancer and colorectal cancer. Some embodiments are any of the methods described herein wherein said cancer is non-small cell lung cancer. Some embodiments include any of the methods described herein, wherein said cancer is said cancer is papillary thyroid cancer. Some embodiments include any of the methods described herein, wherein said cancer is wherein said cancer is neuroblastoma. Some embodiments include any of the methods described herein, wherein said cancer is wherein said cancer is pancreatic cancer. Some embodiments include any of the methods described herein, wherein said cancer is wherein said cancer is colorectal cancer.

The pharmaceutically acceptable carrier may comprise a conventional pharmaceutical carrier or excipient. Suitable pharmaceutical carriers include inert diluents or fillers, glidants, lubricants, water and various organic solvents (such as hydrates and solvates). The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. In some embodiments, the excipient comprises pregelatinized starch. In some embodiments, the pharmaceutical compositions comprise a glidant. In some embodiments, the pharmaceutical compositions comprise colloidal silicon dioxide. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols.

To treat or prevent diseases or conditions mediated by ALK, ROS1, TrkA, TrkB, or TrkC, or a combination thereof, a pharmaceutical composition provided herein is administered by combining a therapeutically effective amount of N-[5-(3,5-difluorobenzyl)-1H-indazol-3-yl]-4-(4-methyl-piperazin-1-yl)-2-(tetrahydro-pyran-4-ylamino)-benzamide and at least one polymer. Optionally, such pharmaceutical compositions may comprise one or more pharmaceutically suitable carriers, which may be selected, for example, from diluents, excipients and auxiliaries that facilitate processing of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may be dissolved in an aqueous solution of an organic or inorganic acid, such as a 0.3 M solution of succinic acid or citric acid. If a soluble salt form is not available, N-[5-(3,5-difluorobenzyl)-1H-indazol-3-yl]-4-(4-methyl-piperazin-1-yl)-2-(tetrahydro-pyran-4-ylamino)-benzamid, or a pharmaceutically acceptable salt thereof, may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, N-[5-(3,5-difluorobenzyl)-1H-indazol-3-yl]-4-(4-methyl-piperazin-1-yl)-2-(tetrahydro-pyran-4-ylamino)-benzamide is dissolved in DMSO and diluted with water. The pharmaceutical composition may also be in the form of a solution of a salt form of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in an appropriate aqueous vehicle such as water or isotonic saline or dextrose solution.

Proper formulation is dependent upon the route of administration selected. For injection, N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may be formulated into aqueous solutions, preferably in physiologically compatible buffers such as Hanks solution, Ringer's solution, or physiological saline buffer. For transmucosal administration, penetrants appropriate to the barrier to be permeated are used in the formulation. Such penetrants are generally known in the art.

For oral administration, N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may be formulated by combining it with pharmaceutically acceptable carriers known in the art. Such carriers enable N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to be formulated as tablets, pills, dragees, capsules, powders, granules, liquids, gels, syrups, slurries, suspensions and the like, for oral ingestion by a subject to be treated. Pharmaceutical preparations for oral use can be obtained using a solid excipient in admixture with N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, optionally grinding the resulting mixture, and processing the mixture of granules after adding suitable auxiliaries, if desired, to obtain tablets or dragee cores. Suitable excipients include: fillers such as sugars, comprising isomalt, lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, microcrystalline cellulose or polyvinylpyrrolidone (PVP). In some embodiments, the filler is mannitol, isomalt, hypromellose (hydroxypropylmethylcellulose), or microcrystalline cellulose. In some embodiments, the filler is mannitol. In some embodiments, the filler is isomalt. In some embodiments, the filler is microcrystalline cellulose. If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings.

Pharmaceutical preparations that can be used orally include push-fit capsules made of gelatin, as well as soft, sealed capsules made of gelatin and a plasticizer, such as glycerol or sorbitol. The push-fit capsules can contain N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in admixture with fillers such as lactose, binders such as starches, and/or lubricants such as talc or magnesium stearate, and, optionally, stabilizers. In soft capsules, N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The pharmaceutical compositions disclosed herein may be prepared by various coating procedures and processes known to those of ordinary skill in the art, such as by fluidized bed coating, including Wurster coating, and rotacoating.

In one embodiment, the pharmaceutical formulations disclosed herein, may be prepared by a solvent-based processes including, but not limited to, wet granulation, extrusion-spheronization, wet milling, spray-coating, and spray-drying. In such methods, the N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, the at least one polymer, and optional excipients may be dissolved in the solvent, suspended in the solvent, wetted by the solvent, or any combination of these. The solvent-based process then forms drug-containing particles comprising the drug, optional excipients, and residual solvent. The solvent-based process may involve removal of a portion of the solvent from the particles.

Solvents suitable for solvent processing are preferably volatile with a boiling point of 150° C. or less. In addition, the solvent should have relatively low toxicity and be pharmaceutically acceptable. Preferred solvents include water; alcohols such as methanol, ethanol, the various isomers of propanol, the various isomers of butanol, 1-pentanol, and 2-methyl-1-propanol; organic acids, such as acetic acid and formic acid; ketones such as acetone, methyl ethyl ketone, methyl iso-butyl ketone, cyclohexanone; esters, such as methyl acetate, ethyl formate, ethyl acetate, propyl acetate, and butyl acetate; ethers, such as dimethyl ether, ethyl ether, tert-butyl-methyl ether, 1,2, dimethoxyethane, 2-ethoxyethanol, 2-methoxyethanol, tetrahydrofuran, methyl tetrahydrofuran, 1,3-dioxolane, and 1,4-dioxane; alkanes, such as butane, pentane, hexane, heptane, cyclohexane, and methylcyclohexane; alkenes, such as pentene, hexene, and cyclohexene; nitriles, such as acetonitrile; alkyl halides, such as methylene chloride, chloroform, dichloroethane, dichloroethene, trichloroethane, and trichloroethylene; aromatics, such as benzene, toluene, xylene, ethylbenzene, anisole, cumene, and chlorobenzene; pyridine; and mixtures thereof. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water. Preferred solvents include acetone, methyl ethyl ketone, methyl isobutyl ketone, methanol, ethanol, the various isomers of propanol, methyl acetate, ethyl acetate, toluene, methylene chloride, tetrahydrofuran, 1,4-dioxane, 1,3-dioxolane, and mixtures thereof. Most preferred solvents include acetone, methanol, ethanol, the various isomers of propanol, ethyl acetate, and mixtures thereof. Mixtures of the above with water may also be used.

In an embodiment, the pharmaceutical formulations disclosed herein may be formed by use of a spray-drying process. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985), the disclosure of which is incorporated herein by reference.

Various types of nozzles can be used to atomize the spray solution, thereby introducing the spray solution into the spray-dry apparatus as a collection of small droplets. Essentially any type of nozzle may be used to spray the solution as long as the droplets that are formed are sufficiently small that they dry sufficiently (due to evaporation of solvent) that they do not stick to or coat the spray-drying apparatus wall.

Although the maximum droplet size varies widely as a function of the size, shape and flow pattern within the spray-dryer, generally droplets should be less than about 500 μm in diameter when they exit the nozzle. Examples of types of nozzles that may be used to form the particles include the two-fluid nozzle, the fountain-type nozzle, the flat fan-type nozzle, the pressure nozzle and the rotary atomizer.

Particles formed in a spray drying process typically have a mean size of less than about 500 μm in diameter, and may be less than about 100 μm in diameter, less than about 50 μm in diameter or even less than about 25 μm in diameter. The particles are also typically of low density, having a bulk specific volume of at least about 1.5 mL/g, and typically at least about 2 mL/g.

In the spray-drying process, the final solvent content of the particles as they leave the spray-drying chamber may be less than about 10 wt %, or less than about 5 wt %, or less than about 4 wt %, or less than about 3 wt %, or less than about 2 wt %, or less than about 1 wt %, or less than about 0.75 wt %, or less than about 0.5 wt %, or less than about 0.25 wt %.

In one embodiment, the pharmaceutical compositions disclosed herein comprise a solid dispersion comprising N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt, and at least one polymer, wherein the dispersion is coated onto a seed core. Such compositions may be prepared by methods known to those of ordinary skill in the art and comprise spraying the solvent-bearing feed solution comprising the N-[5-(3,5- difluorobenzyl)-1H-indazol-3-yl]-4-(4-methyl-piperazin-1-yl)-2-(tetrahydro-pyran-4-ylamino)-benzamide, or a pharmaceutically acceptable salt, and at least one polymer onto seed cores, such as cellulosic cores, such as cores comprising microcrystalline cellulose. The seed cores can be made from any suitable material such as starch, microcrystalline cellulose, sugar or wax, by any known method, such as melt- or spray-congealing, extrusion/spheronization, granulation, spray-drying and the like. The feed solution can be sprayed onto such seed cores using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Wurster coaters or top-sprayers available from Glatt Air Technologies of Ramsey, N.J. and from Niro Pharma Systems of Bubendorf, Switzerland) and rotary granulators (e.g., CF-Granulator, available from Freund Corp). During this process, the seed cores are coated with the feed solution and the solvent is evaporated, resulting in a coating comprising a solid dispersion comprising N-[5-(3, 5-difluorobenzyl)-1H-indazol-3-yl]-4-(4-methyl-piperazin-1-yl)-2-(tetrahydro-pyran-4-ylamino)-benzamide, or a pharmaceutically acceptable salt, and at least one polymer. The resulting particles may then be dried in the secondary drying process.

Particles formed by spraying the solvent-bearing feed solution onto seed cores typically have a mean size after coating of less than about 1000 μm in diameter, and may be less than about 500 μm in diameter, less than about 300 μm in diameter, or even less than about 100 μm in diameter. The particles typically have a bulk specific volume of less than about 5 mL/g, and may be less than about 3 mL/g, or even less than about 2 mL/g.

The pharmaceutical compositions provided herein are useful for the treatment of cancers comprising but not limited to cancers of the: circulatory system, for example, heart (sarcoma [angiosarcoma, fibrosarcoma, rhabdomyosarcoma, liposarcoma], myxoma, rhabdomyoma, fibroma, lipoma and teratoma), mediastinum and pleura, and other intrathoracic organs, vascular tumors and tumor-associated vascular tissue; respiratory tract, for example, nasal cavity and middle ear, accessory sinuses, larynx, trachea, bronchus and lung such as small cell lung cancer (SCLC), non-small cell lung cancer (NSCLC), bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal system, for example, esophagus (squamous cell carcinoma, adenocarcinoma, leiomyosarcoma, lymphoma), stomach (carcinoma, lymphoma, leiomyosarcoma), gastric, pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); genitourinary tract, for example, kidney (adenocarcinoma, Wilm's tumor [nephroblastoma], lymphoma, leukemia), bladder and/or urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); liver, for example, hepatoma (hepatocellular carcinoma), cholangiocarcinoma, hepatoblastoma, angiosarcoma, hepatocellular adenoma, hemangioma, pancreatic endocrine tumors (such as pheochromocytoma, insulinoma, vasoactive intestinal peptide tumor, islet cell tumor and glucagonoma); bone, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; nervous system, for example, neoplasms of the central nervous system (CNS), primary CNS lymphoma, skull cancer (osteoma, hemangioma, granuloma, xanthoma, osteitis deformans), meninges (meningioma, meningiosarcoma, gliomatosis), brain cancer (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); reproductive system, for example, gynecological, uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) and other sites associated with female genital organs; placenta, penis, prostate, testis, and other sites associated with male genital organs; hematologic system, for example, blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; oral cavity, for example, lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx; skin, for example, malignant melanoma, cutaneous melanoma, basal cell carcinoma, squamous cell carcinoma, Karposi's sarcoma, moles dysplastic nevi, lipoma, angioma, dermatofibroma, and keloids; adrenal glands: neuroblastoma; and other tissues comprising connective and soft tissue, retroperitoneum and peritoneum, eye, intraocular melanoma, and adnexa, breast, head or/and neck, anal region, thyroid, parathyroid, adrenal gland and other endocrine glands and related structures, secondary and unspecified malignant neoplasm of lymph nodes, secondary malignant neoplasm of respiratory and digestive systems and secondary malignant neoplasm of other sites.

More specifically, examples of cancer when used herein in connection with pharmaceutical compositions provided herein include cancer selected from lung cancer (NSCLC and SCLC), cancer of the head or neck, ovarian cancer, colon cancer, rectal cancer, prostate cancer, cancer of the anal region, stomach cancer, breast cancer, cancer of the kidney or ureter, renal cell carcinoma, carcinoma of the renal pelvis, neoplasms of the central nervous system (CNS), primary CNS lymphoma, non-Hodgkins's lymphoma, spinal axis tumors, or a combination of one or more of the foregoing cancers.

In some embodiments, the pharmaceutical compositions provided herein are useful for the treatment of cancers, comprising Spitz melanoma, perineural invasion, pulmonary large cell neuroendocrine carcinoma, uterine carcinoma, juvenile breast cancer, nasopharyngeal carcinoma, adenoid cystic cancer, meduallary thyroid cancer, salivary cancer, congenital infantile fibrosarcoma, mesoblastic nephroma, esophageal cancer (squamous), diffuse large B-cell lymphoma, papillary thyroid cancer, and mammary analogue secretory carcinoma.

In some embodiments are provided methods for treating diseases caused by and/or associated with deregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, FLT3, JAK2, IGF-R, ALK, PI3K, wee1 kinase, Src, Abl, Akt, MAPK, ILK, MK-2, IKK-2, Cdc7, Nek, Cdk/cyclin kinase family, more particularly Aurora 2, IGF-1R and ALK activity, and ROS1 activity, and further more particularly ALK activity and/or ROS1 activity, which comprises administering to a mammal in need thereof an effective amount of a pharmaceutical composition provided herein.

In some embodiments disclosed herein are directed to treat a disease caused by and/or associated with dysregulated protein kinase activity selected from the group consisting of cancer and cell proliferative disorders.

In some embodiments are provided methods to treat specific types of cancer comprising carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, angiosarcoma, glioblastoma, holangiocarcinoma, inflammatory myofibroblastic tumor, epitheloid hemangioendothelioma, astrocytoma, meningioma, angiosarcoma, epitheloid hemangiothelioma, keratocanthomas, thyroid follicular cancer, Kaposi's sarcoma, and pancreatic cancer.

Some embodiments disclosed herein are directed to treating specific types of cancer such as, but not restricted to, breast cancer, lung cancer, colorectal cancer, prostate cancer, ovarian cancer, endometrial cancer, gastric cancer, clear cell renal cell carcinoma, invasive ductal carcinoma (breast), uveal melanoma, multiple myeloma, rhabdomyosarcoma, Ewing's sarcoma, Kaposi's sarcoma, pancreatic cancer, and medulloblastoma.

In some embodiments are provided methods of treating ALK+ Anaplastic Large Cell Lymphomas (ALCL) and possibly other indications in which the ALK activity might play a role, like Neuroblastoma, Rhabdomyosarcoma, Glioblastoma, Inflammatory Myofibroblastic Tumor, and some kind of Melanomas, Breast Carcinomas, Ewings sarcomas, Retinoblastomas and Non-Small Cell Lung Carcinomas (NSCLC).

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a by administering a pharmaceutical compositions as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1 activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein.

In some embodiments are provided methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject a pharmaceutical composition as provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC activity in a cell extract from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC transcript accumulation in an RNA population from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments are provided methods to treat, reduce the symptoms of, ameliorate the symptoms of, delay the onset of, or otherwise pharmaceutically address pancreatic cancer and possibly other indications in which a defect in the modulation of ALK, ROS1, TrkA, TrkB, or TrkC activity, or a combination thereof, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein. In some embodiments are provided methods to treat, reduce the symptoms of, ameliorate the symptoms of, delay the onset of, or otherwise pharmaceutically address pancreatic cancer associated with a ROS1 down-regulation defect, for example a null mutation such as a ROS1 deletion by identifying a ROS1 down-regulation defect, for example a null mutation such as a ROS1 deletion in a cancer or precancerous pancreatic cell in an subject, and administering to the subject a pharmaceutical composition as provided herein.

In some embodiments are provided methods to treat, reduce the symptoms of, ameliorate the symptoms of, delay the onset of, or otherwise pharmaceutically address pancreatic cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous pancreatic cell in an subject, and administering to the subject a pharmaceutical composition as provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises assaying for ROS1 transcript accumulation in an RNA population from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC activity in a cell extract from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC transcript accumulation in an RNA population from a pancreatic cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ALK, ROS1, TrkA, TrkB, or TrkC activity, or a combination thereof, or upregulation, misregulation or deletion thereof might play a role by administering pharmaceutical composition as provided herein. In some embodiments are provided methods to treat, reduce the symptoms of, ameliorate the symptoms of, delay the onset of, or otherwise pharmaceutically address pancreatic cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer and possibly other indications in which a defect in the modulation of ROS1, TrkA, TrkB, or TrkC activity, or a combination thereof, activity, or upregulation, misregulation or deletion thereof might play a role by administering a pharmaceutical composition as provided herein.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject a pharmaceutical composition as provided herein. In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ROS1 down-regulation defect, for example a null mutation such as a ROS1 deletion by identifying a ROS1 down-regulation defect, for example a null mutation such as a ROS1 deletion in a cancer or precancerous cell in an subject, and administering to the subject a pharmaceutical composition as provided herein.

In some embodiments are provided methods to treat, reduce the symptoms of, ameliorate the symptoms of, delay the onset of, or otherwise pharmaceutically address a condition selected from non-small cell lung cancer, papillary thyroid cancer, neuroblastoma, pancreatic cancer and colorectal cancer associated with a ALK, ROS1, TrkA, TrkB, or TrkC down-regulation defect, for example a null mutation such as a ALK, ROS1, TrkA, TrkB, or TrkC deletion by identifying a ALK, ROS1, TrkA, TrkB, or TrkC down-regulation defect, for example a null mutation such as a ALK, ROS1, TrkA, TrkB, or TrkC deletion in a cancer or precancerous cell in an subject, and administering to the subject a pharmaceutical composition as provided herein.

In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an subject comprises assaying for ROS1 activity in a cell extract from a pancreatic cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an subject comprises assaying for ROS1 transcript accumulation in an RNA population from a cancerous or precancerous cell population. In some embodiments identifying a ROS1 modulation defect such as an upregulation defect or a down-regulation defect, for example a null mutation such as a ROS1 deletion or a ROS1 chimeric locus encoding a constitutively active ROS1 kinase in a cancer or precancerous cell in an subject comprises determining the nucleic acid sequence such as the genomic deoxyribonucleic acid sequence in a cell or cells or a cell population comprising a cell or cells from a pancreatic cancerous or precancerous cell population.

In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an subject comprises assaying for ALK, ROS1, TrkA, TrkB, or TrkC activity in a cell extract from a cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an subject comprises assaying for ALK, ROS1, TrkA, TrkB, or TrkC transcript accumulation in an RNA population from a cancerous or precancerous cell population. In some embodiments identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous cell in an subject comprises determining the nucleic acid sequence such as the genomic deoxyribonucleic acid sequence in a cell or cells or a cell population comprising a cell or cells from a cancerous or precancerous cell populations.

In some embodiments are provided methods for inhibiting at least one of ALK, ROS1, TrkA, TrkB, or TrkC kinase activity, or a combination thereof, in a cell, comprising contacting said cell with an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. Some embodiments provide methods of inhibiting at least one of ALK, ROS1, TrkA, TrkB, or TrkC kinase activity, or a combination thereof, in a cell, by contacting the cell with an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. Some embodiments provide methods of inhibiting at least one of ALK, ROS1, TrkA, TrkB, or TrkC kinase activity, or a combination thereof, in a cell, comprising contacting said cell with an effective amount of a compound which is N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof. In some embodiments, the N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, is delivered to the cell in the form of a pharmaceutical composition as provided herein.

Some embodiments provide methods of inhibiting ALK, ROS1, TrkA, TrkB, or TrkC activity, or a combination thereof, in a subject, comprising administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide methods of treating cancer in a subject in need thereof, the method comprising inhibiting ALK, ROS1, TrkA, TrkB, or TrkC activity, or a combination thereof, in said subject, by administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide methods of treating non-small cell lung cancer, papillary thyroid cancer, neuroblastoma, pancreatic cancer or colorectal cancer in a subject, comprising administering to said subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide methods of treating tumors in a subject, said methods comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof Some embodiments provide methods wherein the tumors are caused by the presence of non-small cell lung cancer, papillary thyroid cancer, neuroblastoma, pancreatic cancer or colorectal cancer in the subject. Some embodiments provide methods wherein one or more of the cells comprising the tumors in the subject test positive for the presence of a gene that expresses at least one of ALK, ROS1, TrkA, TrkB, or TrkC kinase or one or more of the cells comprising the tumors in said subject demonstrates at least one of ALK, ROS1, TrkA, TrkB, or TrkC kinase activity.

Some embodiments provide methods wherein one or more of the cells comprising the tumors in the subject test positive for at least one gene rearrangement comprising the gene, or a fragment thereof, that expresses at least one of ALK, ROS1, TrkA, TrkB, or TrkC kinase. Some embodiments provide such methods wherein the cells test positive for at least one of ROS1, TrkA, TrkB, or TrkC kinases. Some embodiments provide methods wherein the cells test positive for ROS1 kinase. Some embodiments provide methods wherein the cells test positive for at least one of TrkA, TrkB and TrkC kinase. Some embodiments provide methods wherein the cells test positive for TrkA kinase. Some embodiments provide methods wherein the cells test positive for TrkB kinase. Some embodiments provide such methods wherein the cells test positive for TrkC kinase.

Some embodiments provide methods of treating cancer in a subject, the method comprising: (1) testing one or more cells comprising the tumors in the subject for the presence of at least one of ALK, ROS1, TrkA, TrkB, or TrkC kinase; and (2) administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, if said one or more cells tests positive for at least one of ALK, ROS1, TrkA, TrkB, or TrkC kinase.

Some embodiments provide methods of treating cancer in a subject, the method comprising: (1) testing one or more cells comprising the tumors in the subject for the presence of at least one of ROS1, TrkA, TrkB, or TrkC kinase; and (2) administering to the subject a pharmaceutical formulation as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, if said one or more cells tests positive for at least one of ROS1, TrkA, TrkB, or TrkC kinase.

Some embodiments provide methods of treating cancer in a subject, wherein one or more cancerous cells in said subject express at least one of ROS1, TrkA, TrkB, or TrkC kinase, the method comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide methods of treating cancer in a subject, wherein one or more cancerous cells in said subject express at least one of ROS1, TrkA, TrkB, or TrkC kinase, the method comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide a method for treating a subject having cancer, wherein tumors from said subject are ALK, ROS1, TrkA, TrkB, or TrkC positive, or a combination thereof, the method comprising administering to the subject a pharmaceutical composition as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide a method for treating a subject having ALK, ROS1, TrkA, TrkB, or TrkC positive cancer, or a combination thereof, the method comprising administering to the subject a pharmaceutical formulation as provided herein that comprises an effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide a method of treating a cancer subject, comprising (a) acquiring knowledge of the presence of at least one genetic alteration in at least one target gene in the cancer subject, wherein the at least one target gene is selected from ALK1, BDNF, NGF, NGFR, NTF3, NTF4, ROS1, SORT1, NTRK1, NTRK2, and NTRK3; and (b) administering a pharmaceutical composition as provided herein to said cancer subject, said pharmaceutical composition comprising a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide a method of treating a cancer subject, comprising administering to said cancer subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, wherein prior to said administration of said pharmaceutical composition, said cancer subject is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method of treating cancer in a subject, comprising administering to said cancer subject known to possess at least one genetic alteration in at least one target gene selected from ALK1, BDNF, NGF, NGFR, NTF3, NTF4, ROS1, SORT1, NTRK1, NTRK2, and NTRK3 a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide a method of treating a cancer subject, wherein said cancer subject is known to possess at least one genetic alteration in at least one target gene, comprising administering to said cancer subject a pharmaceutical compositions comprising a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and wherein said target gene is selected from ALK1, BDNF, NGF, NGFR, NTF3, NTF4, ROS1, SORT1, NTRK1, NTRK2, and NTRK3.

Some embodiments provide a method of treating a cancer subject, wherein prior to said treatment said subject is known to possess at least one genetic alteration in at least one target gene, comprising administering to said cancer subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and wherein said target gene is selected from ALK1, BDNF, NGF, NGFR, NTF3, NTF4, ROS1, SORT1, NTRK1, NTRK2, and NTRK3.

Some embodiments provide a method of treating a cancer subject, comprising administering to said cancer subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and wherein prior to said pharmaceutical composition being administered to said subject, said subject is known to possess at least one genetic alteration in at least one target gene selected from ALK1, BDNF, NGF, NGFR, NTF3, NTF4, ROS1, SORT1, NTRK1, NTRK2, and NTRK3.

Some embodiments provide a method for treating a cancer subject, comprising (a) acquiring knowledge of the presence of at least one genetic alteration in at least one target gene selected from ALK1, BDNF, NGF, NGFR, NTF3, NTF4, ROS1, SORT1, NTRK1, NTRK2, and NTRK3; and (b) administering to said subject a pharmaceutical composition as provided herein that comprises a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof.

Some embodiments provide any of the methods described herein wherein the subject or subject is suffering from cancer and the cancer is selected from at least one of non-small cell lung cancer, papillary thyroid cancer, neuroblastoma, pancreatic cancer and colorectal cancer. Some embodiments provide any of the methods described herein wherein the subject or subject is suffering from non-small cell lung cancer. Some embodiments provide any of the methods described herein wherein the subject or subject is suffering from papillary thyroid cancer. Some embodiments provide any of the methods described herein wherein the subject or subject is suffering from neuroblastoma. Some embodiments provide any of the methods described herein wherein the subject or subject is suffering from pancreatic cancer. Some embodiments provide any of the methods described herein wherein the subject or subject is suffering from colorectal cancer.

In some embodiments, the pharmaceutical compositions provided herein may be used in combination with one or more additional anti-cancer agents which are described below. When a combination therapy is used, the one or more additional anti-cancer agents may be administered sequentially or simultaneously with the pharmaceutical compositions provided herein. In some embodiments, the additional anti-cancer agent is administered to a mammal (e.g., a human) prior to administration of the pharmaceutical compositions provided herein. In some embodiments, the additional anti-cancer agent is administered to the mammal after administration of the pharmaceutical compositions provided herein. In some embodiments, the additional anti-cancer agent is administered to the mammal (e.g., a human) simultaneously with the administration of pharmaceutical compositions provided herein.

Some embodiments also relate to pharmaceutical compositions for the treatment of abnormal cell growth in a mammal, comprising a human, which comprises an amount of one or more pharmaceutical compositions provided herein comprising hydrates, solvates and polymorphs of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in combination with one or more (preferably one to three) anti-cancer agents selected from the group consisting of anti-angiogenesis agents and signal transduction inhibitors and a pharmaceutically acceptable carrier, wherein the amounts of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof and the combination anti-cancer agents when taken as a whole is therapeutically effective for treating said abnormal cell growth.

In some embodiments, the anti-cancer agent used in conjunction with the pharmaceutical compositions described herein is an anti-angiogenesis agent (e.g., an agent that stops tumors from developing new blood vessels). Examples of anti-angiogenesis agents include for example VEGF inhibitors, VEGFR inhibitors, TIE-2 inhibitors, PDGFR inhibitors, angiopoetin inhibitors, PKC-beta inhibitors, COX-2 (cyclooxygenase II) inhibitors, integrins (alpha-v/beta-3), MMP-2 (matrix-metalloprotienase 2) inhibitors, and MMP-9 (matrix-metalloproteinase 9) inhibitors. Preferred anti-angiogenesis agents include sunitinib (Sutent®), bevacizumab (Avastin®), axitinib (AG 13736), SU 14813 (Pfizer), and AG 13958 (Pfizer).

Additional anti-angiogenesis agents include vatalanib (CGP 79787), Sorafenib (Nexavar®), pegaptanib octasodium (Macugen®), vandetanib (Zactima®), PF-0337210 (Pfizer), SU 14843 (Pfizer), AZD 2171 (AstraZeneca), ranibizumab (Lucentis®), Neovastat® (AE 941), tetrathiomolybdata (Coprexa®), AMG 706 (Amgen), VEGF Trap (AVE 0005), CEP 7055 (Sanofi-Aventis), XL 880 (Exelixis), telatinib (BAY 57-9352), and CP-868,596 (Pfizer).

Other anti-angiogenesis agents include enzastaurin (LY 317615), midostaurin (CGP 41251), perifosine (KRX 0401), teprenone (Selbex®) and UCN 01 (Kyowa Hakko).

Other examples of anti-angiogenesis agents which can be used in conjunction with one or more pharmaceutical compositions described herein include celecoxib (Celebrex®), parecoxib (Dynastat®), deracoxib (SC 59046), lumiracoxib (Preige®), valdecoxib (Bextra®), rofecoxib (Vioxx®), iguratimod (Careram®), IP 751 (Invedus), SC-58125 (Pharmacia) and etoricoxib (Arcoxia®).

Other anti-angiogenesis agents include exisulind (Aptosyn®), salsalate (Amigesic®), diflunisal (Dolobid®), ibuprofen (Motrin®), ketoprofen (Orudis®) nabumetone (Relafen®), piroxicam (Feldene®), naproxen (Aleve®, Naprosyn®) diclofenac (Voltaren®), indomethacin (Indocin®), sulindac (Clinoril®), tolmetin (Tolectin®), etodolac (Lodine®), ketorolac (Toradol®), and oxaprozin (Daypro®).

Other anti-angiogenesis agents include ABT 510 (Abbott), apratastat (TMI 005), AZD 8955 (AstraZeneca), incyclinide (Metastat®), and PCK 3145 (*Procyon*).

Other anti-angiogenesis agents include acitretin (Neotigason®), plitidepsin (Aplidine®), cilengtide (EMD 121974), combretastatin A4 (CA4P), fenretinide (4 HPR), halofuginone (Tempostatin®), Panzem® (2-methoxyestradiol), PF-03446962 (Pfizer), rebimastat (BMS 275291), catumaxomab (Removab®), lenalidomide (Revlimid®), squalamine (EVIZON®), thalidomide (Thalomid®), Ukrain® (NSC 631570), Vitaxin® (MEDI 522), and zoledronic acid (Zometa®).

In some embodiments, the anti-cancer agent is a so called signal transduction inhibitor (e.g., inhibiting the means by which regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, ALK inhibitors, ROS1 inhibitors, TrkA inhibitors, TrkB inhibitors, TrkC inhibitors, farnesyl protein transferase inhibitors, EGF inhibitor, ErbB-1 (EGFR), ErbB-2, pan erb, IGF1R inhibitors, MEK, c-Kit inhibitors, FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors.

Preferred signal transduction inhibitors include gefitinib (Iressa®), cetuximab (Erbitux®), erlotinib (Tarceva®), trastuzumab (Herceptin®), sunitinib (Sutent®) imatinib (Gleevec®), and PD325901 (Pfizer).

Additional examples of signal transduction inhibitors which may be used in conjunction with one or more pharmaceutical compositions provided herein include BMS 214662 (Bristol-Myers Squibb), lonafarnib (Sarasar®), pelitrexol (AG 2037), matuzumab (EMD 7200), nimotuzumab (TheraCIM h-R3®), panitumumab (Vectibix®), Vandetanib (Zactima®), pazopanib (SB 786034), ALT 110 (Alteris Therapeutics), BIBW 2992 (Boehringer Ingelheim), and Cervene® (TP 38).

Other examples of signal transduction inhibitor include PF-2341066 (Pfizer), PF-299804 (Pfizer), canertinib (CI 1033), pertuzumab (Omnitarg®), Lapatinib (Tycerb®), pelitinib (EKB 569), miltefosine (Miltefosin®), BMS 599626 (Bristol-Myers Squibb), Lapuleucel-T (Neuvenge®), NeuVax® (E75 cancer vaccine), Osidem® (IDM 1), mubritinib (TAK-165), CP-724,714 (Pfizer), panitumumab (Vectibix®), lapatinib (Tycerb®), PF-299804 (Pfizer), pelitinib (EKB 569), and pertuzumab (Omnitarg®).

Other examples of signal transduction inhibitors include ARRY 142886 (Array Biopharm), everolimus (Certican®), zotarolimus (Endeavor®), temsirolimus (Torisel®), AP 23573 (ARIAD), and VX 680 (Vertex).

Additionally, other signal transduction inhibitors include XL 647 (Exelixis), sorafenib (Nexavar®), LE-AON (Georgetown University), and GI-4000 (GlobeImmune).

Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (One Bio), BMS 387032 (Bristol-Myers Squibb), PD 0332991 (Pfizer), AG 024322 (Pfizer), LOXO-101 (Loxo Oncology), crizotinib, and ceritinib.

In some embodiments, the pharmaceutical compositions provided herein are used together with classical antineoplastic agents. Classical antineoplastic agents include but are not limited to hormonal modulators such as hormonal, antihormonal, androgen agonist, androgen antagonist and antiestrogen therapeutic agents, histone deacetylase (HDAC) inhibitors, gene silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor, microtubulin inhibitors, antibiotics, plant derived spindle inhibitors, platinum-coordinated compounds, gene therapeutic agents, antisense oligonucleotides, vascular targeting agents (VTAs), and statins.

Examples of classical antineoplastic agents used in combination therapy with one or more pharmaceutical compositions provided herein optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi)), Selective Estrogen-Receptor Downregulators (SERD's; such as fulvestrant), exemestane (Aromasin), anastrozole (Arimidex), atamestane, fadrozole, letrozole (Femara), gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), bicalutamide (Casodex), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide, tamoxifen, exemestane, anastrozole, fadrozole, formestane, letrozole, and combinations thereof.

Other examples of classical antineoplastic agents used in combination with pharmaceutical compositions provided herein include, but are not limited to, suberolanilide hydroxamic acid (SAHA, Merck Inc./Aton Pharmaceuticals), depsipeptide (FR901228 or FK228), G2M–777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, paclitaxel, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In some embodiments, the pharmaceutical compositions provided herein are used together with dihydrofolate reductase inhibitors (such as methotrexate and NeuTrexin (trimetrexate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda®), cytosine arabinoside, Gemzar® (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents used in combination therapy with one or more pharmaceutical compositions provided herein optionally with one or more other agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta®), DMXAA (Antisoma), ibandronic acid, L-asparaginase, pegaspargase (Oncaspar®), Efaproxiral (Efaproxyn®—radiation therapy)), bexarotene (Targretin®), Tesmilifene (DPPE-enhances efficacy of cytotoxics)), Theratope® (Biomira), Tretinoin (Vesanoid®), tirapazamine (Trizaone®), motexafin gadolinium (Xcytrin®) Cotara® (mAb), and NBI-3001 (Protox Therapeutics), polyglutamate-paclitaxel (Xyotax®) and combinations thereof.

Further examples of classical antineoplastic agents used in combination therapy with one or more pharmaceutical compositions provided herein optionally with one or more other agents include, but are not limited to, as Advexin (ING 201), TNFerade (GeneVec, one or more compounds which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

Some embodiments relate to a method for the treatment of breast cancer in a human in need of such treatment. In some embodiments, the method includes, for example, administering to said human an amount of one or more pharmaceutical compositions provided herein in combination with one or more (preferably one to three) anti-cancer agents selected from the group consisting of trastuzumab, tamoxifen, docetaxel, paclitaxel, capecitabine, gemcitabine, vinorelbine, exemestane, letrozole and anastrozole.

Some embodiments provide a method of treating colorectal cancer in a mammal, such as a human, in need of such treatment, by administering an amount of one or more pharmaceutical compositions provided herein in combination with one or more (preferably one to three) anti-cancer agents. Examples of particular anti-cancer agents include those typically used in adjuvant chemotherapy, such as FOLFOX, a combination of 5-fluorouracil (5-FU) or capecitabine (Xeloda), leucovorin and oxaliplatin (Eloxatin). Further examples of particular anti-cancer agents include those typically used in chemotherapy for metastatic disease, such as FOLFOX or FOLFOX in combination with bevacizumab (Avastin); and FOLFIRI, a combination of 5-FU or capecitabine, leucovorin and irinotecan (Camptosar). Further examples include 17-DMAG, ABX-EFR, AMG-706, AMT-2003, ANX-510 (CoFactor), aplidine (plitidepsin, Aplidin), Aroplatin, axitinib (AG-13736), AZD-0530, AZD-2171, bacillus Calmette-Guerin (BCG), bevacizumab (Avastin), BIO-117, BIO-145, BMS-184476, BMS-275183, BMS-528664, bortezomib (Velcade), C–1311 (Symadex), cantuzumab mertansine, capecitabine (Xeloda), cetuximab (Erbitux), clofarabine (Clofarex), CMD-193, combretastatin, Cotara, CT-2106, CV-247, decitabine (Dacogen), E-7070, E-7820, edotecarin, EMD-273066, enzastaurin (LY-317615) epothilone B (EPO-906), erlotinib (Tarceva), flavopyridol, GCAN-101, gefitinib (Iressa), huA33, huC242-DM4, imatinib (Gleevec), indisulam, ING-1, irinotecan (CPT-11, Camptosar) ISIS 2503, ixabepilone, lapatinib (Tykerb), mapatumumab (HGS-ETR1), MBT-0206, MEDI-522 (Abregrin), Mitomycin, MK-0457 (VX-680), MLN-8054, NB-1011, NGR-TNF, NV-1020, oblimersen (Genasense, G3139), OncoVex, ONYX 015 (CI-1042), oxaliplatin (Eloxatin), panitumumab (ABX-EGF, Vectibix), pelitinib (EKB-569), pemetrexed (Alimta), PD-325901, PF-0337210, PF-2341066, RAD-001 (Everolimus), RAV-12, Resveratrol, Rexin-G, S-1 (TS-1), seliciclib, SN-38 liposome, Sodium stibogluconate (SSG), sorafenib (Nexavar), SU-14813, sunitinib (Sutent), temsirolimus (CCI 779), tetrathiomolybdate, thalomide, TLK-286 (Telcyta), topotecan (Hycamtin), trabectedin (Yondelis), vatalanib (PTK-787), vorinostat (SAHA, Zolinza), WX-UK1, and ZYC300, wherein the amounts of the active agent together with the amounts of the combination anticancer agents are effective in treating colorectal cancer.

Some embodiments provide methods for the treatment of renal cell carcinoma in a human in need of such treatment, comprising administering to said human an amount of pharmaceutical compositions provided herein in combination with one or more (preferably one to three) anti-cancer agents selected from the group consisting of capecitabine (Xeloda), interferon alpha, interleukin-2, bevacizumab (Avastin), gemcitabine (Gemzar), thalidomide, cetuximab (Erbitux), vatalanib (PTK-787), Sutent, AG-13736, SU-11248, Tarceva, Iressa, Lapatinib and Gleevec, wherein the amounts of the active agent together with the amounts of the combination anticancer agents is effective in treating renal cell carcinoma.

Some embodiments provide methods for the treatment of melanoma in a human in need of such treatment, comprising administering to said human an amount of pharmaceutical compositions provided herein, in combination with one or more (preferably one to three) anti-cancer agents selected from the group consisting of interferon alpha, interleukin-2, temozolomide (Temodar), docetaxel (Taxotere), paclitaxel, Dacarbazine (DTIC), carmustine (also known as BCNU), Cisplatin, vinblastine, tamoxifen, PD-325,901, Axitinib, bevacizumab (Avastin), thalidomide, sorafanib, vatalanib (PTK-787), Sutent, CpG-7909, AG-13736, Iressa, Lapatinib and Gleevec, wherein the amounts of the pharmaceutical compositions provided herein together with the amounts of the combination anticancer agents is effective in treating melanoma.

Some embodiments provide methods for the treatment of lung cancer in a human in need of such treatment, comprising administering to said human an amount of one or more pharmaceutical compositions provided herein in combination with one or more (preferably one to three) anti-cancer agents selected from the group consisting of capecitabine (Xeloda), bevacizumab (Avastin), gemcitabine (Gemzar), docetaxel (Taxotere), paclitaxel, premetrexed disodium (Alimta), Tarceva, Iressa, Vinorelbine, Irinotecan, Etoposide, Vinblastine, and Paraplatin (carboplatin), wherein the amounts of the active agent together with the amounts of the combination anticancer agents is effective in treating lung cancer.

The presence of at least one genetic alteration in at least one target gene in a cancer subject, wherein the at least one target gene is selected from ALK1, BDNF, NGF, NGFR, NTF3, NTF4, ROS1, SORT1, NTRK1, NTRK2, and NTRK3 may be detected by use of an assay that includes one or more antibodies that bind to at least two, three, four, or all of ALK, ROS1, TrkA, TrkB and TrkC biomarkers. The one or more molecular alterations detected in the biological sample may involve at least two, at least three, or at least four of the biomarkers. The knowledge of the presence of the one or more molecular alterations in the biological sample may be acquired from an assay that includes contacting the biological sample with one or more antibodies or fragments thereof that are specific for the biomarkers. In some instances, the specific antibodies are monoclonal antibodies.

In some instances, the specific antibodies include at least one of D5F3®, D4D5®, C17F1®, and combinations thereof. In some instances, the biological sample is contacted with one or more of the specific antibodies simultaneously. In some instances, the biological sample is sequentially contacted with the specific antibodies. In some instances, the one or more molecular alterations results in elevated expression of one or more of the ALK, ROS1, TrkA, TrkB, and TrkC biomarkers. In some instances, the knowledge of the one or more molecular alterations is acquired from an assay wherein determining whether the expression of one or more biomarker is elevated includes: (a) determining the expression level of the one or more biomarkers in the biological sample; and (b) comparing the determined expression level to a reference expression level.

As used herein, the term "reference level" refers to known expression level of the target biomarker(s) in a control person or subject. In some instances, the reference expression level is the expression level of the target biomarker(s) in a healthy person or subject. In some instances, the reference expression level is the expression level of the target biomarker(s) in a population of healthy control cells. In some instances, the reference expression level is the expression level of the target biomarker(s) in a control person or subject that has been previously determined to possess one or more molecular alterations. In some instances, the reference expression level is the expression level of the target biomarker(s) in a population of control cells that have been previously determined to possess one or more molecular alterations.

In some instances, the knowledge of the one or more molecular alterations is acquired from an antibody-based assay. The antibody-based assay can generally be any antibody-based assay, and can be, for example, ELISA, immunohistochemistry, western blotting, mass spectrometry, flow cytometry, protein-microarray, immunofluorescence, and a multiplex detection assay. In some instances, the antibody-based assay includes an immunohistochemistry analysis.

In some instances, identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC activity in a cell extract from a pancreatic cancerous or precancerous cell population. In some instances, identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises assaying for ALK, ROS1, TrkA, TrkB, or TrkC transcript accumulation in an RNA population from a pancreatic cancerous or precancerous cell population. In some instances, identifying a ALK, ROS1, TrkA, TrkB, or TrkC modulation defect such as an upregulation defect or a down-regulation defect, for example a null mutation such as a ALK, ROS1, TrkA, TrkB, or TrkC deletion or a ALK, ROS1, TrkA, TrkB, or TrkC chimeric locus encoding a constitutively active ALK, ROS1, TrkA, TrkB, or TrkC kinase in a cancer or precancerous pancreatic cell in an subject comprises determining the nucleic acid sequence such as the genomic deoxyribonucleic acid sequence in a cell or cells or a cell population comprising a cell or cells from a pancreatic cancerous or precancerous cell population.

The term "microarray," as used herein, means an ordered arrangement of array elements (for example, small samples of a biological sample from a subject such as tissue samples) mounted on a solid support capable of binding other molecule species or antibodies. The array elements are arranged so that there are preferably at least one or more different array elements.

The term "solid support," as used herein, means the well-understood solid materials to which various components such as, for example, proteins and nucleic acids, are physically attached, thereby immobilizing the components. The term "solid support," as used herein, means a non-liquid substance. A solid support can be, but is not limited to, a membrane, sheet, gel, glass, plastic or metal. Immobilized components may be associated with a solid support by covalent bonds and/or via non-covalent attractive forces such as hydrogen bond interactions, hydrophobic attractive forces and ionic forces, for example.

In some instances, the microarrays suitable for the methods provided herein have a density of at least 1, 2, 4, 6, 8, 10 spots/cm$^2$, preferably at least 10, 20, 30, 40, 50, 60, 70, 80, 90, 100, 110, 120, 130, 140, 150, 160, 170, 180, 190, 200, more preferably at least 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000 spots/cm$^2$.

In some instances, it is contemplated that the spots on the array may each represent a different species of biomarkers or that the multiple spots on the array may represent the same species of biomarkers. In some instances, the spots each represent an array element of differing identity or characteristics.

In some instances, implementations of the methods according to this and other aspects of the present disclosure further include acquiring knowledge of a genetic alteration in the cancer of the subject from a second analytical assay prior to the administering step. The second analytical assay can generally be any analytical assay known to those having ordinary skill in the art, and can be for example an antibody-based assay, a nucleotide-based assay, or an enzymatic activity assay. Non-limiting examples of suitable second analytical assays include capillary electrophoresis, nucleic acid sequencing, polypeptide sequencing, restriction digestion, nucleic acid amplification-based assays, nucleic acid hybridization assay, comparative genomic hybridization, real-time PCR, quantitative reverse transcription PCR (qRT-PCR), PCR-RFLP assay, HPLC, mass-spectrometric genotyping, fluorescent in-situ hybridization (FISH), next generation sequencing (NGS), and a kinase activity assay. Other examples of suitable second analytical assays include ELISA, immunohistochemistry, Western blotting, mass spectrometry, flow cytometry, protein-microarray, immunofluorescence, and multiplex detection assay.

In some instances, FISH analysis is used to identify the chromosomal rearrangement resulting in the one or more molecular alterations such as the fusion genes or gene products as described herein. For example, to perform FISH, at least a first probe tagged with a first detectable label can be designed to target a first gene of a fusion gene, such as in one or more exons of the gene and at least a second probe tagged with a second detectable label can be designed to target a second gene of the fusion gene, such as in one or more exons of the genes (for example, the exons containing the part of the protein that includes the tyrosine kinase domain). The at least one first probe and the at least one second probe will be closer together in a subject who carries the fusion compared to a subject who does not carry the fusion gene or gene product. In some instances, a variation of a FISH assay, for example, "break-apart FISH", is used to evaluate a subject selected by a method provided herein. By this method, at least one probe targeting the fusion junction and at least one probe targeting a subject gene of the fusion, e.g., at one or more exons and or introns of the gene, are utilized. In normal cells, both probes will be observed (or a secondary color will be observed due to the close proximity of the two genes of the gene fusion), and only the single gene probe will be observed when the translocation occurs or the probes, having differing colors, will be separated such that one of ordinary skill in the art observing the probes can determine that a relevant gene fusion or deletion is present in the sample. Generally, FISH assays are performed using formalin-fixed, paraffin-embedded tissue sections that are placed on slides. The DNA from the tissue sample sections is denatured to single-stranded form and subsequently allowed to hybridize with the appropriate DNA probes that can be designed and prepared using methods and techniques known to those having ordinary skill in the art. Following hybridization, any unbound probe may be removed by a series of washes and the nuclei of the cells are counterstained with DAPI (4',6 diamidino-2-phenylindole), a DNA-specific stain that fluoresces blue. Hybridization of the probe or probes are viewed using a fluorescence microscope equipped with appropriate excitation and emission filters, allowing visualization of the fluorescent signals.

For example, a break-apart FISH assay may be used to detect multiple types of rearrangements involving the ALK gene locus. In the method, tumor cells from some subjects having non-small cell lung cancer (NSCLC), display an ALK-positive FISH pattern as detected using single interference filter sets comprising green (FITC), red (Texas red), and blue (4',6-diamidino-2-phenylindole) as well as dual (red/green) and triple (blue, red, green) band-pass filters. A fusion of the ALK gene is visualized as split orange and green signals, single orange signals, or single orange and single green signals.

Relevant molecular alterations with respect to ROS1, TrkA, TrkB and TrkC in biological samples derived from cancer subjects using the same methods as described above, but by modifying the reagents, probes and other materials used in the assays in ways that are appropriate to the target molecular alteration and as can be readily determined by those having ordinary skill in the art.

Other variations of the FISH method known in the art are suitable for evaluating a subject selected in accordance with the methods provided herein.

In some instances of the methods provided herein, the cancer is selected from the group consisting of anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, and papillary thyroid cancer. In some instances are provided such methods, wherein the knowledge of the presence of the one or more molecular alterations is obtained from an assay performed simultaneously on a plurality of biological samples. In some instances, the plurality of biological samples may be assayed in a multitest platform.

As used herein, the term "multitest platform" is intended to encompass any suitable means to contain one or more reaction mixtures, suspensions, or detection reactions. As such, the outcomes of a number of screening events can be assembled onto one surface, resulting in a "multitest platform" having, or consisting of multiple elements or parts to do more than one experiment simultaneously. It is intended that the term "multitest platform" encompasses protein chips, microtiter plates, multi-well plates, microcards, test tubes, petri plates, trays, slides, and the like. In some instances, multiplexing can further include simultaneously conducting a plurality of screening events in each of a plurality of separate biological samples. For example, the number of biological samples analyzed can be based on the number of spots on a slide and the number of tests conducted in each spot (as described in greater detail in Example 2). In another example, the number of biological samples analyzed can be based on the number of wells in a multi-well plate and the number of tests conducted in each well. For example, 6-well, 12-well, 24-well, 48-well, 96-well, 384-well, 1536-well or 3456-well microtiter plates can be useful in the presently disclosed methods, although it will be appreciated by those in the art, not each microtiter well need contain a subject biological sample. Depending on the size of the microtiter plate and the number of the subject biological samples in each well, very high numbers of tests can be run simultaneously. Although multiplexing has been exemplified in Example 2 with respect to micro-slides, it will be understood that other formats can be used for multiplexing.

In some instances are provided such methods, wherein the plurality of biological samples includes at least 6, 12, 24, 48, 96, 200, 384, 400, 500, 1000, 1250, 1500, or 3000 samples.

In some instances are provided such methods, wherein the one or more molecular alterations is selected from a genetic mutation, a gene amplification, a gene rearrangement, a single-nucleotide variation (SNV), a deletion, an insertion, an InDel mutation, a single nucleotide point mutation (SNP), an epigenetic alteration, a splicing variant, an RNA/protein overexpression, and an aberrant RNA/protein expression. In some instances are provided such methods, wherein the genetic alteration includes an insertion of a heterologous nucleic acid sequence within a coding sequence of a biomarker gene. In some instances are provided such methods, wherein the insertion forms a chimeric nucleic acid sequence that encodes a fusion peptide.

In some instances are provided such methods, wherein the acquiring knowledge of the one or more molecular alterations further comprises determining a nucleic acid sequence and/or an amino acid sequence comprising the one or more molecular alterations. In some instances, the nucleic acid sequence comprising the one or more molecular alterations from a selected cancer subject tumor is sequenced. In some instances, the sequence is determined by a next generation sequencing method.

Some embodiments provide a pharmaceutical composition comprising a therapeutically effective amount of N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof, and at least one polymer in combination with one or more chemotherapeutic agents or radiotherapy, such as radiotherapy as commonly administered to treat, ameliorate the symptoms of, or prevent or delay the onset of cancer. Such agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

Some embodiments provide a product or kit comprising a pharmaceutical composition as provided herein comprising N-[5-(3,5-difluorobenzyl)-1H-indazol-3-yl]-4-(4-methyl-piperazin-1-yl)-2-(tetrahydro-2H-pyran-4-ylamino)-benzamide, or a pharmaceutically acceptable salt thereof and one or more chemotherapeutic agents, as a combined preparation for simultaneous, separate or sequential use in anticancer therapy.

Some embodiments include any of the methods described herein, wherein said cancer is selected from non-small cell lung cancer, papillary thyroid cancer, neuroblastoma, pancreatic cancer and colorectal cancer. Some embodiments are any of the methods described herein wherein said cancer is non-small cell lung cancer. Some embodiments include any of the methods described herein, wherein said cancer is said cancer is papillary thyroid cancer. Some embodiments include any of the methods described herein, wherein said cancer is wherein said cancer is neuroblastoma. Some embodiments include any of the methods described herein, wherein said cancer is wherein said cancer is pancreatic cancer. Some embodiments include any of the methods described herein, wherein said cancer is wherein said cancer is colorectal cancer.

Some embodiments relate to any of the pharmaceutical compositions provided herein for use as a medicament. Some embodiments relate to the use of any of the pharmaceutical compositions provided herein for the manufacture of a medicament for the treatment of abnormal cell growth.

EXAMPLES

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

As will be understood by one skilled in the art, for any and all purposes, such as in terms of providing a written description, all ranges provided herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each subject member. Thus, for example, a group having 1-3 articles refers to groups having 1, 2, or 3 articles. Similarly, a group having 1-5 articles refers to groups having 1, 2, 3, 4, or 5 articles, and so forth.

The following abbreviations may be used in the examples that follow:

"PVPVA64" means a copolymer of 1-vinyl-2-pyrrolidone and vinyl acetate in a weight to weight ratio of 6 to 4.

Example 1: Studies of Solubility of N-[5-(3,5-difluorobenzyl)-1H-indazol-3-yl]-4-(4-methyl-piperazin-1-yl)-2-(tetrahydro-2H-pyran-4-ylamino)-benzamide The solubility of N-[5-(3,5-difluorobenzyl)-1H-indazol-3-yl]-4-(4-methyl-piperazin-1-yl)-2-(tetrahydro-2H-pyran-4-ylamino)-benzamide was evaluated in several solvents and mixtures of solvents that are known to those of ordinary skill in the art to be amenable to use of a fluid bed coating process. The solutions were all prepared at approximately 170 mg N-[5-(3,5-difluorobenzyl)-1H-indazol-3-yl]-4-(4-methyl-piperazin-1-yl)-2-(tetrahydro-2H-pyran-4-ylamino)-benzamide per mL of solvent. The solutions included 80/20 acetone/water, 95/5 acetone/water, 90/10 acetone/water, methyl ethyl ketone, acetone and methanol at 40° C. The acetone/water solutions provided solubility of N-[5-(3,5-difluorobenzyl)-1H-indazol-3-yl]-4-(4-methyl-piperazin-1-yl)-2-(tetrahydro-2H-pyran-4-ylamino)-benzamide of greater than mg/mL solubility for 24 hours. All acetone/water solutions appeared to be completely dissolved within 30 minutes. The lab temperature was monitored and ranged from 17° C. to 25° C., fluctuating with time of day during testing.

Example 2: Study of Solutions of N-[5-(3,5-difluorobenzyl)-1H-indazol-3-yl]-4-(4-methyl-piperazin-1-yl)-2-(tetrahydro-2H-pyran-4-ylamino)-benzamide for Use in Spray-Drying Processes Three solutions were prepared, comprising mixtures of acetone/water at weight ratios 80/20, 90/10, and 95/5, and N-[5-(3,5-difluorobenzyl)-1H-indazol-3-yl]-4-(4-methyl-piperazin-1-yl)-2-(tetrahydro-2H-pyran-4-ylamino)-benzamide at a solids content of wt % N-[5-(3,5-difluorobenzyl)-1H-indazol-3-yl]-4-(4-methyl-piperazin-1-yl)-2-(tetrahydro-2H-pyran-4-ylamino)-benzamide and 2.5% wt % PVP-VA. The order of addition was to add the polymer into the mixtures of acetone and water, followed the addition of N-[5-(3,5-difluorobenzyl)-1H-indazol-3-yl]-4-(4-methyl-piperazin-1-yl)-2-(tetrahydro-2H-pyran-4-ylamino)-benzamide. For all solvent systems the polymer dissolved immediately leaving a clear, colorless solution. Following the addition of the N-[5-(3,5-difluorobenzyl)-1H-indazol-3-yl]-4-(4-methyl-piperazin-1-yl)-2-(tetrahydro-2H-pyran-4-ylamino)-benzamide, several minutes of agitation was required to dissolve the solids completely resulting in a homogenous golden color with no turbidity or visible precipitate in the solution. These solutions were then transferred into a stainless steel container, sealed to prevent solvent evaporation, and placed in a controlled environment at 25° C. Another solution of the 80/20 w/w acetone/water mixture at the target 12.5 wt % N-[5-(3,5-difluorobenzyl)-1H-indazol-3-yl]-4-(4-methyl-piperazin-1-yl)-2-(tetrahydro-2H-pyran-4-ylamino)-benzamide was prepared and placed in a controlled 5° C. environment. Each solution was monitored for visual appearance at specified time intervals of 0, 1, 2, 3, and 7 days. Samples stored at the 25° C. condition were also sampled and tested for purity at each time point.

There were no observable changes in appearance in any of the samples through 7 days. All samples remained homogenous, golden in color, with no turbidity or visible precipitate in the solution.

Results showed that initial samples had a minimal number and quantity of impurities that showed little growth through 7 days at 25° C. No individual impurities surpassed 0.15% area and total impurities remained at or below 0.30% area for all three solvent systems. The impurity at RRT 1.10 was identified in the N-[5-(3,5-difluorobenzyl)-1H-indazol-3-yl]-4-(4-methyl-piperazin-1-yl)-2-(tetrahydro-2H-pyran-4-ylamino)-benzamide used for the study, grew as a function of storage time, but remained below 0.15% area after 7 days. A new peak relative to the N-[5-(3,5-difluorobenzyl)-1H-indazol-3-yl]-4-(4-methyl-piperazin-1-yl)-2-(tetrahydro-2H-pyran-4-ylamino)-benzamide control was identified at RRT 1.35. This peak started below the limit of quantitation (LOQ), but increased steadily with time to the point of being quantifiable at the 7 day time point. Finally, a signal identified at RRT 2.78 was observed for some samples at a quantifiable level, but not for others, however there was no indication of this trending upward with respect to time. A summary of the results is provided in FIG. 1, wherein "active" represents the amount of -[5-(3,5-difluorobenzyl)-1H-indazol-3-yl]-4-(4-methyl-piperazin-1-yl)-2-(tetrahydro-2H-pyran-4-ylamino)-benzamide in the solution at the given time point.

The growth rate of the impurity at RRT 1.10 was constant in all three solvent systems but the size of the impurity seems to be minimized in the 80/20 acetone/water solution. The impurity at RRT 1.35 remained visible in the chromatography but below LOQ until between 3 and 7 days of stability, at which time it appears just above LOQ in all three solvent systems. Both the growth rate and size of this impurity seem to be minimized in the 80/20 acetone and water solution.

Example 3: Preparation of Spray-Layered Dispersion

A spray-layered dispersion comprising 80/20 weight to weight of N-[5-(3,5-difluorobenzyl)-1H-indazol-3-yl]-4-(4-methyl-piperazin-1-yl)-2-(tetrahydro-2H-pyran-4-ylamino)-benzamide to PVPVA64 was prepared using a mixture of acetone and water (4:1 ratio) as the solvent system. The composition was manufactured using a fluidized bed coater with a bottom sprayer manufactured by Glatt with a 3.5 inch bowl. The starting bed weight was 100 g of Celphere CP102 cores with a starting bed weight of 100 g. A target coat weight of 50% was met, and additional samples at 30% and 40% were taken. The average process conditions used during preparation of the spray-layered dispersion was as follows:

| | |
|---|---|
| Total Spray time (min) | 198.0 |
| Spray rate (g/min) | 4.4 |
| Atomizer Pressure (bar) | 1.5 |
| Inlet Temp (° C.) | 24.0 |
| Bed Temp (° C.) | 17.5 |
| Outlet Temp (° C.) | 18.0 |
| Inlet Dew Pt. (° C.) | 14.2 |
| Outlet Dew Pt. (° C.) | 12.2 |
| Outlet RH (%) | 68.5 |
| Gas Flow (CMH) | 17.9 |

The final bed weight was 192.3 g after samples and loss (221.1 g total with sample and loss). The final weights equate to 112% spray efficiency. The spray efficiency being greater than 100% is hypothesized to be because of an incorrectly weighed initial bed. The initial bed was likely closer to ~125 g, which would bring the efficiency closer the expected result of ~85%.

All samples were tested for coating thickness and morphology via scanning electron microscopy (SEM), which showed a uniform coating with no surface or particle to particle agglomeration. An average thickness for the coating was determined from the SEM measurements. The table below provides the actual coating weight based on potency and average coating thickness for each of the samples.

| Lot No. | Estimated Coating Thickness |
|---|---|
| Lot 1 (30% theoretical coating weight) | ~15 μm |
| Lot 2 (40% theoretical coating weight) | ~18 μm |
| Lot 3 (50% theoretical coating weight) | ~25 μm |

Example 4: Preparation of Spray-Layered Dispersion

A spray-layered dispersion comprising 80/20 weight to weight of N-[5-(3,5-difluorobenzyl)-1H-indazol-3-yl]-4-(4-methyl-piperazin-1-yl)-2-(tetrahydro-2H-pyran-4-ylamino)-benzamide to PVPVA64 having a final theoretical coat weight of 55% was manufactured using a fluidized bed coater with a bottom sprayer manufactured by Glatt equipped with a 3.5 inch bowl. The starting bed weight was 100 g of Celphere CP102 cores. The solution used to apply N-[5-(3,5-difluorobenzyl)-1H-indazol-3-yl]-4-(4-methyl-piperazin-1-yl)-2-(tetrahydro-2H-pyran-4-ylamino)-benzamide to the cores was an 80/20 N-[5-(3,5-difluorobenzyl)-1H-indazol-3-yl]-4-(4-methyl-piperazin-1-yl)-2-(tetrahydro-2H-pyran-4-ylamino)-benzamide/PVPVA64, with 12.5 wt % total solids, in a 90/10 acetone/water mixture.

The manufacture observations saw no signs of agglomeration or spray drying of the solution. The average process conditions used during preparation of the spray-layered dispersion was as follows:

| | |
|---|---|
| Total Spray time (min) | 260.0 |
| Spray rate (g/min) | 4.3 |
| Atomizer Pressure (bar) | 1.8 |
| Inlet Temp (° C.) | 21.0 |
| Bed Temp (° C.) | 16.7 |
| Outlet Temp (° C.) | 17.0 |
| Inlet Dew Pt. (° C.) | 14.8 |
| Outlet Dew Pt. (° C.) | 11.3 |
| Outlet RH (%) | 68.3 |
| Gas Flow (CMH) | 17.8 |

During the manufacture samples were pulled at three other theoretical coat weights, 30%, 40%, and 50%. Visual observations during the manufacture showed no signs of agglomerations at all sample points. The final bed weight was 198.6 g after samples and loss (218.5 g total with sample and loss). The final weights equate to 85% spray efficiency. The potency, coating efficiencies, and estimated coating thickness at each of 30%, 40%, 50% and 55% theoretical coating weights are shown in the table below.

| Lot No. | Actual Coat Wt. Based on Potency | Coating Efficiency at Sample Point | Estimated Coating Thickness |
|---|---|---|---|
| Lot 1 (30% theoretical coating weight) | 28.1% | 79.6% | ~15 μm |
| Lot 2 (40% theoretical coating weight) | 37.8% | 80.2% | ~20 μm |
| Lot 3 (50% theoretical coating weight) | 47.0% | 79.9% | ~26 μm |
| Lot 4 (55% theoretical coating weight) | 53.5% | 82.6% | ~31 μm |

The 55% theoretical coat weight material, Lot 4 in this example, was tested for particle size distribution via sieve analysis. Approximately 8 g of material was sieved using a Retsch vibratory sieve shaker AS200. The shaker was run for 6 minutes at 60% amplitude with pulsing on. FIG. 2 shows the results of the particle size analysis. The results of the sieve analysis show a particle size Dv50 of 223 μm.

The performance of all four coating weights was evaluated by dissolution in pH 6.5 phosphate buffered saline (PBS) containing 0.5% SIF powder. The tests were performed at 1 mg N-[5-(3,5-difluorobenzyl)-1H-indazol-3-yl]-4-(4-methyl-piperazin-1-yl)-2-(tetrahydro-2H-pyran-4-ylamino)-benzamide/mL which is the approximate amorphous solubility of N-[5-(3,5-difluorobenzyl)-1H-indazol-3-yl]-4-(4-methyl-piperazin-1-yl)-2-(tetrahydro-2H-pyran-4-ylamino)-benzamide in this media. All four formulations appear to reach ~80% of the dose dissolved by 60 minutes. The initial dissolution rate increased as a function of decreasing coat weight. This is as expected given the surface area decreases as the coating thickness increases. The results are shown in FIG. 3, wherein "entrectinib" are N-[5-(3,5-difluorobenzyl)-1H-indazol-3-yl]-4-(4-methyl-piperazin-1-yl)-2-(tetrahydro-2H-pyran-4-ylamino)-benzamide. The test conditions were as follows: USP Apparatus II, 100 mL volume, 37° C., 250 RPM paddle speed, Dose: 1 mg N-[5-(3,5-difluorobenzyl)-1H-indazol-3-yl]-4-(4-methyl-piperazin-1-yl)-2-(tetrahydro-2H-pyran-4-ylamino)-benzamide/mL, Media: PBS with 0.5% SIF, pH 6.5. n=2.

Figure 4:
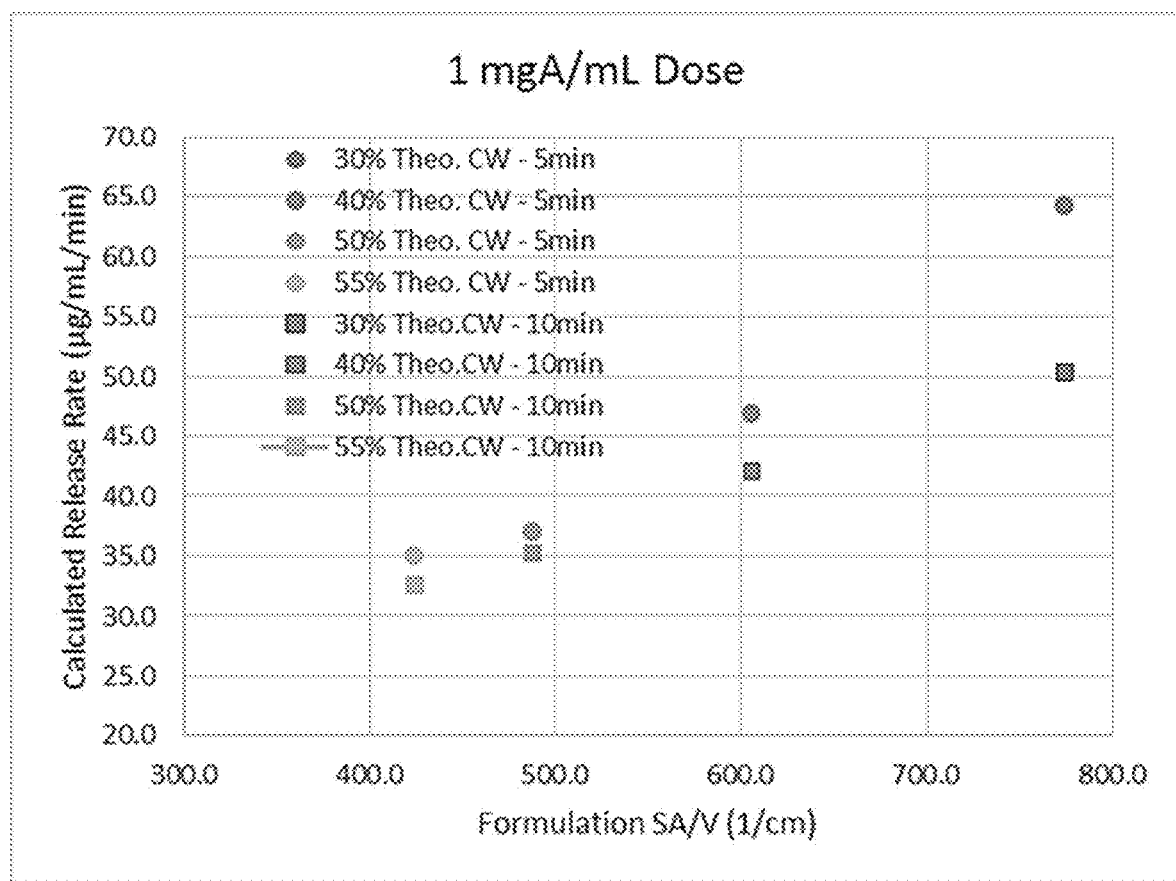
FIG. 4 shows the dissolution rates as a function of surface area/volume of formulations from Example 4.

The calculated release rate versus the ratio of surface area to volume for each of the four formulations is shown in FIG. 4, wherein "A" is N-[5-(3,5-difluorobenzyl)-1H-indazol-3-yl]-4-(4-methyl-piperazin-1-yl)-2-(tetrahydro-2H-pyran-4-ylamino)-benzamide.

Figure 5:
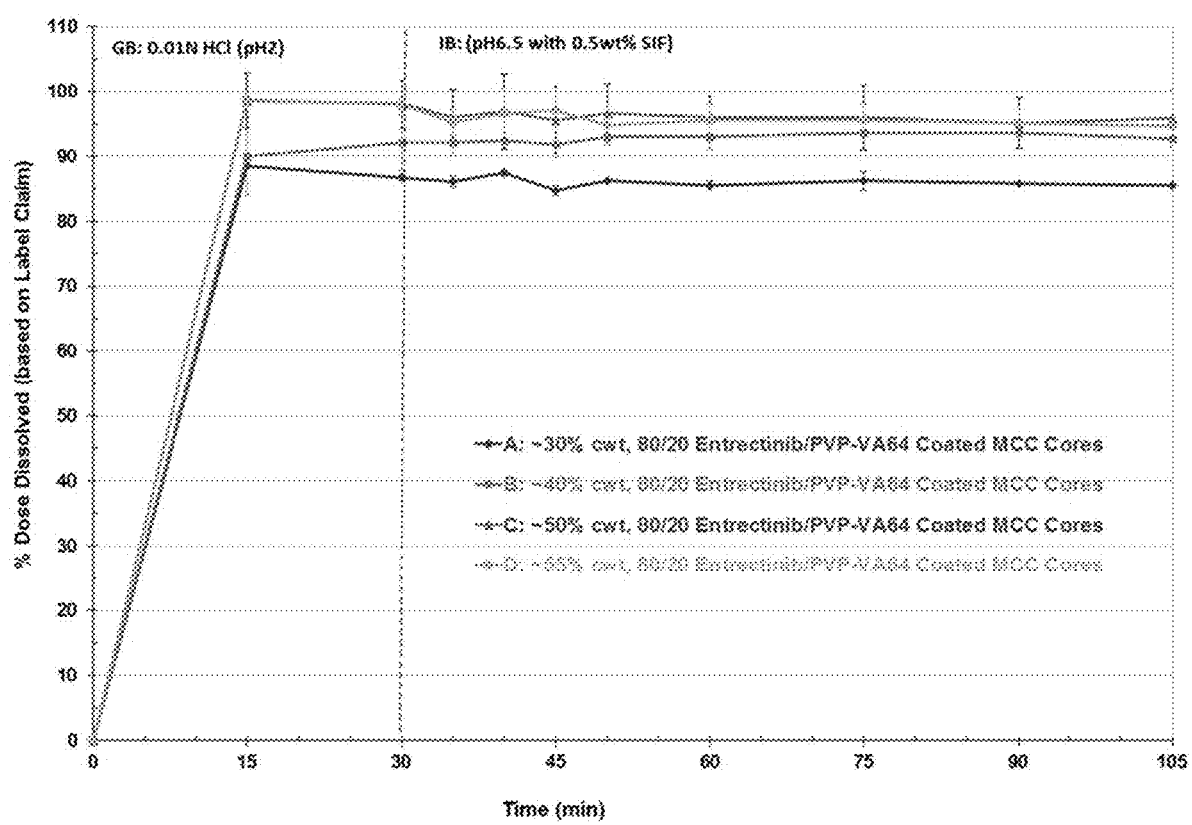
FIG. 5 shows GB/IB Dissolution Performance of 80/20 N-[5-(3,5-difluorobenzyl)-1H-indazol-3-yl]-4-(4-methyl-piperazin-1-yl)-2-(tetrahydro-pyran-4-ylamino)-benzamide/PVP-VA SLDs from Example 4 as a function of coat weight.

A two-stage dissolution test was also conducted on all four coating weights to determine if gastric exposure affected performance. The gastric-to-intestinal (GB/IB) dissolution test started with 75 mL of gastric media (GB: 0.01N HCl, pH 2) in which the formulations are dosed (dose in GB=1.33 mg A/mL). At the 15 and 30 minute time points 1 mL is collected from each vessel, centrifuged (1 minute at 15800 RCF), then 50 μL of the supernatant is diluted with 250 μL of diluent (7/3, water/acetonitrile with 0.01% trifluoroacetic acid). After 30 minutes of gastric exposure, 25 mL of 4× concentrated phosphate buffered saline (PBS), pH 6.47 with 2.0 wt % simulated intestinal fluid (SIF) is added to transfer to intestinal conditions (lx PBS, pH 6.5 with 0.5 wt % SIF). The test conditions were as follows: USP Apparatus II, 250 RPM paddle speed, Media: GB: 75 mL 0.01N HCl pH 2.14 after 30 minutes transferred to IB by adding 25 mL of 4×PBS with 2.0% SIF (Final IB Media: 100 mL PBS with 0.5% SIF, pH 6.5), 37° C. (Dose: in GB=1.33 mg A/mL, in IB=1 mg A/mL), Media: PBS with 0.5% SIF, pH 6.5. n=2 The results are shown in FIG. 5, wherein "entrectinib" is N-[5-(3,5-difluorobenzyl)-1H-indazol-3-yl]-4-(4-methyl-piperazin-1-yl)-2-(tetrahydro-2H-pyran-4-ylamino)-benzamide. All four coat weights appear to reach 90-100% of the dose dissolved based on label claim (or theoretical potency) by the 15 minute gastric time point. All four coat weights maintain the concentration achieved in gastric media even after transfer to IB (pH 6.5) with no observed precipitation. For concentrations less than the theoretical dose, this is believed to be due to variation in the actual potency of the samples which can be dependent on process efficiencies and final water content of the formulations.

The potency of all four coating weights were measured and was 1-6% lower than expected for all formulations. This difference is hypothesized to be due to coating efficiency, or high and variable water content of the samples. The standard deviation of (n=3) replicates was less than 2% in all cases with the exception of the 50% coating weight sample. The third replicate of this sample was likely an analytical error; if excluded from the data would have resulted in a potency of 376 mg/gram, or 94% of label claim.

The 30% coating weight and 55% coating weight formulations were stored at 50° C. and 75% relative humidity for one week and then assessed for morphology (SEM) and purity by HPLC. The results showed that the morphology and surface attributes of the formulations were similar to the unaged formulations and did not show any discernible crystal formation.

Figures 6, 7:
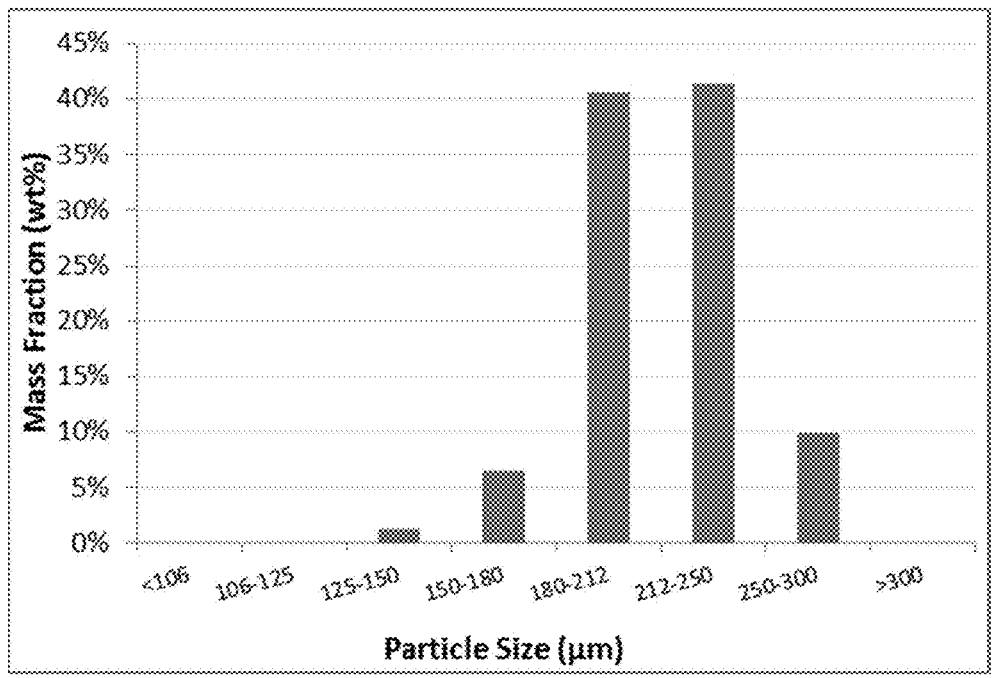
FIG. 6 shows the differential scanning calorimetry (DSC) results of formulations from Example 4.
FIG. 7 shows the particle size distribution of the 50% theoretical coating weight formulation from Example 5.

Thermal analysis was performed on each of the coating levels by modulated differential scanning calorimetry (DSC). A glass transition temperature (Tg) of ~100° C. was observed for all 4 coating levels as shown in the table below and FIGS. 6 and 7. A small melting point was observed for formulations with all four coating levels at about 196° C. which correlates to the melting point of N-[5-(3,5-difluorobenzyl)-1H-indazol-3-yl]-4-(4-methyl-piperazin-1-yl)-2-(tetrahydro-2H-pyran-4-ylamino)-benzamide.

Example 5: Preparation of Spray-Layered Dispersion

A formulation comprising 80/20 N-[5-(3,5-difluorobenzyl)-1H-indazol-3-yl]-4-(4-methyl-piperazin-1-yl)-2-(tetrahydro-2H-pyran-4-ylamino)-benzamide/PVPVA was manufactured using a fluidized bed coater with a bottom sprayer manufactured by Glatt equipped with a 6" bowl at a 1.0 kg starting bed scale. The 80/20 N-[5-(3,5-difluorobenzyl)-1H-indazol-3-yl]-4-(4-methyl-piperazin-1-yl)-2-(tetrahydro-2H-pyran-4-ylamino)-benzamide/PVPVA mixture of was sprayed out of 80/20 acetone/water with 12.5 wt % solids. The resulting material had a target final coat weight of 50%. Samples of intermediate material were taken at the coat weights of 30% and 40%. Observations throughout the manufacture noted very minimal agglomeration and minimal static build-up. The total amount of solution sprayed was 9323 g. The target coat weight of 50% was reached after average spray rate of 23 g/min was sprayed for 413 minutes. The batch solution was noted to have a red/rose colored solution. The average process parameters for the preparation of the formulations are shown in the table below:

| | |
|---|---|
| Total Spray time (min) | 413.0 |
| Spray rate (g/min) | 22.6 |
| Atomizer Pressure (bar) | 2.2 |
| Inlet Temp (° C.) | 26.0 |
| Bed Temp (° C.) | 17.6 |
| Outlet Temp (° C.) | 17.3 |
| Inlet Dew Pt. (° C.) | 11.0 |
| Outlet Dew Pt. (° C.) | 11.6 |
| Outlet RH (%) | 70.3 |
| Gas Flow (CMH) | 86.6 |

Once the target amount of solution was sprayed the pump was shut off and the material continued to fluidize within the Glatt. The inlet humidifier was shut off and the heater was set to ambient temp (20° C.). The cores were then dried until the outlet relative humidity (RH) was between 30% and 40%. After 12 mins of drying the outlet RH was 36% and the fluidizing air was shut off and the bed dumped. A final bed weight of 2192.2 g of material was collected prior to tray drying. The estimated spray efficiency for the batch was 105%. Based on the data from previous development runs it is known that the product contains enough residual water to raise the spray efficiency to a value greater than 100%. Based on visual observations within the equipment, filters, and during product collection there was minimal spray drying and the spray efficiency was as expected, >85%.

The bulk material was then placed into a tray dryer to lower the residual acetone and water to an acceptable level. The SLD was held in the tray dryer for 8 hours at 35° C. and 30% RH. A drying curve was collected on the bulk material where GC samples (for acetone) and KF samples (for water) were collected at 0, 1, 2, 5, 8, and 24 hrs (a small sample was left in the tray dryer to collect the 24 hr sample) to determine the time required to lower the acetone and water content to an acceptable level. The residual acetone started at ~4000 ppm and was reduced to 3000 ppm after 8 hours of secondary drying and dropped to 2500 ppm after 24 hours.

After tray drying, the bulk material was sieved to provide a bulk collection of particles having a diameter of between 150 μm and 300 μm. The material was first hand-sieved through a 12 inch 300 μm sieve. No measurable material was retained and the material readily passed through the sieve.

The material <300 μm was then hand-sieved through a 12 inch 150 μm sieve. Static was a significant issue during the sieving process but it was observed that very minimal material passed through the sieve. Approximately 2.3 g out of the 2025 g of material passed through the 150 μm sieve.

Morphology and coating thickness was determined via SEM. Single particles were first inspected under a light microscope and cut in half using a razor blade. The sliced particulates were then inspected via SEM for the coating thickness. The table below provides the approximate coating thickness for each target coat weight. Each estimated coating thickness measurement is from 12 individual sliced particle measurements.

| Lot No. | Estimated Coating Thickness |
|---|---|
| Lot 1 (30% theoretical coating weight) | ~15 μm |
| Lot 2 (40% theoretical coating weight) | ~18 μm |
| Lot 3 (50% theoretical coating weight) | ~25 μm |

Figures 8, 9:
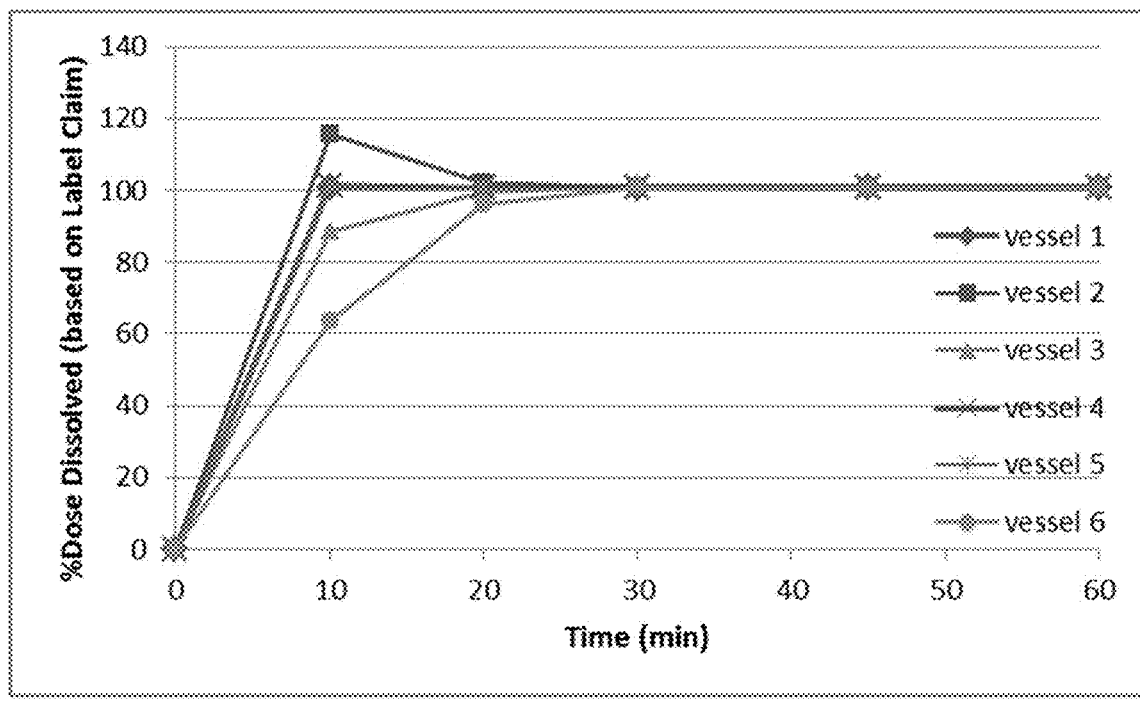
FIG. 8 shows the dissolution of the 50% theoretical coating weight formulation from Example 5.
FIG. 9 shows the dissolution data of the 50% theoretical coating weight formulation from Example 5.

The bulk material was characterized for bulk and tap density and particle size via sieve analysis. The bulk and tap density was measured in a 100 cc graduated cylinders for an n=2. The data for the formulation having a 50% theoretical coating weight is found in the table below. The particle size distribution for the formulation having a 50% theoretic coating weight is shown in FIG. 8.

| Lot No. | Bulk Density (g/cc) | Tap Density (g/cc) | Carr Index |
|---|---|---|---|
| Lot 3 | 0.76 | 0.79 | 4 |

Dissolution analysis was performed on the formulation having a 50% theoretical coating weight under three different conditions: 1) sink media (0.1M HCl) in standard USPII test, 2) a gastric-to-intestinal test, and 3) a non-sink dissolution test, each of which is described in more detail below.

Figure 10:
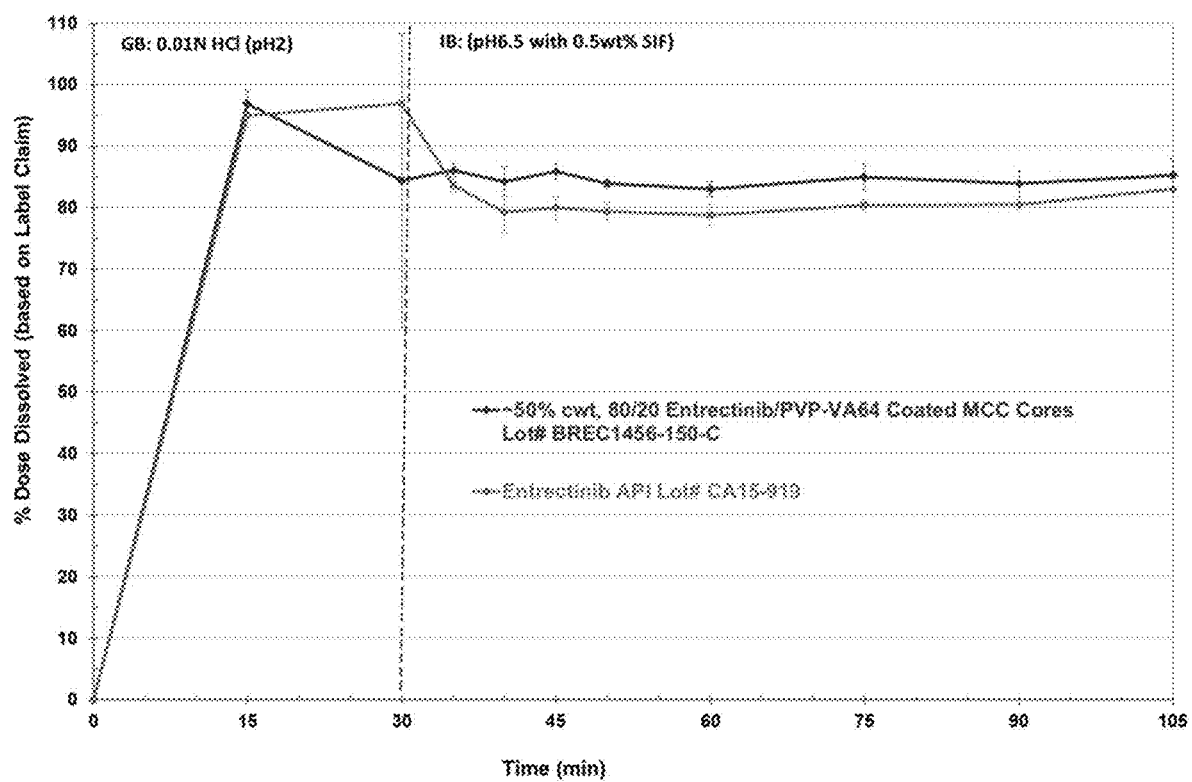
FIG. 10 shows the dissolution data of the 50% theoretical coating weight formulation from Example 5 in the gastric-to-intestinal (GB-IB) non-sink dissolution test.

Sink dissolution test 1: The formulation having a 50% theoretical coating weight was tested in 0.1 M HCl medium and time points at 10, 20, 30, 45 and 60 minutes. The % Dose Dissolved was 100% at 30 minutes as shown in FIGS. 9 and 10.

Gastric-to-intestinal (GB-IB) non-sink dissolution test: The formulation having a 50% theoretical coating weight was tested in a GB-IB non-sink dissolution test as described in the table below:

| | | |
|---|---|---|
| Apparatus | USP Apparatus II (Paddles) | |
| Nominal Dose | 100 mg N-[5-(3,5-difluorobenzyl)-1H-indazol-3-yl]-4-(4-methyl-piperazin-1-yl)-2-(tetrahydro-2H-pyran-4-ylamino)-benzamide | |
| Volume | 75 mL for first 30 minutes, 100 mL for remainder of the test in 100 or 200 mL vessel | |
| Media | Media 1: | 75 mL 0.01M HCl |
| | Media 2: | 25 mL of 4x PBS containing: 0.32M NaCl, 0.08M Na2PO4, 0.192M KH2PO4 A 2.0% SIF powder |
| | Final Media | 100 mL of pH 6.5 media containing: 0.08M NaCl, 0.02M Na2PO4, 0.048M KH2PO4 0.5% SIF powder |
| Sample Addition | 1. | Weigh sample into 10-20 mL scintillation vial |
| | 2. | Pour sample slowly onto media, tapping to remove any excess material |
| | 3. | If LMPs continue to float on surface, remove media from vessel with disposable Pasteur pipet and dispense media onto floating particles and repeat until a majority of LMPs are no longer floating. |
| Stir Speed | 250 rpm | |
| Temperature | 37° C. | |
| Timepoints | 15 and 30 minutes (GB), 5, 10, 15, 20, 30, 45, 60 and 75 minutes (IB) | |
| Sampling Method | 1. | Remove 1.0 mL using syringe and 10 µm full flow cannula filter |
| | 2. | dilute filtered sample 50 µL to 250 µL of 0.1M HCl |

Figure 11:
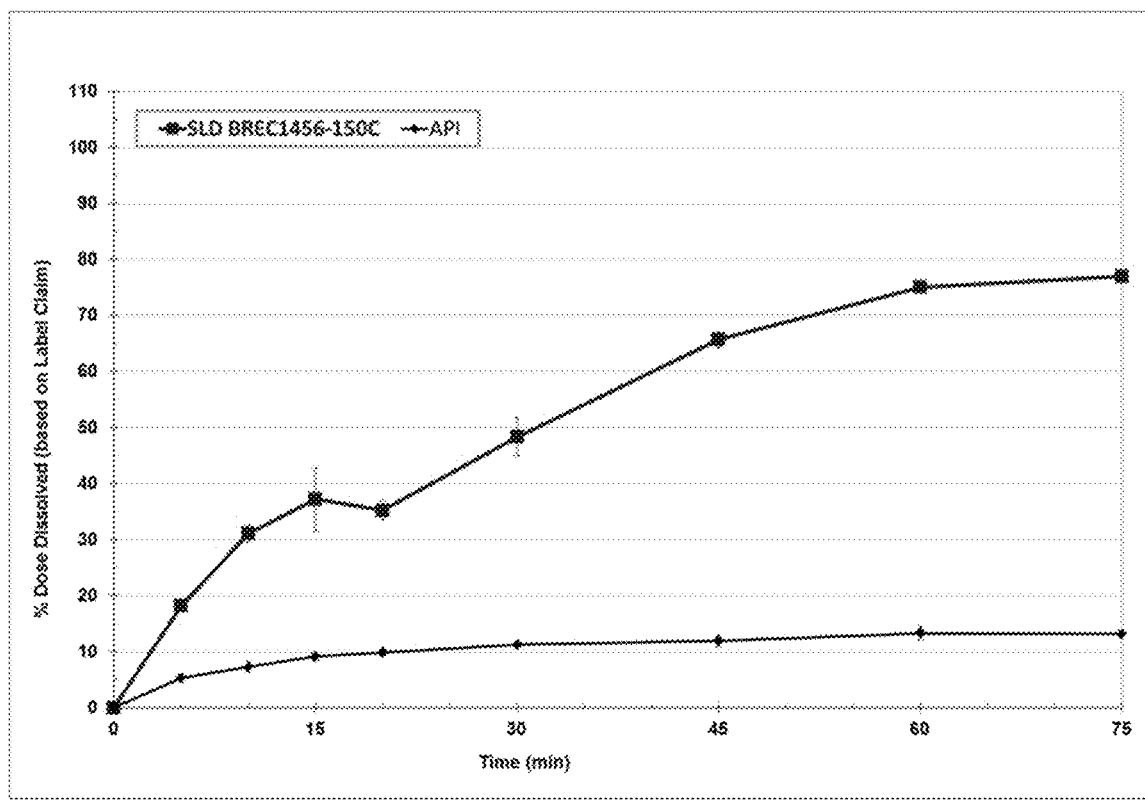
FIG. 11 shows the dissolution data of the 50% theoretical coating weight formulation from Example 5 in the non-sink dissolution test.

FIG. 11 shows the performance of the lot as compared to crystalline N-[5-(3,5-difluorobenzyl)-1H-indazol-3-yl]-4-(4-methyl-piperazin-1-yl)-2-(tetrahydro-2H-pyran-4-ylamino)-benzamide (API). Both the formulation and the API reach full dose in the pH 2.0 media and then maintain 80-90% of the 1 mg N-[5-(3,5-difluorobenzyl)-1H-indazol-3-yl]-4-(4-methyl-piperazin-1-yl)-2-(tetrahydro-2H-pyran-4-ylamino)-benzamide/mL dose in the intestinal media which contains 0.5% SIF.

Non-sink dissolution test: The formulation having a 50% theoretical coating weight was tested at 1 mg N-[5-(3,5-difluorobenzyl)-1H-indazol-3-yl]-4-(4-methyl-piperazin-1-yl)-2-(tetrahydro-2H-pyran-4-ylamino)-benzamide/mL in PBS, pH 6.5 media containing 0.5% SIF as described in the table below:

| | |
|---|---|
| Apparatus | USP Apparatus II (Paddles) |
| Nominal Dose | 100 mg N-[5-(3,5-difluorobenzyl)-1H-indazol-3-yl]-4-(4-methyl-piperazin-1-yl)-2-(tetrahydro-2H-pyran-4-ylamino)-benzamide |
| Volume | 75 mL for first 30 minutes, 100 mL for remainder of the test in 100 or 200 mL vessel |
| Media | 100 mL of PBS, pH 6.5 with 0.5% SIF |
| Sample Addition | Weigh sample into 10-20 mL scintillation vial Pour sample slowly onto media, tapping to remove any excess material If LMPs continue to float on surface, remove media from vessel with disposable Pasteur pipet and dispense media onto floating particles and repeat until a majority of LMPs are no longer floating. |
| Stir Speed | 250 rpm |
| Temperature | 37° C. |
| Timepoints | 5, 10, 15, 20, 30, 45, 60 and 75 minutes |
| Sampling Method | Remove 1.0 mL using syringe and 10 µm full flow cannula filter dilute filtered sample 50 µL to 250 µL of 0.1M HCl |

The formulation having a 50% theoretical coating weight released approximately 80% of the dose within about 75 minutes, whereas crystalline N-[5-(3,5-difluorobenzyl)-1H-indazol-3-yl]-4-(4-methyl-piperazin-1-yl)-2-(tetrahydro-2H-pyran-4-ylamino)-benzamide (API) has released about 15% of the dose after about the same time as shown in FIG. 12. This data suggests that the formulation has improved the release of N-[5-(3,5-difluorobenzyl)-1H-indazol-3-yl]-4-(4-methyl-piperazin-1-yl)-2-(tetrahydro-2H-pyran-4-ylamino)-benzamide as compared to crystalline N-[5-(3,5-difluorobenzyl)-1H-indazol-3-yl]-4-(4-methyl-piperazin-1-yl)-2-(tetrahydro-2H-pyran-4-ylamino)-benzamide.

Thermal analysis was performed on the 50% theoretical coating weight formulation by modulated DSC. An average glass transition temperature (Tg) of about 100° C. was observed. A small melting point was observed for at about 192° C.

The formulation having a 50% theoretical coating weight was set up on stability in high density polyethylene bottles with HIS with and without desiccant at one of 4 conditions: (1) 5° C., (2) 25° C. and 60% RH, (3) 30° C. and 65% RH, and (4) 40° C. and 75% RH.

Samples stored at 25° C./60% RH, 30° C./65% RH, and 40° C./75% RH for one month in HDPE containers with HIS closures were evaluated.

Surface morphology of the sample was determined via SEM. No changes in the surface of the particles were observed after storage for 1 month at any condition.

The 1-month stability samples were tested in 0.1 M HCl dissolution medium. Samples stored at all three conditions reached full release within the first 10 minutes.

The 1-month stability samples as well as the SLD stored refrigerated in amber glass were tested in at 1 mg N-[5-(3,5-difluorobenzyl)-1H-indazol-3-yl]-4-(4-methyl-piperazin-1-yl)-2-(tetrahydro-2H-pyran-4-ylamino)-benzamide/mL in PBS, pH 6.5 media containing 0.5% SIF previously. Samples stored at all conditions reached nearly full release within 60 minutes. All four samples showed a slowed rate between 20 and 30 minutes with a second, slower rate after 30 minutes. Visual observations noted that approximately 20 minutes is when the coating began to come off the cores and agglomerate with itself in the vessels. A similar profile was observed for the initial testing of this SLD, however the slowed rate began between 10 and 20 minutes. The samples stored at 5° C. and 25° C. exhibited slower release during the period after 30 minutes.

Related substances analysis was performed on the 50% theoretical coating weight formulation stability samples at the 1 month time point. The overall purity was similar to the ingoing API with the exception of a peak at RRT 1.13, which was at about the same level for all four samples. The impurity at RRT 1.13 appears to be related to the spray solution as and did not increase significantly at any condition after 1 month.

Example 6: Preparation of Spray-Layered Dispersion

A formulation comprising N-[5-(3,5-difluorobenzyl)-1H-indazol-3-yl]-4-(4-methyl-piperazin-1-yl)-2-(tetrahydro-2H-pyran-4-ylamino)-benzamide/PVPVA was manufactured as follows:

| Component | Product composition (mg/g) | Solution composition (wt %) | Target batch quantity (grams) | Estimated quantity (grams)* |
|---|---|---|---|---|
| N-[5-(3,5-difluorobenzyl)-1H-indazol-3-yl]-4-(4-methyl-piperazin-1-yl)-2-(tetrahydro-2H-pyran-4-ylamino)-benzamide | 400 | 10 | 1900 | 1758 |
| Kollidon VA 64/(NF) | 100 | 2.5 | 475 | 439 |
| Celphere CP-102/(NF) | 500 | | 2000 | 1850 |
| Acetone/(NF) | N/A | 70 | 13300 | 12,303 |
| Water, USP Purified/(USP) | N/A | 17.5 | 3325 | 3076 |
| Total | 1000 | 100 | | 19,426 |

*Amounts are estimated based on the weight of spray solution remaining after a first run was stopped before completion due to agglomeration.

The acetone purified water were weighed into a processing tank and the processing tank was thereafter purged with nitrogen. An agitator in the tank was turned on and the speed was adjusted to achieve a good mixing vortex without entraining the purge gas and the solvents were allowed to mix for 15 minutes. The N-[5-(3,5-difluorobenzyl)-1H-indazol-3-yl]-4-(4-methyl-piperazin-1-yl)-2-(tetrahydro-2H-pyran-4-ylamino)-benzamide was added to the processing tank with stirring and the tank was thereafter purged with nitrogen, and the resulting mixture was stirred for at least 60 minutes until no undissolved materials were present.

A NIRO MP-2 fluid bed processor was equipped with a reduced volume (6-inch) bowl, a modified reduced B plate distributor plate, a plate screen size 120 mesh, a Schlick 970 nozzle with a 1.2 mm tip, size 16 Chemsure tubing, and an exhaust air filter bag. The temperature in the processing room was recorded to be about 71° C. and the humidity was recorded to be about 39.44% relative humidity (% RH). The fluid bed processor was set up with the following parameters: atomization air (1.7 bar to 2.7 bar); fluidizing air (75 cubic meters per hour (CMH) to 105 CMH); inlet temperature was adjusted as necessary; inlet air dewpoint temperature (8° C. to 14° C.), and bed temperature (19° C. to 25° C.). The pump of the processor was set to achieve a spray rate of about 10 g/min to about 26 g/min, with a target rate of about 23 g/min. The processor was charged with the weighed quantity of Celphere CP-102/NF through the side addition port and the fluidization air was thereafter adjusted to maintain good mixing in the downbed. The coating spray was started following the bed had achieved a temperature of 22° C. The pump was thereafter started at 50% to 75% of the target rate for the first 10 minutes and was thereafter increased over the next 30 minutes to the target spray rate. Samples were taken to ensure there was no agglomeration of product. The spraying coating process was stop after the weight of the target coating solution to spray was achieved (target amount of spray coating solution to spray=17408.5 g; actual=17,408.6 g).

Following the stoppage of spray coating, the atomization air was reduced to 0.5 bar, the inlet air temperature and air dewpoint were reduced until the relative humidity of the outlet stream was in the target range of between about 30% and about 40%, with a target of 35% relative humidity. The contents of the fluid bed were then discharged into an appropriate container, as much air as possible was purged from the container and the container was sealed.

The materials were then further dried in a tray drier and the resulting materials were hand screened through a 50 mesh sieve and collected.

Para. A. A pharmaceutical composition, comprising a solid dispersion of N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and at least one polymer.

Para. B. The pharmaceutical composition according to Para. A, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is substantially amorphous.

Para. C. The pharmaceutical composition according to Para. A or Para. B, wherein said at least one polymer is selected from the group consisting of polyvinyl pyrrolidone, polyethyleneoxide, a copolymer of 1-vinyl-2-pyrrolidone and vinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose, hydroxypropyl cellulose, carboxymethyl ethylcellulose, hydroxypropyl methylcellulose acetate succinate, cellulose acetate phthalate, cellulose acetate trimellitate, ethyl cellulose, cellulose acetate, cellulose butyrate, cellulose acetate butyrate, and dextran polymer derivative.

Para. D. The pharmaceutical composition according to any one of Paras. A-C, wherein said pharmaceutical composition is in the form of particles.

Para. E. The pharmaceutical composition according to Para. D, wherein said particles comprise a cellulose core.

Para. F. The pharmaceutical composition according to Para. D or Para. E, wherein the average diameter of said particles is between about 150 micrometers and about 300 micrometers.

Para. G. The pharmaceutical composition according to any one of Paras. D-F, wherein not less than about 80% of said particles have a diameter between about 150 micrometers and about 300 micrometers.

Para. H. The pharmaceutical composition according to any one of Paras. D-F, wherein not more than about 20% of said particles have a diameter larger than about 300 micrometers.

Para. I. The pharmaceutical composition according to Para. E, wherein said -[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer comprise at least one layer on said cellulose core.

Para. J. The pharmaceutical composition according to any one of Paras. A-I, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, to said at least one polymer is from about 1 to 10 to about 10 to 1.

Para. K. The pharmaceutical composition according to Para. E, wherein the weight to weight ratio of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, plus said at least one polymer to said cellulose core is from about 1 to 10 to about 10 to 1.

Para. L. The pharmaceutical composition according to Para. I, wherein said at least one layer on said cellulose core has a thickness of from about 5 micrometers to about 40 micrometers.

Para. M. The pharmaceutical composition according to Para. A, wherein said at least one polymer comprises a copolymer of 1-vinyl-2-pyrrolidone and vinyl acetate.

Para. N. The pharmaceutical composition according to Para. M, wherein the weight to weight ratio of 1-vinyl-2-pyrrolindone to vinyl acetate comprising said copolymer of 1-vinyl-2-pyrrolidone and vinyl acetate is from about 1 to 10 to about 10 to 1.

Para. O. The pharmaceutical composition according to any one of Paras. A-N, wherein said pharmaceutical composition releases at least about 25% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 60 minutes in pH 6.5 phosphate buffered saline.

Para. P. The pharmaceutical composition according to any one of Paras. A-N, wherein said pharmaceutical composition releases not less than about 70% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 60 minutes in pH 6.5 phosphate buffered saline.

Para. Q. The pharmaceutical composition according to any one of Paras. A-N, wherein said pharmaceutical composition releases at least about 25% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, in about 15 minutes in 75 mL of aqueous solution at pH 2.

Para. R. The pharmaceutical composition according to any one of Paras. A-Q, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprises at least about 5% of the total weight of said composition.

Para. S. The pharmaceutical composition according to any one of Paras. A-R, wherein said composition comprises from about 1% to about 25% by weight of water.

Para. T. The pharmaceutical composition according to any one of Paras. A-R, wherein said composition comprises no more than about 10,000 parts per million of residual solvent.

Para. U. The pharmaceutical composition according to Para. A, wherein said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, is substantially amorphous following storage of said pharmaceutical composition at 50° C. and 75% relative humidity for at least 7 days.

Para. V. The pharmaceutical composition according to Para. D, wherein the bulk density of said particles is between about 0.25 g per cubic centimeter and about 1 gram per cubic centimeter.

Para. W. The pharmaceutical composition according to Para. D, wherein the tap density of said particles is between about 0.25 g per cubic centimeter and about 1 gram per cubic centimeter.

Para. X. The pharmaceutical composition according to Para. D, wherein the Carr index of said particles is between about 3 and about 21.

Para. Y. The pharmaceutical composition according to Para. D, wherein the d50 of said particles is between about 100 micrometers and about 500 micrometers.

Para. Z. The pharmaceutical composition according to any one of Paras. A-R, wherein said composition comprises no more than about 1% by weight of residual solvent.

Para. AA. The pharmaceutical composition according to any one of Paras. A-N, wherein said pharmaceutical composition releases at least about 20% of the total amount of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, comprising said pharmaceutical composition after about 30 minutes in a USP apparatus II (paddles) containing 75 mL of phosphate buffered saline, wherein said phosphate buffered saline has pH 6.5, is at a temperature of 37° C., and is stirred at 250 rpm.

Para. AB. A pharmaceutical composition according to any one of Paras. A-N, wherein said pharmaceutical composition has a dissolution profile wherein at least about 20% of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, has been released from said pharmaceutical composition at about 30 minutes when tested in USP Apparatus Type II (paddles) at 250 rpm in 75 mL of phosphate buffered saline at a pH of 6.5 and at about 37° C.

Para. AC. A pharmaceutical composition according to any one of Paras. A-AB, wherein said pharmaceutical composition is in the form of a granule, a powder, tablet or capsule.

Para. AD. A pharmaceutical composition according to Para. AC, wherein said pharmaceutical composition is in the form of a granule.

Para. AE. A pharmaceutical composition according to Para. AC, wherein said pharmaceutical composition is in the form of a powder.

Para. AF. A pharmaceutical composition according to Para. AC, wherein said pharmaceutical composition is in the form of a tablet.

Para. AG. A pharmaceutical composition according to Para. AC, wherein said pharmaceutical composition is in the form of a capsule.

Para. AH. A method of inhibiting at least one of ALK, ROS1, TrkA, TrkB, or TrkC kinase activity in a subject in need thereof, comprising administering to said subject a therapeutically effective amount of a pharmaceutical composition according to any one of Paras. A-AG.

Para. AI. A method of treating cancer in a subject in need thereof, the method comprising inhibiting ALK, ROS1, TrkA, TrkB, or TrkC activity, or a combination thereof, in said subject, by administering to said subject a therapeutically effective amount of a pharmaceutical composition according to any one of Paras. A-AG.

Para. AJ. A method of treating cancer in a subject in need thereof, comprising administering to said subject a therapeutically effective amount of a pharmaceutical composition according to any one of Paras. A-AG.

Para. AK. A method of treating cancer in a subject in need thereof, wherein one or more cells comprising said cancer in said subject have been determined to comprise at least one gene rearrangement comprising the gene, or a fragment thereof, that expresses at least one of ALK, ROS1, TrkA, TrkB, or TrkC kinase, comprising administering to said subject a therapeutically effective amount of a pharmaceutical composition according to any one of Paras. A-AG.

Para. AL. A method of treating cancer in a subject, the method comprising: (1) testing one or more cells comprising the cancer in said subject for the presence of at least one of ALK, ROS1, TrkA, TrkB, or TrkC kinase; and (2) administering to the subject a therapeutically effective amount of a pharmaceutical composition according to any one of Paras. A-AG if said one or more cells tests positive for at least one of ALK, ROS1, TrkA, TrkB, or TrkC kinase.

Para. AM. A method of treating cancer in a subject, wherein one or more cancerous cells in said subject express at least one of ALK, ROS1, TrkA, TrkB, or TrkC kinase, the method comprising administering to the subject an effective amount of a pharmaceutical composition according to any one of Paras. A-AG.

Para. AN. A method of treating a subject having cancer, wherein tumors from said subject are ALK, ROS1, TrkA, TrkB, or TrkC positive, the method comprising administering to the subject a therapeutically effective amount of a pharmaceutical composition according to any one of Paras. A-AG.

Para. AO. A method of treating cancer in a subject, comprising (a) acquiring knowledge of the presence of at least one genetic alteration in at least one target gene in said subject, wherein the at least one target gene is selected from ALK1, BDNF, NGF, NGFR, NTF3, NTF4, ROS1, SORT1, NTRK1, NTRK2, and NTRK3; and (b) selecting a pharmaceutical composition according to any one of Paras. A-AG as a treatment for said subject, based on the recognition that said pharmaceutical composition is effective in treating the subject having said at least one genetic alteration in said at least one target gene; and (c) administering a therapeutically effective amount of said pharmaceutical composition to said subject.

Para. AP. A method of treating a cancer in a subject, comprising administering to said subject a therapeutically effective amount of a pharmaceutical composition according to any one of Paras. A-AG, wherein prior to said administration of said pharmaceutical composition, said subject is known to possess at least one genetic alteration in at least one target gene selected from ALK1, BDNF, NGF, NGFR, NTF3, NTF4, ROS1, SORT1, NTRK1, NTRK2, and NTRK3.

Para. AQ. A method of treating cancer in a subject, wherein said subject is known to possess at least one genetic alteration in at least one target gene, comprising administering to said subject a therapeutically effective amount of a pharmaceutical composition according to any one of Paras. A-AG, and wherein said target gene is selected from ALK1, BDNF, NGF, NGFR, NTF3, NTF4, ROS1, SORT1, NTRK1, NTRK2, and NTRK3.

Para. AR. A method according to any one of Paras. AI-AQ, wherein said cancer is selected from anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, papillary thyroid cancer, or any combination thereof.

Para. AS. A method according to Para. AR, wherein said cancer is non-small cell lung cancer.

Para. AT. A method according to Para. AR, wherein said cancer is papillary thyroid cancer.

Para. AU. A method according to Para. AR, wherein said cancer is neuroblastoma.

Para. AV. A method according to Para. AR, wherein said cancer is pancreatic cancer.

Para. AW. A method according to Para. AR, wherein said cancer is colorectal cancer.

Para. AX. The pharmaceutical composition according to any one of Paras. A-AG, wherein said composition comprises from about 10 mg to about 1000 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof.

Para. AY. A method for treating cancer in a subject, comprising:
(a) acquiring knowledge of the presence of one or more molecular alterations in a biological sample from said subject, wherein said one or more molecular alterations comprises one or more mutations in one or more receptor tyrosine kinase polypeptides, wherein the one or more receptor tyrosine kinase polypeptide is selected from TrkA, TrkB, TrkC, ALK and ROS1; and
(b) administering a therapeutically effective amount of a pharmaceutical composition according to any one of Paras. A-AG to said subject.

Para. AZ. The method of Para. AY, wherein said one or more amino acid substitutions is at a position corresponding to amino acid residue G595 of the TrkA polypeptide.

Para. BA. The method of Para. AZ, wherein said one or more amino acid substitutions is a Glu-to-Arg substitution (G595R).

Para. BB. The method of Para. AY, wherein said one or more amino acid substitutions is at a position corresponding to amino acid residue G667 of the TrkA polypeptide.

Para. BC. The method of Para. BB, wherein said one or more amino acid substitutions is a Glu-to-Cys substitution (G667C).

Para. BD. The method of Para. AY, wherein said one or more amino acid substitutions is at a position corresponding to amino acid residue G639 of the TrkB polypeptide.

Para. BE. The method of Para. BD, wherein said one or more amino acid substitutions is a Glu-to-Arg substitution (G639R).

Para. BF. The method of Para. AY, wherein said one or more amino acid substitutions is at a position corresponding to amino acid residue G709 of the TrkB polypeptide.

Para. BG. The method of Para. BF, wherein said one or more amino acid substitutions is a Glu-to-Cys substitution (G709C).

Para. BH. The method of Para. AY, wherein said one or more amino acid substitutions is at a position corresponding to amino acid residue G623 of the TrkC polypeptide.

Para. BI. The method of Para. BH, wherein said one or more amino acid substitutions is a Glu-to-Arg substitution (G623R).

Para. BJ. The method of Para. AY, wherein said one or more amino acid substitutions is at a position corresponding to amino acid residue G696 of the TrkC polypeptide.

Para. BK. The method of Para. BJ, wherein said one or more amino acid substitutions is a Glu-to-Cys substitution (G696C).

Para. BL. A method for treating cancer in a subject, comprising
(a) identifying a subject having one or more mutations at an amino acid position in a biological sample from said subject, said one or more mutations selected from:
  (i) G595 and G667 of the TrkA polypeptide set forth in SEQ ID NO: 1;
  (ii) G639 and G709 of the TrkB polypeptide set forth in SEQ ID NO: 3;
  (iii) G623 and G696 of the TrkC polypeptide set forth in SEQ ID NO: 5;
  (iv) G1202 and 1269 of the ALK polypeptide set forth in SEQ ID NO: 7; and
  (v) G2032 and 2101 of the ROS1 polypeptide set forth in SEQ ID NO: 9; and
(b) administering a therapeutically effective amount of a pharmaceutical composition according to any one of Paras. A-AG to said subject.

Para. BM. A method according to Para. BL, wherein said biological sample comprises sputum, bronchoalveolar lavage, pleural effusion, tissue, whole blood, serum, plasma, buccal scrape, saliva, cerebrospinal fluid, urine, stool, circulating tumor cells, circulating nucleic acids, bone marrow, or any combination thereof.

Para. BN. A method according to any one of Paras. AH-BM, wherein said subject receives from about 50 mg to about 1200 mg of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, on a daily basis.

Para. BO. A method according to any one of Paras. AH-BM, wherein said pharmaceutical composition is administered to said subject once per day.

Para. BP. A method of preparing a pharmaceutical composition according to any one of Paras. A-AG, comprising:
(a) dissolving a mixture of said N-[5-(3,5-difluorobenzyl)-1H-indazol-3-yl]-4-(4-methyl-piperazin-1-yl)-2-(tetrahydro-pyran-4-ylamino)-benzamide, or a pharmaceutically acceptable salt thereof, and said at least one polymer in a solvent to form a solution; and
(b) spray drying said solution to form particles.

Para. BQ. A method according to Para. BP, wherein said particles are formed into a dosage form.

Para. BR. A method according to Para. BQ, wherein said dosage form is in the form of a granules, a powder, tablet or capsule.

Para. BS. A pharmaceutical composition according to Para. BR, wherein said pharmaceutical composition is in the form of a granules.

Para. BT. A pharmaceutical composition according to Para. BR, wherein said pharmaceutical composition is in the form of a powder.

Para. BU. A pharmaceutical composition according to Para. BR, wherein said pharmaceutical composition is in the form of a tablet.

Para. BV. A pharmaceutical composition according to Para. BR, wherein said pharmaceutical composition is in the form of a capsule.

We claim:

1. A pharmaceutical composition, comprising a solid dispersion of N-[(5-(3.5-difluorobenzyl)-1H-indazol-3-yl]-4-(4-methylpiperazin-1-yl)-2-(tetrahydropyran-4-ylamino)-bertzamide, or a pharmaceutically acceptable salt thereof, and at least one polymer, wherein the solid dispersion is prepared by spray-drying.

2. The pharmaceutical composition according to claim 1, wherein said N-[5-(3,5-difluorobenzyl)-1H-indazol-3-yl]-4-(4-methylpiperazin-1-yl)-2-(tetrahydropyran-4-ylamino)-benzamide, or a pharmaceutically acceptable salt thereof, is substantially amorphous.

3. The pharmaceutical composition according to claim 1, wherein said at least one polymer is selected from the group consisting of polyvinyl pyrrolidone, polyethyleneoxide, a copolymer of 1-vinyl-2-pyrrolidone and vinyl acetate, polymethacrylates, polyoxyethylene alkyl ethers, polyoxyethylene castor oils, polycaprolactam, polylactic acid, polyglycolic acid, poly(lactic-glycolic)acid, lipids, cellulose, pullulan, dextran, maltodextrin, hyaluronic acid, polysialic acid, chondroitin sulfate, heparin, fucoidan, pentosan polysulfate, spirulan, hydroxypropyl methyl cellulose, hydroxypropyl cellulose, carboxymethyl ethylcellulose, hydroxypropyl methylcellulose acetate succinate, cellulose acetate phthalate, cellulose acetate trimellitate, ethyl cellulose, cellulose acetate, cellulose butyrate, cellulose acetate butyrate, and dextran polymer derivative.

4. The pharmaceutical composition according to claim 1, wherein said pharmaceutical composition is in the form of particles.

5. The pharmaceutical composition according to claim 4, wherein said particles comprise a cellulose core.

6. The pharmaceutical composition according to claim 4, wherein an average diameter of said particles is from about 150 micrometers to about 300 micrometers.

7. The pharmaceutical composition according to claim 4, wherein not less than about 80% of said particles have a diameter from about 150 micrometers to about 300 micrometers.

8. The pharmaceutical composition according to claim 5, wherein said N-[5-(3,5-difluorobenzyl)-1 H-indazol-3-yl]-4-(4-methylpiperazin-1-yl)-2-(tetrahydropyran-4-ylamino)-benzamide, or a pharmaceutically acceptable salt thereof, and said at least one polymer comprise at least one layer on said cellulose core.

9. The pharmaceutical composition according to claim 1, wherein the weight to weight ratio of said N-[5-(3,5-difluorobenzyl)-1H-indazol-3-yl]-4-(4-methylpiperazin-1-yl)-2-(tetrahydropyran-4-ylamino)-benzamide, or a pharmaceutically acceptable salt thereof, to said at least one polymer is from about 1 to 10 to about 10 to 1.

10. The pharmaceutical composition according to claim 5, wherein the weight to weight ratio of said N-[5-(3,5-difluorobenzyl)-1H-indazol-3-yl]-4-(41-methylpiperazin-1-yl)-2-(tetrahydropyran-4-ylamino)-benzamide, or a pharmaceutically acceptable salt thereof, plus said at least one polymer to said cellulose core is from about 1 to 10 to about 10 to 1.

11. The pharmaceutical composition according to claim 8, wherein said at least one layer on said cellulose core has a thickness from about 5 micrometers to about 40 micrometers.

12. The pharmaceutical composition according to claim 1, wherein said at least one polymer comprises a copolymer of 1-vinyl-2-pyrrolidone and vinyl acetate.

13. The pharmaceutical composition according to claim 1, wherein said pharmaceutical composition releases at least about 25% of the total amount of said N-[5-(3,5-difluorobenzyl)-1H-indazol-3-yl]-4-(4-methylpiperazin-1-yl)-2-(tetrahydropyran-4-ylamino)-benzamide, or a pharmaceutically acceptable salt thereof, in about 60 minutes in pH 6.5 phosphate buffered saline.

14. The pharmaceutical composition according to claim 1, wherein said N-[5-(3,5-difluorobenzyl)-1H-indazol-3-yl]-4-(4-methylpiperazin-1-yl)-2-(tetrahydropyran-4-ylamino)-benzamide, or a pharmaceutically acceptable salt thereof comprises at least about 5% attic total weight of said composition.

15. The pharmaceutical composition according to claim 1, wherein said composition comprises from about 1% to about 25% by weight of water.

16. The pharmaceutical composition according to claim 1, wherein said composition comprises no more than about 10,000 parts per million of residual solvent.

17. A pharmaceutical composition according to claim 1, wherein said pharmaceutical composition is in the form of a granule, a powder, tablet or capsule.

18. A method of treating cancer in a subject in need thereof, comprising administering to said subject a therapeutically effective amount of a pharmaceutical composition according to claim 1.

19. The method according to claim 18, wherein said cancer is selected from anaplastic large-cell lymphoma (ALCL), colorectal cancer (CRC), cholangiocarcinoma, gastric, glioblastomas (GBM), leiomyosarcoma, melanoma, non-small cell lung cancer (NSCLC), squamous cell lung cancer, neuroblastoma (NB), ovarian cancer, pancreatic cancer, prostate cancer, medullary thyroid cancer, breast cancer, papillary thyroid cancer, or any combination thereof.

20. A method of preparing a pharmaceutical composition, the method comprising:

(a) dissolving a mixture of N-[5-(3,5-difluorobenzyl)-1H-indazol-3-yl]-4-(4-methylpiperazin-1-yl)-2-(tetrahydropyran-4-ylamino)-benzamide, or a pharmaceutically acceptable salt thereof and said at least one polymer in a solvent to form a solution; and (b) spray drying said solution to form particles;

wherein the composition comprises a solid dispersion of N-[5-(3,5-difluorobenzyl)-1H-indazol-3-yl]-4-(4-methylpiperazin-1-yl)-2-(tetrahydropyran-4-ylamino)-benzamide, or a pharmaceutically acceptable salt thereof, with the at least one polymer.

* * * * *

UNITED STATES PATENT AND TRADEMARK OFFICE
CERTIFICATE OF CORRECTION

PATENT NO. : 11,007,191 B2
APPLICATION NO. : 16/848676
DATED : May 18, 2021
INVENTOR(S) : Robert Orr et al.

It is certified that error appears in the above-identified patent and that said Letters Patent is hereby corrected as shown below:

In the Claims

Column 98 Claim 1, Lines 13-15, delete:
"N-[(5-(3.5-difluorobenzyl)-1H-indazol-3-yl]-4-(4-methylpiperazin-1-yl)-2-(tetrahydropyran-4-ylamino)-bertzamide"
And replace with:
-- N-[(5-(3,5-difluorobenzyl)-1H-indazol-3-yl]-4-(4-methylpiperazin-1-yl)-2-(tetrahydropyran-4-ylamino)-benzamide --.

Column 98 Claim 8, Lines 51-53, delete:
"N-[5-(3,5-difluorobenzyl)-1 H-indazol-3-yl]-4-(4-methylpiperazin-1-yl)-2-(tetrahydropyran-4-ylamino)-benzamide"
And replace with:
-- N-[5-(3,5-difluorobenzyl)-1H-indazol-3-yl]-4-(4-methylpiperazin-1-yl)-2-(tetrahydropyran-4-ylamino)-benzamide --.

Column 98 Claim 10, Lines 63-65, delete:
"N-[5-(3,5-difluorobenzyl)-1H-indazol-3-yl]-4-(41-methylpiperazin-1-yl)-2-(tetrahydropyran-4-ylamino)-benzamide"
And replace with:
-- N-[5-(3,5-difluorobenzyl)-1H-indazol-3-yl]-4-(4-methylpiperazin-1-yl)-2-(tetrahydropyran-4-ylamino)-benzamide --.

Column 99 Claim 13, Lines 10-12, delete:
"N-[5-(3.5-difluorobenzyl)-1H-indazol-3-yl]-4-(4-methylpiperazin-1-yl)-2-(tetrahydropyran-4-ylamino)-benzamide"
And replace with:
-- N-[5-(3,5-difluorobenzyl)-1H-indazol-3-yl]-4-(4-methylpiperazin-1-yl)-2-(tetrahydropyran-4-ylamino)-benzamide --.

Signed and Sealed this
Twelfth Day of July, 2022

Katherine Kelly Vidal
*Director of the United States Patent and Trademark Office*

CERTIFICATE OF CORRECTION (continued)
U.S. Pat. No. 11,007,191 B2

Column 99 Claim 14, Lines 17-19, delete:

"or a pharmaceutically acceptable salt thereof comprises at least about 5% attic total weight of said composition"

And replace with:

-- or a pharmaceutically acceptable salt thereof, comprises at least about 5% of the total weight of said composition --.